(12) United States Patent
Pafford et al.

(10) Patent No.: US 7,981,156 B2
(45) Date of Patent: *Jul. 19, 2011

(54) BONE GRAFTS

(75) Inventors: John Pafford, Germantown, TN (US); Lawrence M. Boyd, Memphis, TN (US); William F. McKay, Memphis, TN (US); Eddie F. Ray, III, Cordova, TN (US); James E. Van Hoeck, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 841 days.

This patent is subject to a terminal disclaimer.

(21) Appl. No.: 10/781,058

(22) Filed: Feb. 18, 2004

(65) Prior Publication Data

US 2005/0004672 A1    Jan. 6, 2005

Related U.S. Application Data

(60) Continuation of application No. 10/114,675, filed on Apr. 2, 2002, now abandoned, which is a continuation of application No. 09/484,354, filed on Jan. 18, 2000, now Pat. No. 6,371,988, which is a division of application No. 08/740,031, filed on Oct. 23, 1996, now abandoned, which is a continuation-in-part of application No. 08/603,676, filed on Feb. 20, 1996, now Pat. No. 6,423,095, which is a continuation-in-part of application No. 08/543,563, filed on Oct. 16, 1995, now abandoned.

(51) Int. Cl.
A61F 2/44 (2006.01)
A61F 2/28 (2006.01)

(52) U.S. Cl. .................. 623/17.11; 623/23.63

(58) Field of Classification Search .................. None
See application file for complete search history.

(56) References Cited

U.S. PATENT DOCUMENTS

| | | |
|---|---|---|
| 2,677,369 A | 3/1952 | Knowles |
| 3,848,601 A | 11/1974 | Ma et al. |
| 3,918,100 A | 11/1975 | Shaw et al. |
| 4,309,777 A | 1/1982 | Patil |
| 4,330,891 A | 5/1982 | Branemark et al. |

(Continued)

FOREIGN PATENT DOCUMENTS

EP    0077159    4/1983

(Continued)

OTHER PUBLICATIONS

Cloward, Ralph B., M.D. Honolulu, Hawaii. The Anterior Approach for Removal of Ruptured Cervical Disks. Presented at the meeting of the Harvey Cushing Society, Washington, D.C. Apr. 22, 1958, pp. 602-617.

(Continued)

*Primary Examiner* — David H. Willse

(57) ABSTRACT

Spinal spacers 20 are provided for fusion of a motion segment. The spacers include a load bearing member 21 having a wall 22 sized for engagement within a space between adjacent vertebrae to maintain the space and an effective amount of an osteogenic composition to stimulate osteoinduction. The osteogenic composition includes a substantially pure osteogenic factor in a pharmaceutically acceptable carrier. In one embodiment the load bearing member includes a bone graft impregnated in an osteogenic composition. In another embodiment, the osteogenic composition 30 is packed within a chamber 25 defined in the graft. Any suitable configuration of a bone graft is contemplated, including bone dowels, D-shaped spacers and cortical rings.

45 Claims, 40 Drawing Sheets

U.S. PATENT DOCUMENTS

| | | |
|---|---|---|
| 4,349,921 A | 9/1982 | Kuntz |
| 4,394,370 A | 7/1983 | Jefferies |
| 4,440,750 A | 4/1984 | Glowacki et al. |
| 4,501,269 A | 2/1985 | Bagby |
| 4,526,909 A | 7/1985 | Urist |
| 4,596,574 A | 6/1986 | Urist |
| 4,599,086 A | 7/1986 | Doty |
| 4,620,327 A | 11/1986 | Caplan et al. |
| 4,623,553 A | 11/1986 | Ries et al. |
| 4,714,469 A | 12/1987 | Kenna |
| 4,743,256 A | 5/1988 | Brantigan |
| 4,759,766 A | 7/1988 | Buettner-Janz et al. |
| 4,772,287 A | 9/1988 | Ray et al. |
| 4,834,757 A | 5/1989 | Brantigan |
| 4,877,020 A | 10/1989 | Vich |
| 4,878,915 A | 11/1989 | Brantigan |
| 4,904,261 A | 2/1990 | Dove et al. |
| 4,917,704 A | 4/1990 | Frey et al. |
| 4,950,296 A | 8/1990 | McIntyre |
| 4,961,740 A * | 10/1990 | Ray et al. ............ 606/61 |
| 5,013,649 A * | 5/1991 | Wang et al. ............ 435/69.1 |
| 5,015,247 A | 5/1991 | Michelson |
| 5,071,437 A | 12/1991 | Steffee |
| 5,133,755 A | 7/1992 | Brekke |
| 5,147,402 A | 9/1992 | Bohler |
| 5,192,327 A | 3/1993 | Brantigan |
| 5,207,710 A | 5/1993 | Chu |
| 5,258,029 A | 11/1993 | Chu et al. |
| 5,282,861 A | 2/1994 | Kaplan |
| 5,290,558 A * | 3/1994 | O'Leary et al. ............ 424/422 |
| 5,306,307 A | 4/1994 | Senter et al. |
| 5,306,309 A | 4/1994 | Wagner et al. |
| 5,306,310 A | 4/1994 | Siebels |
| 5,314,476 A * | 5/1994 | Prewett et al. ............ 623/23.63 |
| 5,344,654 A | 9/1994 | Rueger et al. |
| 5,348,026 A | 9/1994 | Davidson |
| 5,366,508 A | 11/1994 | Brekke |
| 5,397,364 A | 3/1995 | Kozak et al. |
| 5,405,391 A | 4/1995 | Henderson et al. |
| 5,425,772 A | 6/1995 | Brantigan |
| 5,443,514 A | 8/1995 | Steffee |
| 5,458,638 A | 10/1995 | Kuslich et al. |
| 5,514,180 A | 5/1996 | Heggeness et al. |
| 5,522,899 A | 6/1996 | Michelson |
| 5,593,409 A * | 1/1997 | Michelson ............ 606/61 |
| 5,609,635 A | 3/1997 | Michelson |
| 5,645,591 A | 7/1997 | Kuberasampath et al. |
| 5,645,596 A | 7/1997 | Kim et al. |
| 5,674,292 A | 10/1997 | Tucker et al. |
| 5,683,464 A | 11/1997 | Wagner |
| 5,814,084 A | 9/1998 | Grivas et al. |
| 5,865,845 A | 2/1999 | Thalgott |
| 5,989,289 A | 11/1999 | Coates et al. |
| 6,039,762 A | 3/2000 | McKay |
| 6,077,988 A * | 6/2000 | Kuberasampath et al. 623/16.11 |
| 6,096,081 A | 8/2000 | Grivas et al. |
| 6,111,164 A | 8/2000 | Rainey et al. |

FOREIGN PATENT DOCUMENTS

| | | |
|---|---|---|
| EP | 0179696 | 4/1986 |
| EP | 0307241 | 3/1989 |
| EP | 0 567 391 A1 * | 10/1993 |
| EP | 0 585 168 A2 * | 3/1994 |
| EP | 0 599 419 A2 | 6/1994 |
| EP | 0599419 | 6/1994 |
| ES | 1030080 | 2/1995 |
| WO | WO 86/00526 | 1/1986 |
| WO | WO 90/00037 | 1/1990 |
| WO | WO 92/14423 | 9/1992 |
| WO | WO 94/25892 | 11/1994 |
| WO | WO 94/25893 | 11/1994 |
| WO | WO 94/26893 | 11/1994 |
| WO | WO 95/08306 | 3/1995 |
| WO | WO 95/31947 | 11/1995 |
| WO | WO 96/40013 | 12/1996 |
| WO | WO 97/13378 | 4/1997 |
| WO | WO 97/14378 | 4/1997 |
| WO | WO 97/15248 | 5/1997 |
| WO | WO 97/25945 | 7/1997 |

OTHER PUBLICATIONS

Smith, George W. MD, Robinson, Robert A., MD. The treatment of Certain Cervical-Spine Disorders by Anterior Removal of the Intervertebral Disk and Interbody Fusion. The Journal of Bone and Joint Surgery. vol. 40-A, No. 3, Jun. 1958, pp. 607-624.

Proceedings. 10th Annual Conf. North American Spine Society. Oct. 18-21, 1995. Washington, DC, pp. 10-11.

Stephen M. David, MD, et al., "Lumbar Spinal Fusion Using Recombinant Human Bone Morphogenetic Protein: A Randomized, Blinded and Controlled Study." American Academy of Orthopaedic Surgeons 1996 Annual Meeting-Scientific Program; Paper No. 74, Feb. 22, 1996, 1 page.

Yamamuro, Takao, et al. Replacement of the Lumbar Vertebrae of Sheep w/Ceramic Prostheses. The Journal of Bone and Joint Surgery. vol. 72-B, No. 5, Sep. 1990, pp. 889-893.

Gerhart, Tobin N., M.D., et al. Healing Segmental Femoral Defects in Sheep Using Recombinant Human Bone Morphogenetic Protein. Clinical Orthopaedics and Related Research, No. 293, pp. 317-326, Aug. 1993.

Preliminary Program. Forty-Second Annual Meeting of the Orthopaedic Research Society. Hyatt Regency, Atlanta, Georgia, Feb. 18-22, 1996, p. 12.

Musculoskeletal Transplant Foundation. EndoDowel, Oct. 1996, 3 pages.

Marcus F. Sciadini, MD, et al., "Evaluation of Recombinant Human Bone Morphogenetic Protein-2 With a Collagen Carrier in a Canine Segmental Defect Model: Dose Response and Long-Term Results." Amer. Acad. of Orthopaedic Surg. 1996 Annual Meeting-Scientific Program; Paper No. 75. Feb. 22, 1996, 1 page.

Musculoskeletal Transplant Foundation. Quality Must be First Priority. Marketing materials of Depuy Motech. Apr. 1996, pp. 1-16.

Simmons, J.W. Bone Banking. Lumbar Spine Surgery: Techniques and Complications. A. White and T. Rothman, eds. pp. 459-470. Mosby, St. Louis, 1987.

Albee, F.H. et al. Bone Graft Surgery in Disease, Injury and Deformity. D. Appleton-Century Company, Inc. (publisher), 1940. pp. xi-xv; 1-31; 48-107; and 210-227.

Vich, J.M.O., MD. Anterior cervical interbody fusion with threaded Cylindrical bone. Journal of Neurosurgery, vol. 63, pp. 750-753, Nov. 1985.

Vich, J.M.O., MD. Update on the Cloward procedure: new instruments. Journal of Neurosurgery, vol. 81, pp. 716-720, Nov. 1994.

Sofamor Danek. Sofamor Danek Laparoscopic Bone Dowel System Laparoscopic Surgial Procedure. Laparoscopic Bone Dowel Surgical Technique. 1995, 17 pages.

Sofamor Danek. Laparoscopic Bone Dowel Instruments. Product information. 1995, 3 pages.

*Albee, F. H., M.D., "Bone Graft Surgery" *Bone Graft Surgery in Disease, Injury and Deformity*, 1940, pp. 20-22.

*Vich, J. M., M.D., "Anterior Cervical Interbody Fusion with Threaded Cylindrical Bone", *J. Neurosurg* 63:750-753 1985.

*Vich, J. M., M.D., "Update on the Cloward Procedure: New Instruments", *J. Neurosurg*, vol. 81, Nov. 1994.

* cited by examiner

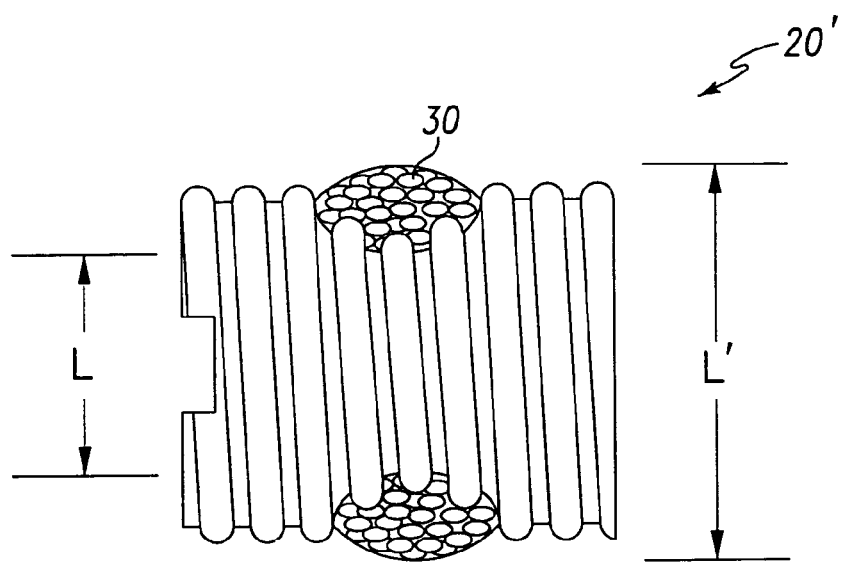
Fig. 6
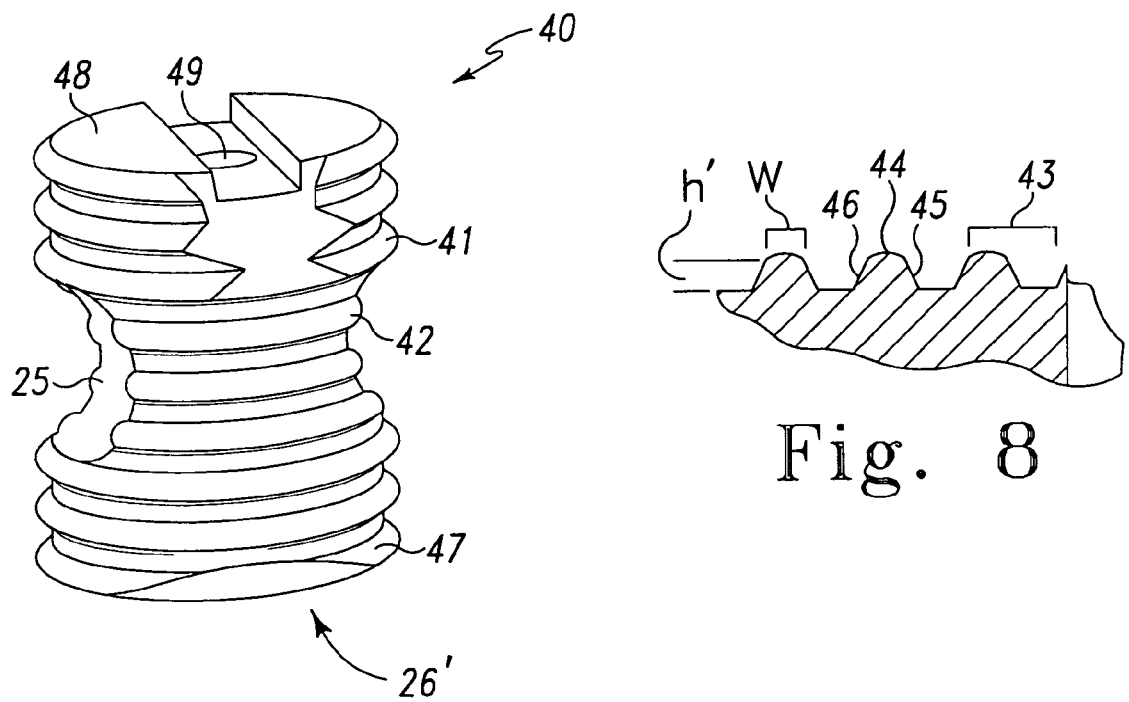
Fig. 7
Fig. 8

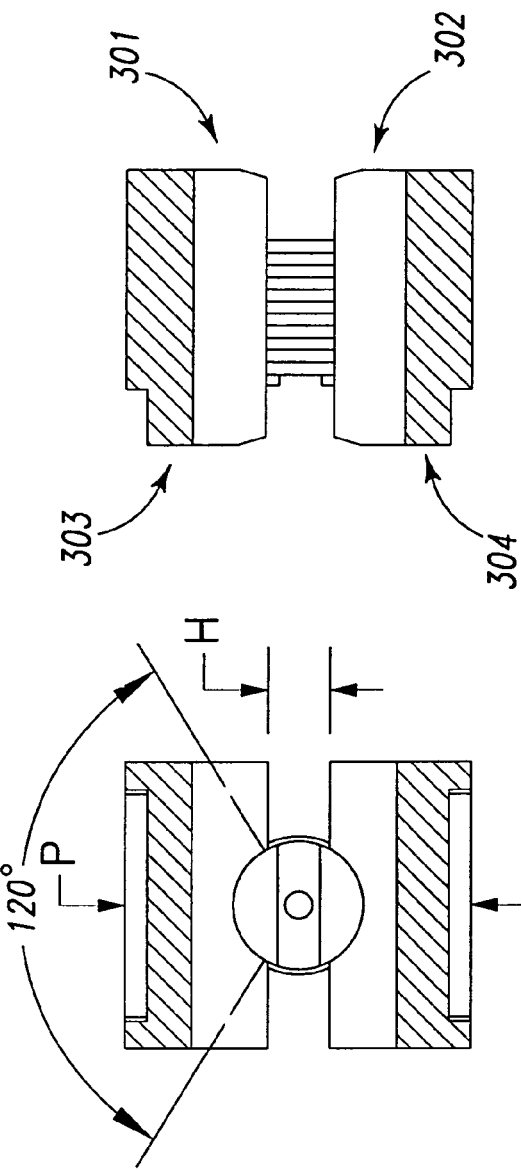
Fig. 52
Fig. 51
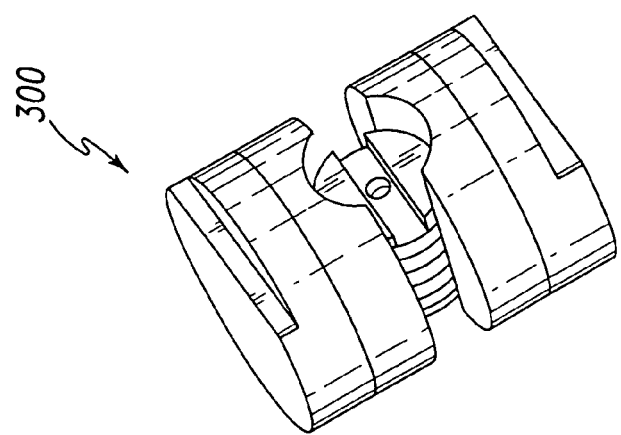
Fig. 50

BONE GRAFTS

CROSS-REFERENCE TO RELATED APPLICATIONS

This application claims priority to all of the following applications and is a continuation of U.S. patent application Ser. No. 10/114,675 filed Apr. 2, 2002, now abandoned, which is a continuation of U.S. patent application Ser. No. 09/484,354 filed Jan. 18, 2000, now U.S. Pat. No. 6,371,988, which is a divisional of U.S. patent application Ser. No. 08/740,031 filed Oct. 23, 1996, now abandoned, which is a continuation-in-part of U.S. patent application Ser. No. 08/603,676 filed Feb. 20, 1996, now U.S. Pat. No. 6,423,095, which is a continuation-in-part of U.S. patent application Ser. No. 08/543,563 filed Oct. 16, 1995 now abandoned, all of which are incorporated by reference in their entirety.

FIELD OF THE INVENTION

The present invention relates to spacers, compositions, instruments and methods for arthrodesis. In specific applications of the invention the spacers include bone grafts in synergistic combination with osteogenic compositions.

BACKGROUND OF THE INVENTION

Spinal fusion is indicated to provide stabilization of the spinal column for painful spinal motion and disorders such as structural deformity, traumatic instability, degenerative instability, and post-resection iatrogenic instability. Fusion, or arthrodesis, is achieved by the formation of an osseous bridge between adjacent motion segments. This can be accomplished within the disc space, anteriorly between contiguous vertebral bodies or posteriorly between consecutive transverse processes, laminae or other posterior aspects of the vertebrae.

An osseous bridge, or fusion mass, is biologically produced by the body upon skeletal injury. This normal bone healing response is used by surgeons to induce fusion across abnormal spinal segments by recreating spinal injury conditions along the fusion site and then allowing the bone to heal. A successful fusion requires the presence of osteogenic or osteopotential cells, adequate blood supply, sufficient inflammatory response, and appropriate preparation of local bone. This biological environment is typically provided in a surgical setting by decortication, or removal of the outer, cortical bone to expose the vascular, cancellous bone, and the deposition of an adequate quantity of high quality graft material.

A fusion or arthrodesis procedure is often performed to treat an anomoly involving an intervertebral disc. Intervertebral discs, located between the endplates of adjacent vertebrae, stabilize the spine, distribute forces between vertebrae and cushion vertebral bodies. A normal intervertebral disc includes a semi-gelatinous component, the nucleus pulposus, which is surrounded and confined by an outer, fibrous ring called the annulus fibrosis. In a healthy, undamaged spine, the annulus fibrosis prevents the nucleus pulposus from protruding outside the disc space.

Spinal discs may be displaced or damaged due to trauma, disease or aging. Disruption of the annulus fibrosis allows the nucleus pulposus to protrude into the vertebral canal, a condition commonly referred to as a herniated or ruptured disc. The extruded nucleus pulposus may press on the spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

Sometimes the only relief from the symptoms of these conditions is a discectomy, or surgical removal of a portion or all of an intervertebral disc followed by fusion of the adjacent vertebrae. The removal of the damaged or unhealthy disc will allow the disc space to collapse. Collapse of the disc space can cause instability of the spine, abnormal joint mechanics, premature development of arthritis or nerve damage, in addition to severe pain. Pain relief via discectomy and arthrodesis requires preservation of the disc space and eventual fusion of the affected motion segments.

Bone grafts are often used to fill the intervertebral space to prevent disc space collapse and promote fusion of the adjacent vertebrae across the disc space. In early techniques, bone material was simply disposed between the adjacent vertebrae, typically at the posterior aspect of the vertebrae, and the spinal column was stabilized by way of a plate or rod spanning the affected vertebrae. Once fusion occurred the hardware used to maintain the stability of the segment became superfluous and was a permanent foreign body. Moreover, the surgical procedures necessary to implant a rod or plate to stabilize the level during fusion were frequently lengthy and involved.

It was therefore determined that a more optimal solution to the stabilization of an excised disc space is to fuse the vertebrae between their respective end plates, preferably without the need for anterior or posterior plating. There have been an extensive number of attempts to develop an acceptable intradiscal implant that could be used to replace a damaged disc and maintain the stability of the disc interspace between the adjacent vertebrae, at least until complete arthrodesis is achieved. To be successful the implant must provide temporary support and allow bone ingrowth. Success of the discectomy and fusion procedure requires the development of a contiguous growth of bone to create a solid mass-because the implant may not withstand the cyclic compressive spinal loads for the life of the patient.

Many attempts to restore the intervertebral disc space after removal of the disc have relied on metal devices. U.S. Pat. No. 4,878,915 to Brantigan teaches a solid metal plug. U.S. Pat. Nos. 5,044,104; 5,026,373 and 4,961,740 to Ray; 5,015,247 to Michelson and U.S. Pat. No. 4,820,305 to Harms et al., U.S. Pat. No. 5,147,402 to Bohler et al. and U.S. Pat. No. 5,192,327 to Brantigan teach hollow metal cage structures. Unfortunately, due to the stiffness of the material, some metal implants may stress shield the bone graft, increasing the time required for fusion or causing the bone graft to resorb inside the cage. Subsidence, or sinking of the device into bone, may also occur when metal implants are implanted between vertebrae if fusion is delayed. Metal devices are also foreign bodies which can never be fully incorporated into the fusion mass.

Various bone grafts and bone graft substitutes have also been used to promote osteogenesis and to avoid the disadvantages of metal implants. Autograft is often preferred because it is osteoinductive. Both allograft and autograft are biological materials which are replaced over time with the patient's own bone, via the process of creeping substitution. Over time a bone graft virtually disappears unlike a metal implant which persists long after its useful life. Stress shielding is avoided because bone grafts have a similar modulus of elasticity as the surrounding bone. Commonly used implant materials have stiffness values far in excess of both cortical and cancellous bone. Titanium alloy has a stiffness value of 114 Gpa and 316L stainless steel has a stiffness of 193 Gpa. Cortical bone, on the other hand, has a stiffness value of about 17 Gpa. Moreover, bone as an implant also allows excellent postoperative imaging because it does not cause scattering like metallic implants on CT or MRI imaging.

Various implants have been constructed from bone or graft substitute materials to fill the intervertebral space after the removal of the disc. For example, the Cloward dowel is a circular graft made by drilling an allogenic or autogenic plug from the illium. Cloward dowels are bicortical, having porous cancellous bone between two cortical surfaces. Such dowels have relatively poor biomechanical properties, in particular a low compressive strength. Therefore, the Cloward dowel is not suitable as an intervertebral spacer without internal fixation due to the risk of collapsing prior to fusion under the intense cyclic loads of the spine.

Bone dowels having greater biomechanical properties have been produced and marketed by the University of Florida Tissue Bank, Inc., 1 Progress Boulevard, P.O. Box 31, S. Wing, Alachua, Fla. 32615. Unicortical dowels from allogenic femoral or tibial condyles are available. The University of Florida has also developed a diaphysial cortical dowel having superior mechanical properties. This dowel also provides the further advantage of having a naturally preformed cavity formed by the existing medullary canal of the donor long bone. The cavity can be packed with osteogenic materials such as bone or bioceramic.

Unfortunately, the use of bone grafts presents several disadvantages. Autograft is available in only limited quantities. The additional surgery also increases the risk of infection and blood loss and may reduce structural integrity at the donor site. Furthermore, some patients complain that the graft harvesting surgery causes more short-term and long-term pain than the fusion surgery.

Allograft material, which is obtained from donors of the same species, is more readily obtained. However, allogenic bone does not have the osteoinductive potential of autogenous bone and therefore may provide only temporary support. The slow rate of fusion using allografted bone can lead to collapse of the disc space before fusion is accomplished.

Both allograft and autograft present additional difficulties. Graft alone may not provide the stability required to withstand spinal loads. Internal fixation can address this problem but presents its own disadvantages such as the need for more complex surgery as well as the disadvantages of metal fixation devices. Also, the surgeon is often required to repeatedly trim the graft material to obtain the correct size to fill and stabilize the disc space. This trial and error approach increases the length of time required for surgery. Furthermore, the graft material usually has a smooth surface which does not provide a good friction fit between the adjacent vertebrae. Slippage of the graft may case neural and vascular injury, as well as collapse of the disc space. Even where slippage does not occur, micromotion at the graft/fusion-site interface may disrupt the healing process that is required for fusion.

Several attempts have been made to develop a bone graft substitute which avoids the disadvantages of metal implants and bone grafts while capturing advantages of both. For example Unilab, Inc. markets various spinal implants composed of hydroxyapatite and bovine collagen. In each case developing an implant having the biomechanical properties of metal and the biological properties of bone without the disadvantages of either has been extremely difficult or impossible.

A need has remained for fusion spacers which stimulate bone ingrowth and avoid the disadvantages of metal implants yet provide sufficient strength to support the vertebral column until the adjacent vertebrae are fused.

SUMMARY OF THE INVENTION

In accordance with one aspect of the invention, spinal spacers and compositions are provided for fusion of a motion segment. The spacers include a load bearing member sized for engagement within a space between adjacent vertebrae to maintain the space and an effective amount of an osteogenic composition to stimulate osteoinduction. The osteogenic composition includes a substantially pure osteogenic factor in a pharmaceutically acceptable carrier. In one embodiment the load bearing member includes a bone graft impregnated with an osteogenic composition. In another embodiment, the osteogenic composition is packed within a chamber defined in the graft. The grafts include bone dowels, D-shaped spacers and cortical rings.

One object of the invention is to provide spacers for engagement between vertebrae which encourages bone ingrowth and avoids stress shielding. Another object of the invention is to provide a spacer which restores the intervertebral disc space and supports the vertebral column while promoting bone ingrowth.

One benefit of the spacers of the present invention is that they combine the advantages of bone grafts with the advantages of metals, without the corresponding disadvantages. An additional benefit is that the invention provides a stable scaffold for bone ingrowth before fusion occurs. Still another benefit of this invention is that it allows the use of bone grafts without the need for metal cages or internal fixation, due to the increased speed of fusion. Other objects and further benefits of the present invention will become apparent to persons of ordinary skill in the art from the following written description and accompanying Figures.

BRIEF DESCRIPTION OF THE DRAWINGS

FIG. 6 is a side elevational view of the dowel shown in FIG. 5.

FIG. 7 is a perspective view of another dowel provided by this invention.

FIG. 8 is a detail of the threads of the dowel shown in FIG. 7.

FIG. 50 is a side perspective view of an axial test fixture for testing dowels of this invention.

FIG. 51 is a front cross-sectional view of the fixture of FIG. 50.

FIG. 52 is a side cross-sectional view of the fixture of FIGS. 50 and 51.

DESCRIPTION OF THE PREFERRED EMBODIMENT

Figure 1:
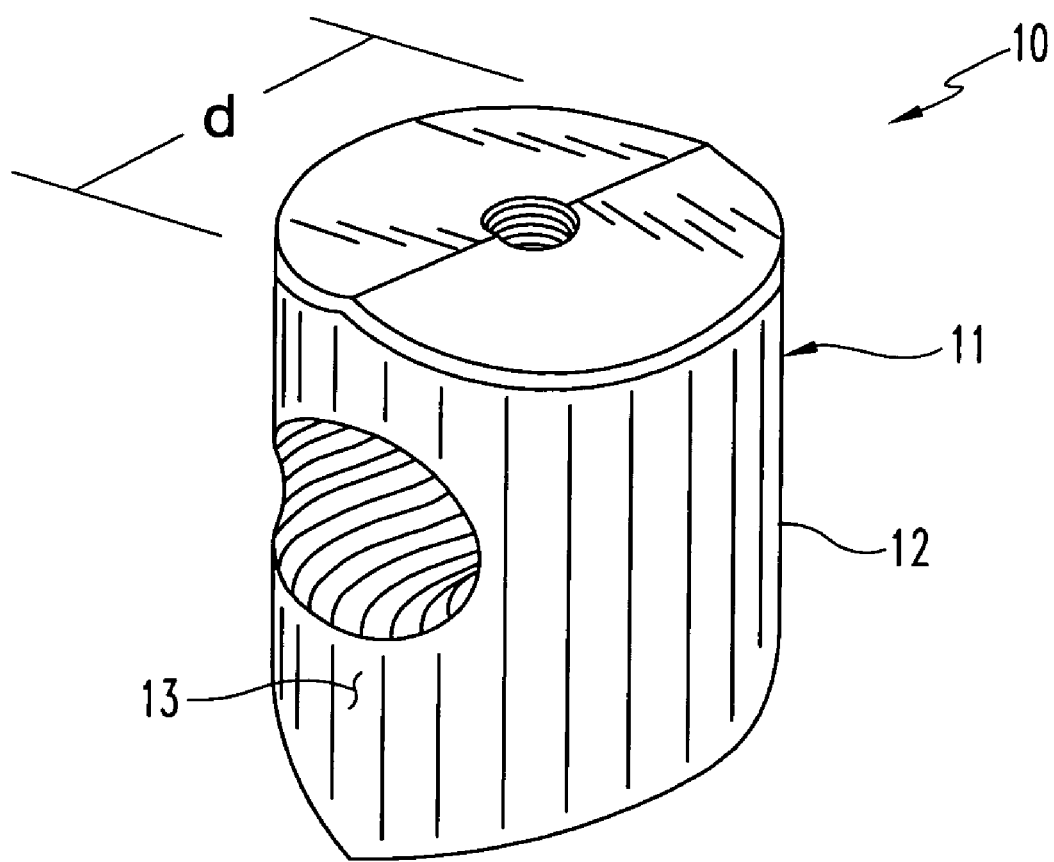
FIG. 1 is a top perspective view of a bone dowel according to this invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated spacers, and such further applications of the principles of the invention as illustrated therein being contemplated as would normally occur to one skilled in the art to which the invention relates.

The present invention provides bone grafts in synergistic combination with an osteogenic material, such as a bone morphogenic protein (BMP). The combination of BMP with a bone graft provides the advantages of a bone graft while enhancing bone growth into and incorporation of the graft, resulting in fusion quicker than with graft alone. The quicker fusion rates provided by this invention compensate for the less desirable biomechanical properties of graft and makes the use of internal fixation and metal interbody fusion devices unnecessary. The spacers of this invention are not required to support the cyclic loads of the spine for very long because of the quick fusion rates which reduce the biomechanical demands on the spacer. Therefore this invention capitalizes on the advantages of graft while avoiding the disadvantages.

The spinal spacers of this invention include a load bearing member sized for engagement within a space between adjacent vertebrae to maintain the space. The load bearing member is a bone graft in synergistic combination with an osteogenic material. The bone graft is any suitable bone material, preferably of human origin, including tibial, fibial, humeral, iliac, etc. The load bearing members of this invention include flat D-shaped spacers, bone dowels, cortical rings and any suitably shaped load bearing member composed of bone. A preferred load bearing member is obtained from the diaphysis of a long bone having a medullary canal which forms a natural chamber in the graft.

This invention provides the further advantage of exploiting the discovery that bone is an excellent carrier for osteogenic factors such as bone morphogenic proteins. Hydroxyapatite which is very similar in chemical composition to the mineral in cortical bone is an osteogenic factor-binding agent which controls the rate of delivery of certain proteins to the fusion site. Calcium phosphate compositions such as hydroxyapatite are thought to bind bone morphogenic proteins and prevent BMP from prematurely dissipating from the spacer before fusion can occur. It is further believed that retention of the BMP by the agent permits the protein to initiate the transformation of mesenchymal stem cells into bone producing cells (osteoblasts) within the device at a rate that is conducive to complete and rapid bone formation and ultimately, fusion across the disc space. The spacers of this invention have the advantage of including a load bearing member composed of bone which naturally binds and provides controlled delivery of osteogenic factors such as bone morphogenic proteins.

This invention also capitalizes on the discovery that cortical bone, like metal, can be conveniently machined into the various shapes disclosed herein. In some embodiments, the load bearing members define threads on an outer surface. Machined surfaces, such as threads, provide several advantages that were previously only available with metal implants. Threads allow better control of spacer insertion than can be obtained with a smooth surface. This allows the surgeon to more accurately position the spacer which is extremely important around the critical neurological and vascular structures of the spinal column. Threads and the like also provide increased surface area which facilitates the process of bone healing and creeping substitution for replacement of the donor bone material and fusion. These features also increase post-operative stability of the spacer by engaging the adjacent vertebral endplates and anchoring the spacer to prevent expulsion. This is a major advantage over smooth grafts. Surface features also stabilize the bone-spacer interface and reduce micromotion to facilitate incorporation and fusion.

Figure 2:
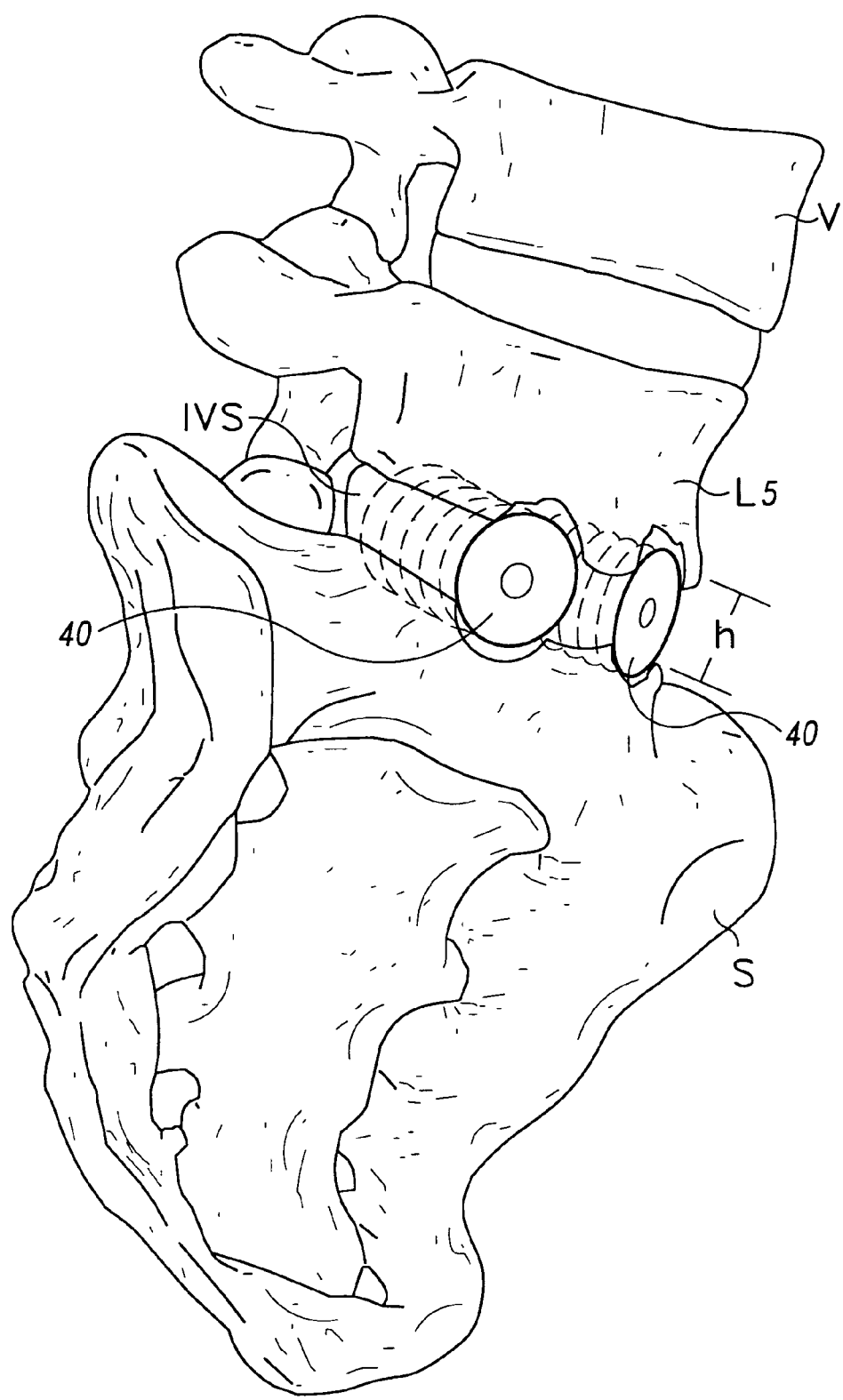
FIG. 2 shows bilateral dowel placement between L5 and the sacrum.

In one specific embodiment depicted in FIG. 1, the load bearing member of the spacer 10 is a bone dowel 11 soaked with an effective amount of an osteogenic composition to stimulate osteoinduction. Preferably, the osteogenic composition includes a substantially pure osteogenic factor in a pharmaceutically acceptable carrier. The dowel 10 includes a wall 12 sized for engagement within the intervertebral space IVS to maintain the space IVS. The wall 12 defines an outer engaging surface 13 for contacting the adjacent vertebrae. The wall 12 is preferably cylindrical so that the bone dowel 10 has a diameter d which is larger than the height h of the space IVS between adjacent vertebrae V or the height of the space between the lowest lumbar vertebrae L5 and the sacrum S as depicted in FIG. 2.

Figure 3:
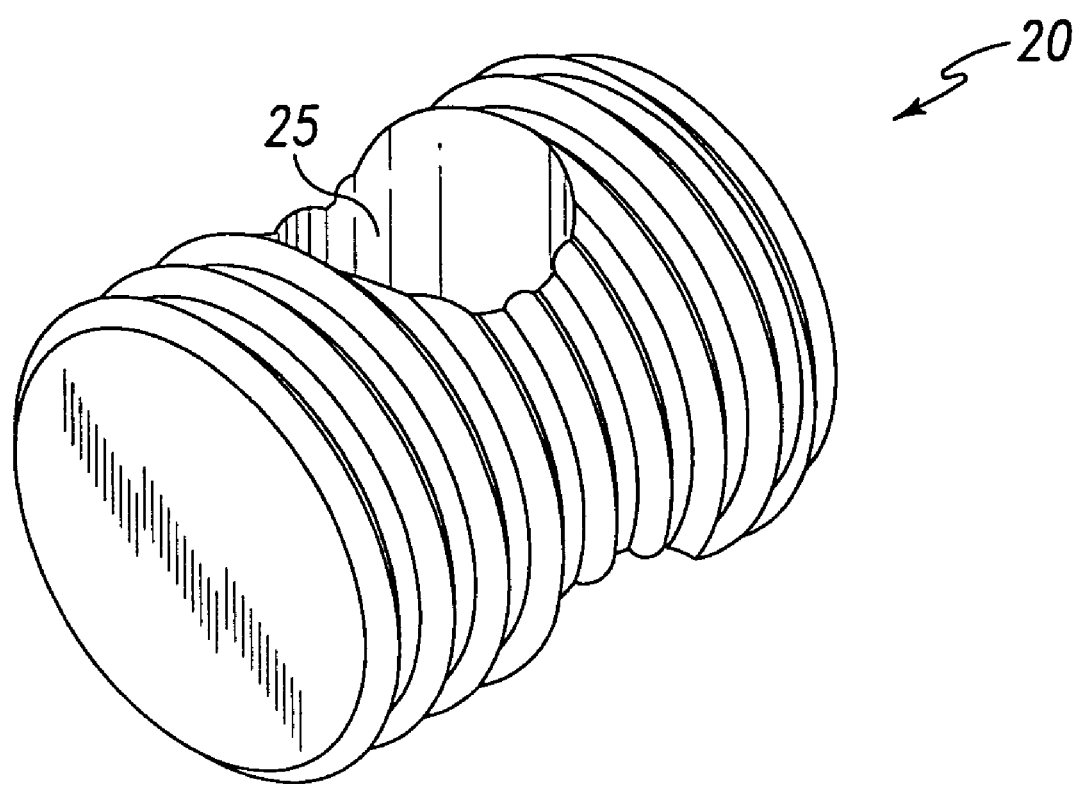
FIG. 3 is a perspective view of a cortical dowel having a chamber.
Figure 4:
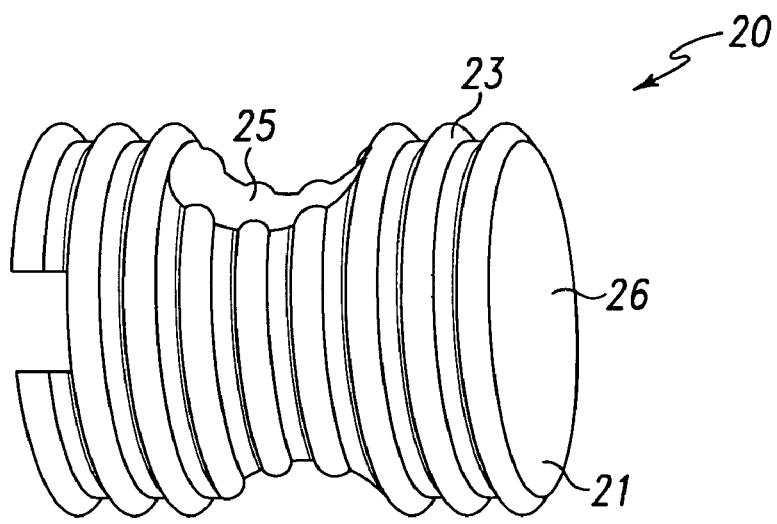
FIG. 4 is a side perspective view of a dowel according to this invention.
Figure 5:
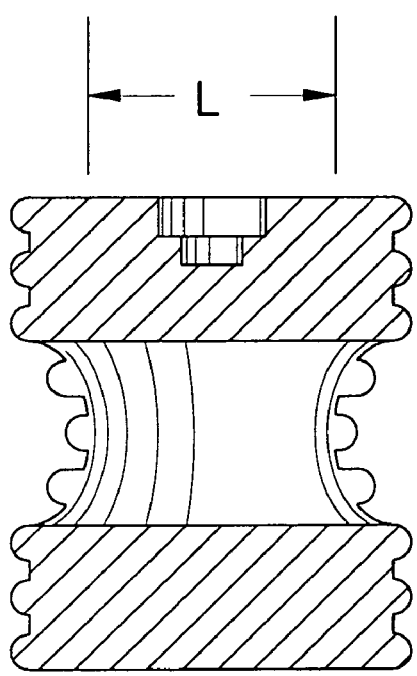
FIG. 5 is a cross-section of another dowel of this invention.

In another embodiment 20 depicted in FIG. 3, the load bearing member is a bone dowel 21 which includes a wall 22 having an engagement surface 23. The wall 22 defines a chamber 25 therethrough. Preferably, the load bearing member is a bone graft obtained from the diaphysis of a long bone having a medullary canal which forms the chamber 25. The chamber 25 is most preferably packed with an osteogenic composition to stimulate osteoinduction. The chamber 25 is preferably defined through a pair of outer engaging surfaces 23 so that the composition has maximum contact with the endplates of the adjacent vertebrae. Referring now to FIG. 4, the spacer 21 includes a solid protective wall 26 which is positionable to protect the spinal cord from escape or leakage of the osteogenic composition 30 within the chamber 25. In anterior approaches, the protective wall 26 is posterior. Preferably, the osteogenic composition 30 has a length which is greater than the length of the chamber (FIGS. 5 and 6) and the composition 30 is disposed within the chamber 25 to contact the end plates of adjacent vertebrae when the spacer 20' is implanted between the vertebrae. This provides better contact of the composition with the end plates to stimulate osteoinduction.

Various features can be machined on the outer surfaces of the dowels of this invention. In one embodiment shown in FIG. 7, the dowel 40 includes an outer engaging surface 41 defining threads 42. The initial or starter thread 47 is adjacent the protective wall 26'. As shown more clearly in FIG. 8, the threads are preferably uniformally machined threads which include teeth 43 having a crest 44 between a leading flank 45 and an opposite trailing flank 46. Preferably the crest 44 of each tooth 43 is flat. In one specific embodiment, the crest 44 of each tooth 43 has a width w of between about 0.020 inches and about 0.030 inches. The threads 42 preferably define an angle α between the leading flank 45 and the trailing flank 46 of adjacent ones of said teeth 43. The angle α is preferably between about 50 degrees and 70 degrees. Each tooth 43 preferably has a height h' which is about 0.030 inches and about 0.045 inches.

Referring again to FIG. 7, in some embodiments, the dowel 40 is provided with a tool engaging hole 49 in a wall 48 opposite the solid protective wall 26'. The tool engaging hole 49 is provided in a surface of the dowel which is adjacent the surgeon and opposite the initial thread 47. For an anterior procedure, the tool engaging tool hole 49 would be provided in the anterior surface 48 of the dowel 40. Other machined features are contemplated in the outer or bone engaging surfaces 41. Such machine features include surface rougheningssuch as knurlings and ratchetings.

In a most preferred embodiment, the tool engaging hole 49 is threaded to receive a threaded tip of an implanting tool. The inserter 60 shown in FIG. 9 includes a handle portion 61 and a shaft 62 extends from the handle 61. The distal end 63 of the shaft 62 includes a tip 65 which mates with the tool engaging hole 49. Preferably the tip 65 and the tool engaging hole 49 have corresponding mating threads 66, 49A. The inserter 60 preferably includes a T-handle for spacer control and positioning. The shaft 62 of the inserter 60 also includes a depth stop 64. Preferably the inserter 60 includes means for rotating the threaded tip 65. Knob 68 is engaged to the tip 65 through an intershaft extending through an internal bore (not shown) in the handle 61 and in the shaft 62. The tip 65 is preferably at the end of the intershaft with the intershaft rotatingly mounted within the handle 61 and the shaft 62.

Figure 10A:
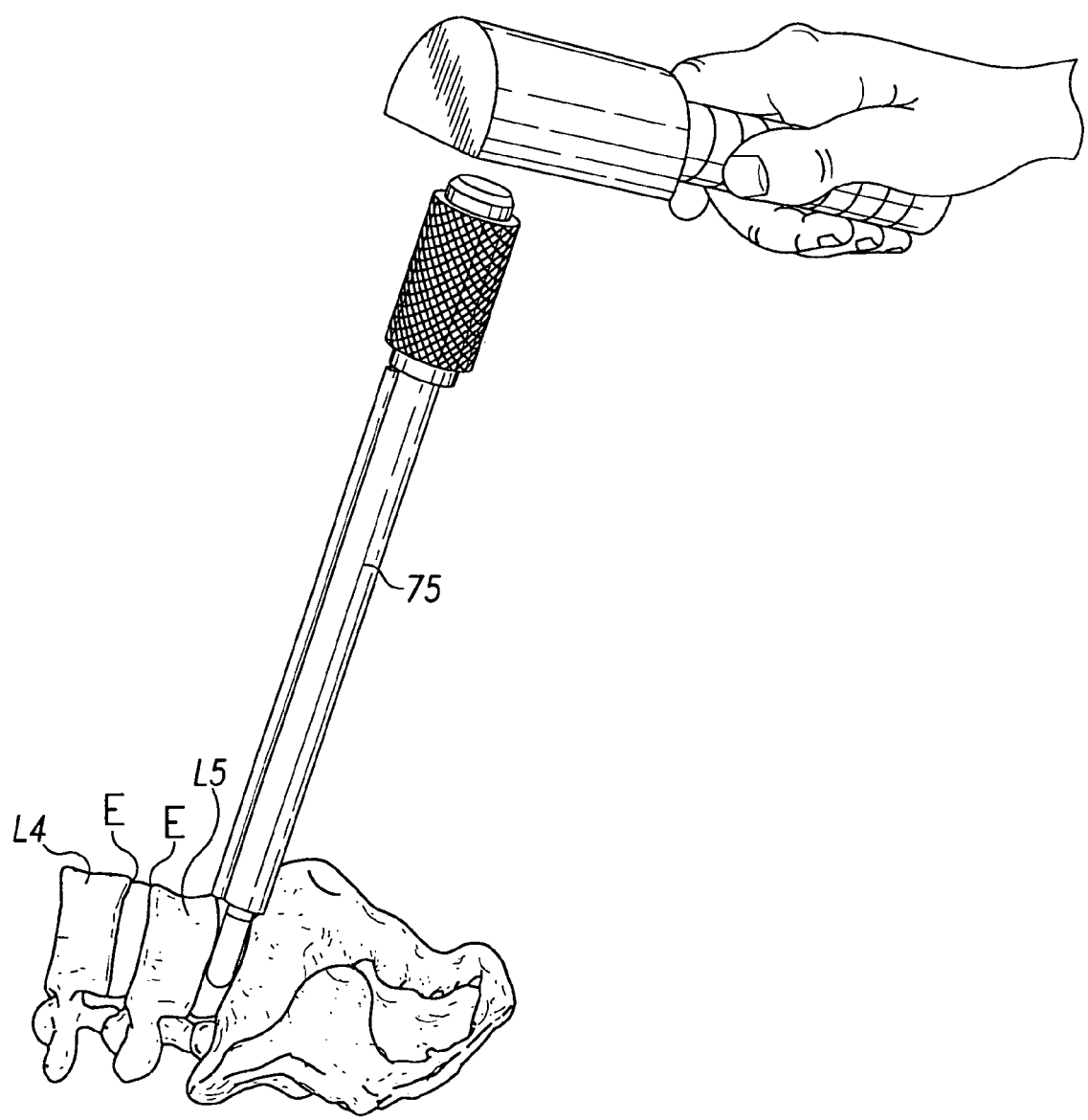
FIG. 10A is a side perspective view of the dilation of a disc space.
Figure 10B:
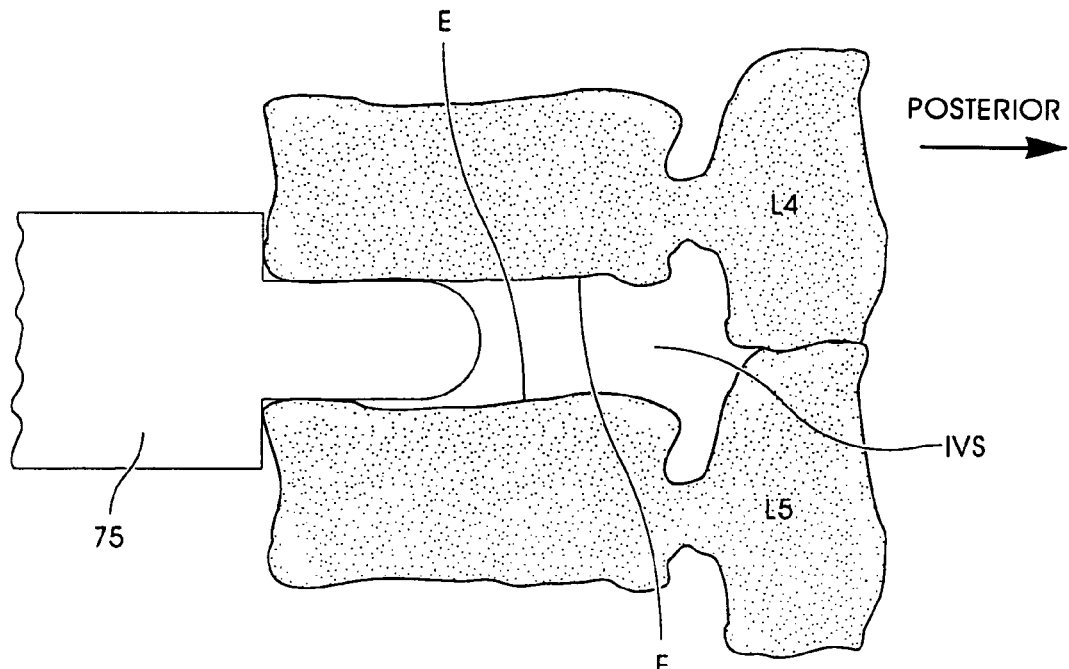
FIG. 10B is a side elevational view of the dilation of a disc space.
Figure 11B:
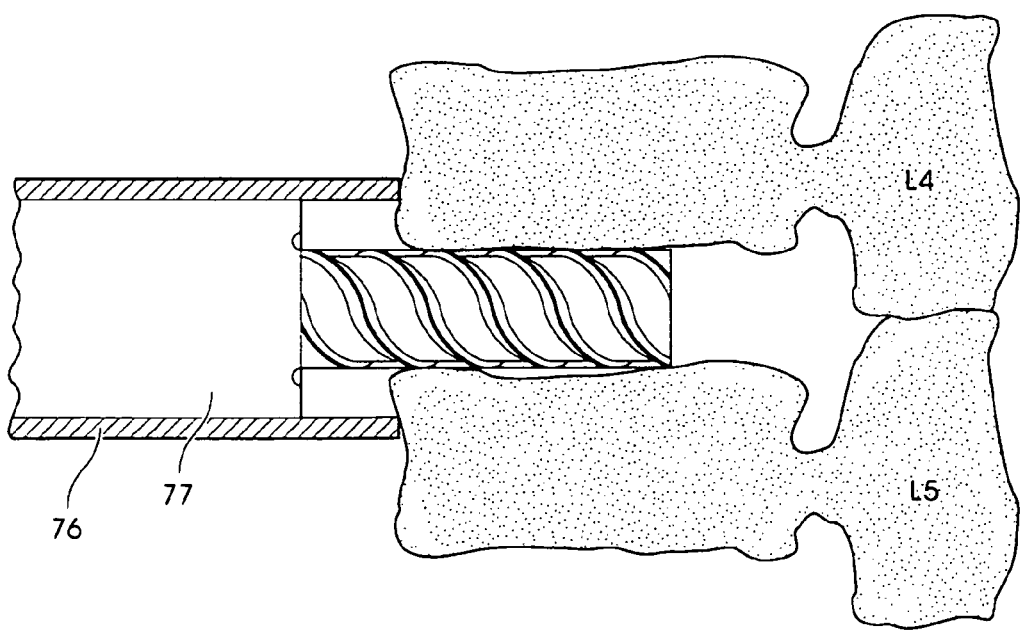
FIG. 11B is a side elevational view showing the outer sleeve in place.
Figure 11A:
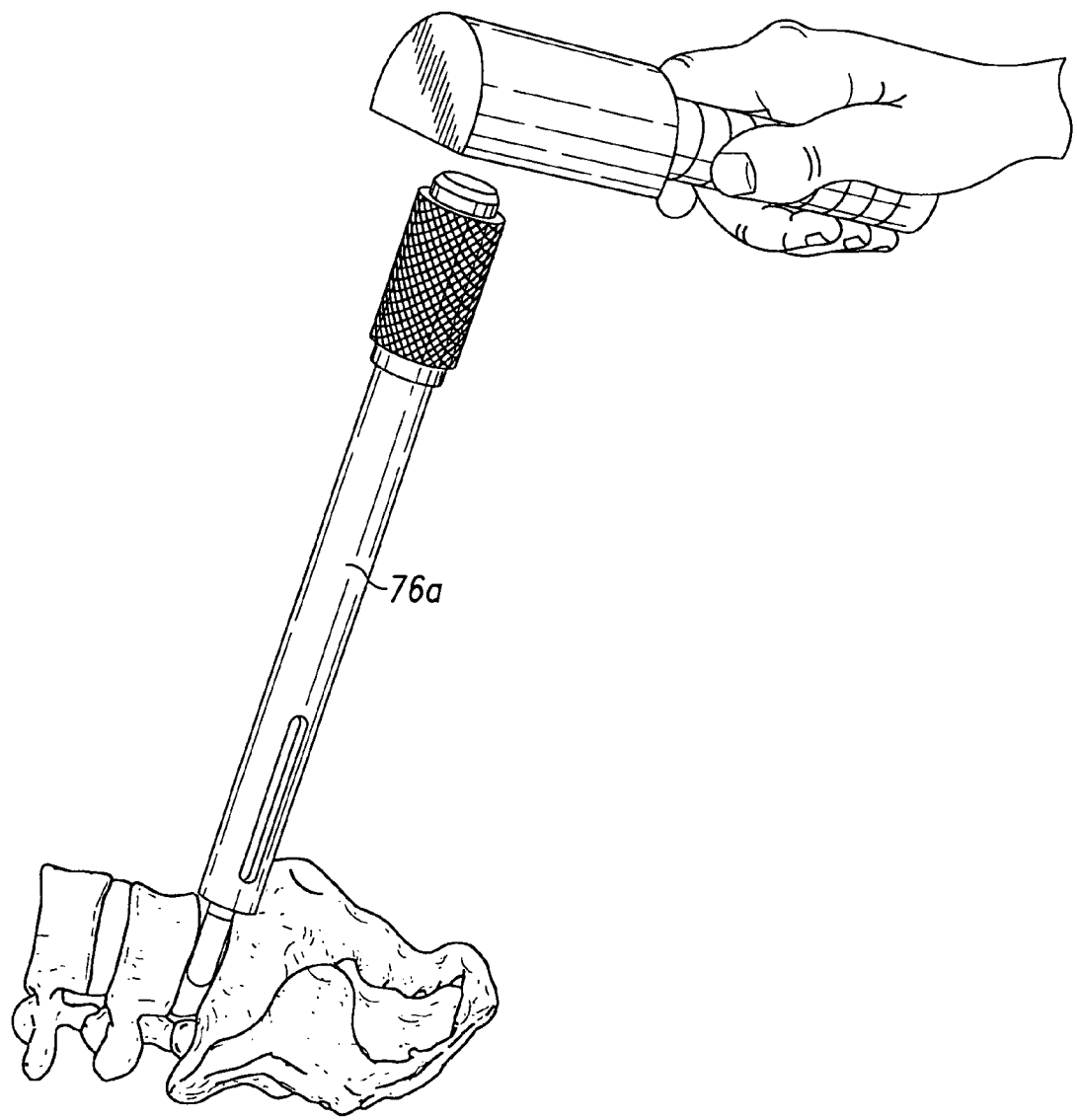
FIG. 11A shows the seating of a single barrel outer sleeve.
Figure 12:
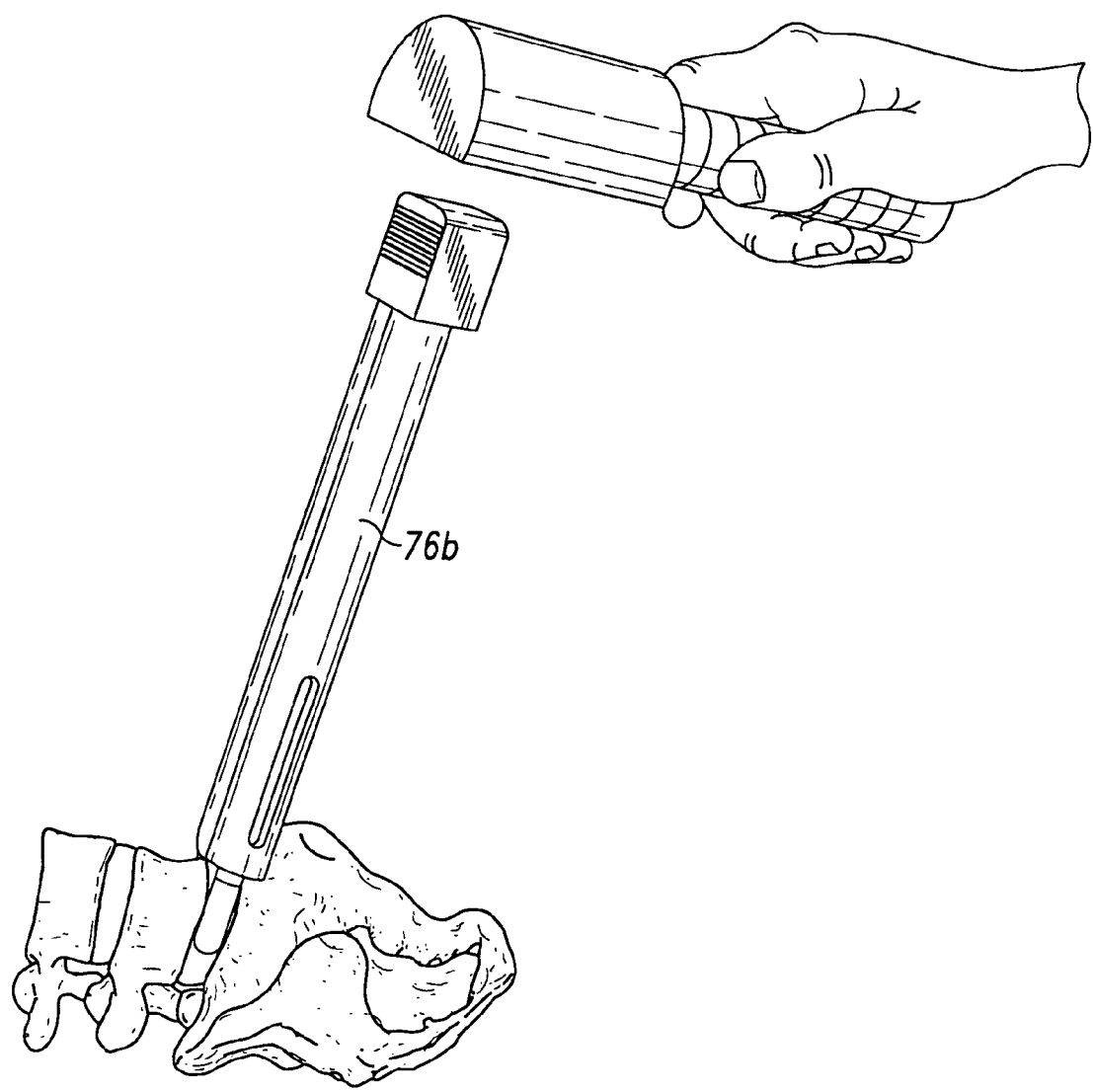
FIG. 12 shows the seating of a double barrel outer sleeve.
Figure 13:
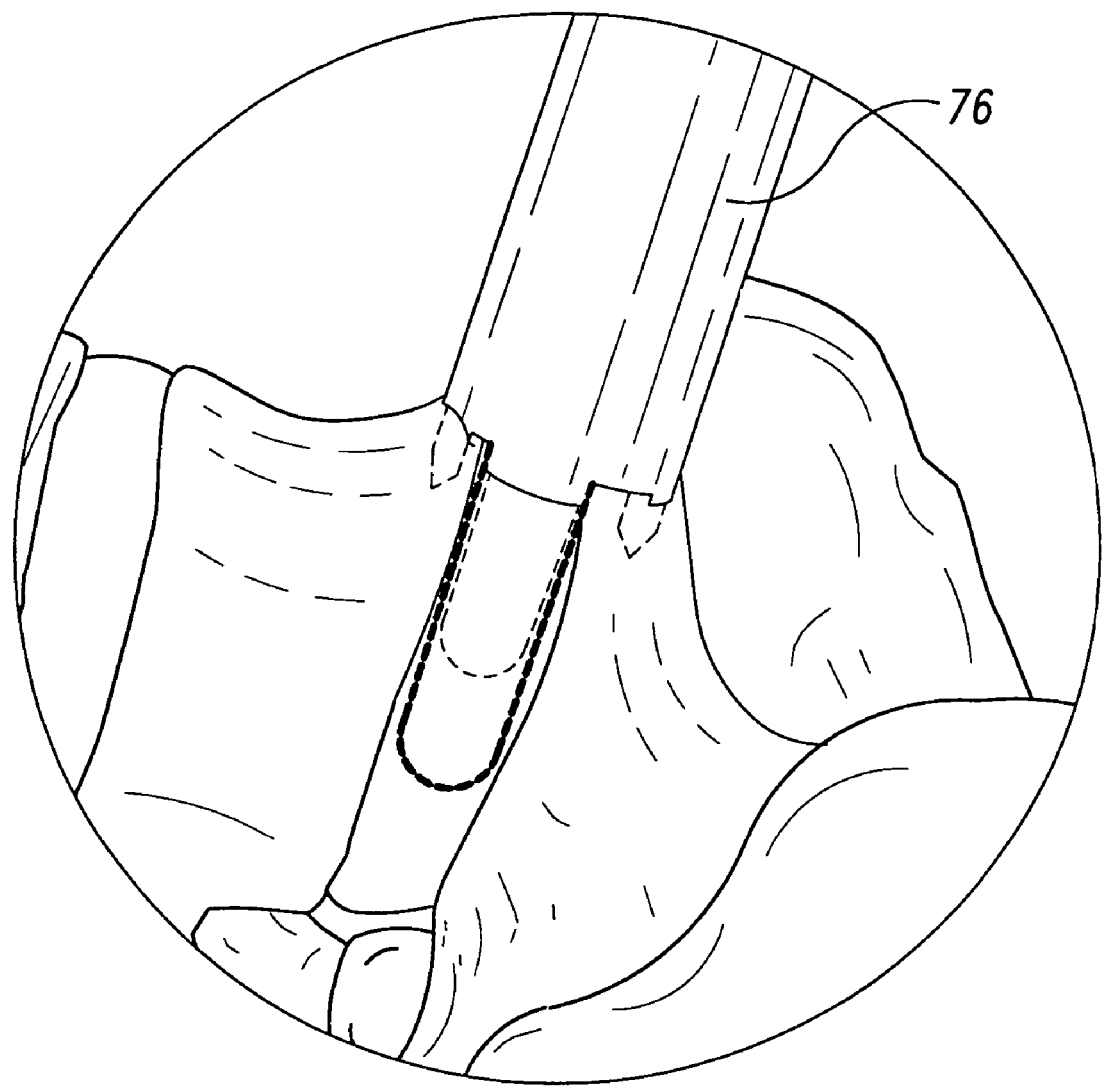
FIG. 13 shows the seating of the outer sleeve.
Figure 14:
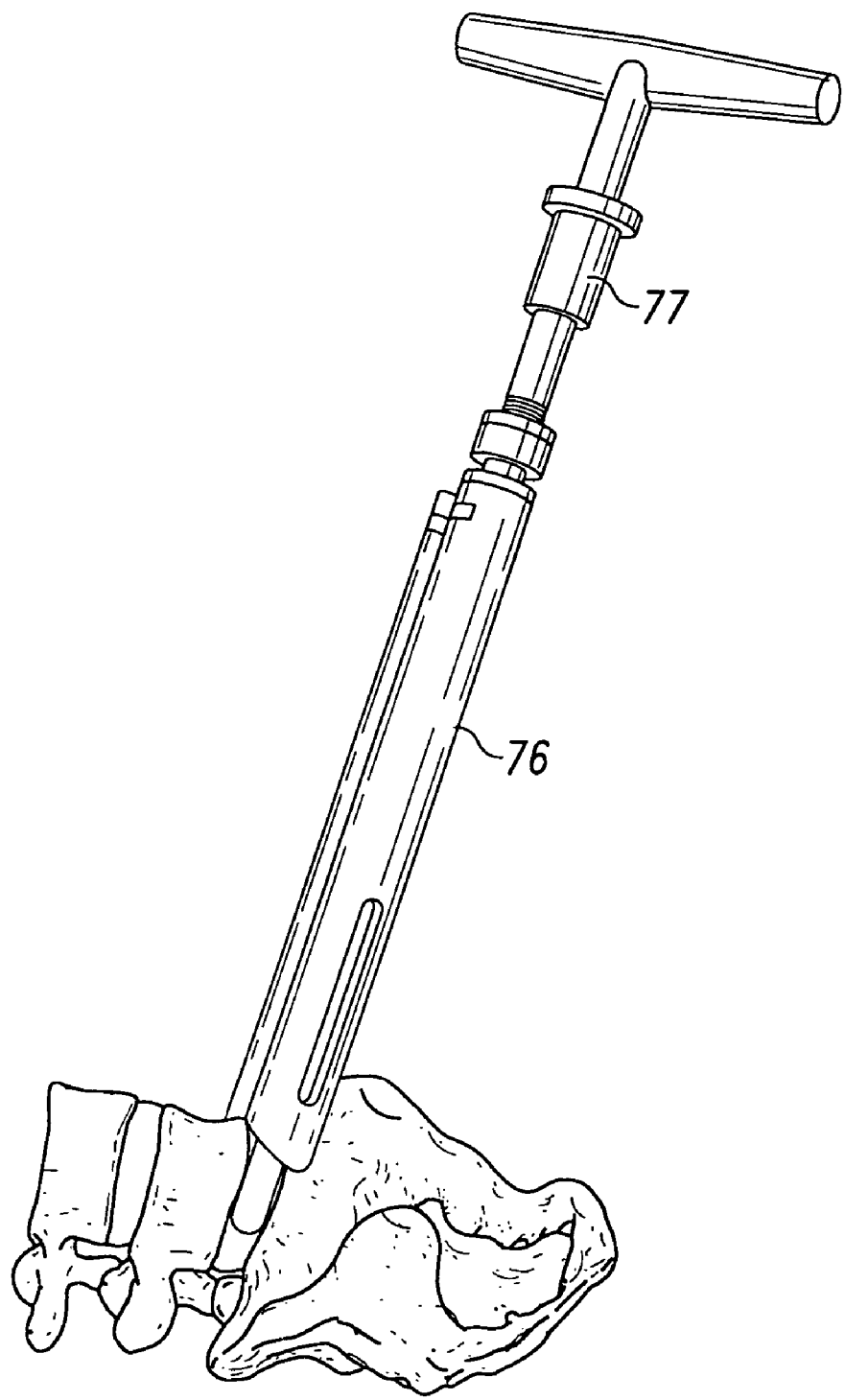
FIG. 14 shows the reaming of the disc space.
Figure 15:
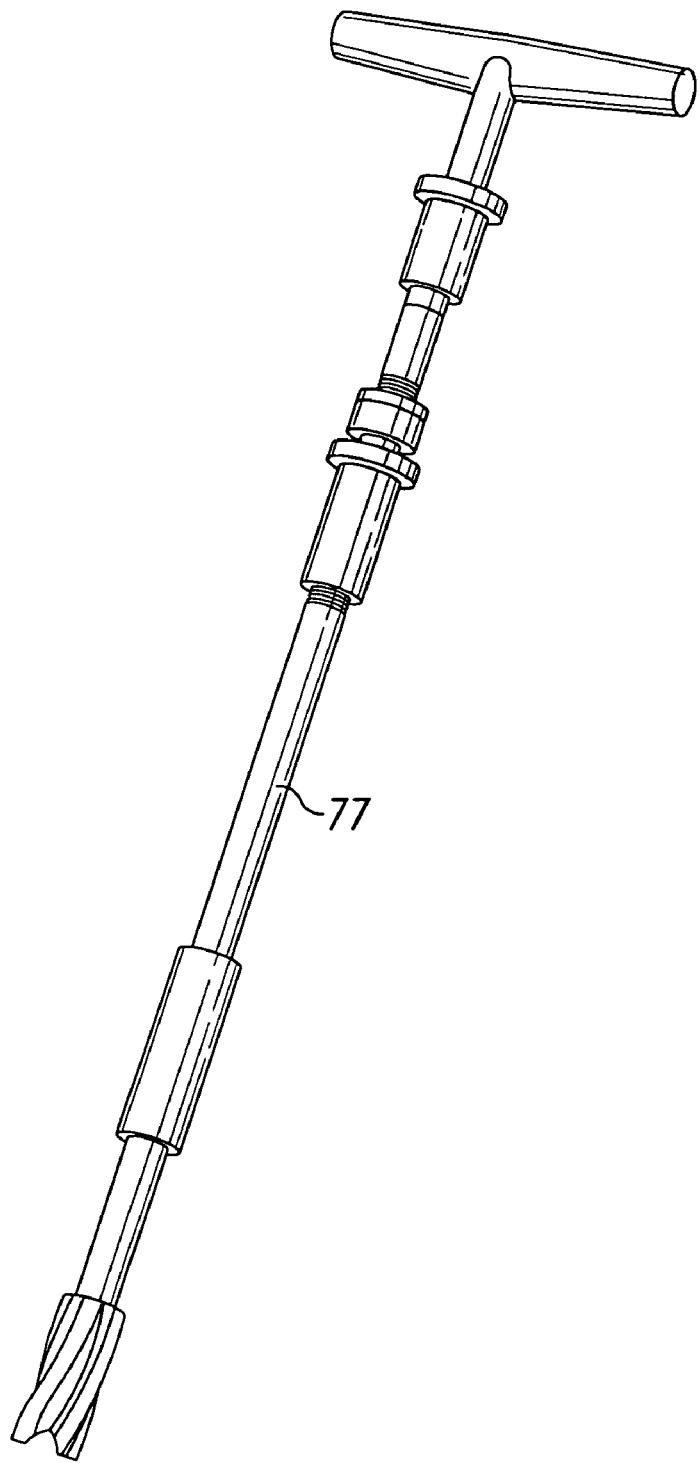
FIG. 15 depicts the reamer used in FIG. 14.
Figure 16:
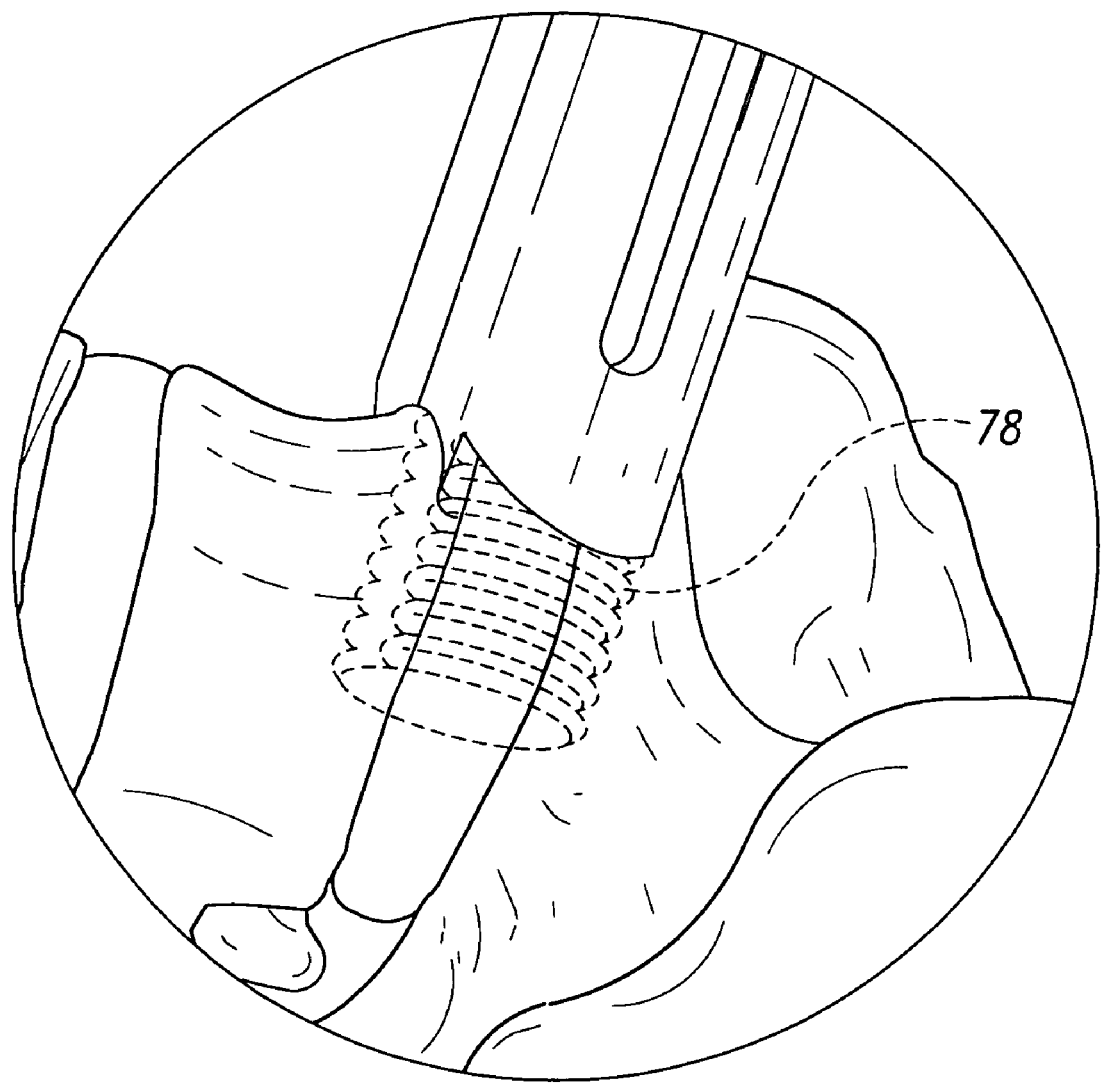
FIG. 16 shows the tapping of the disc space.
Figure 17:
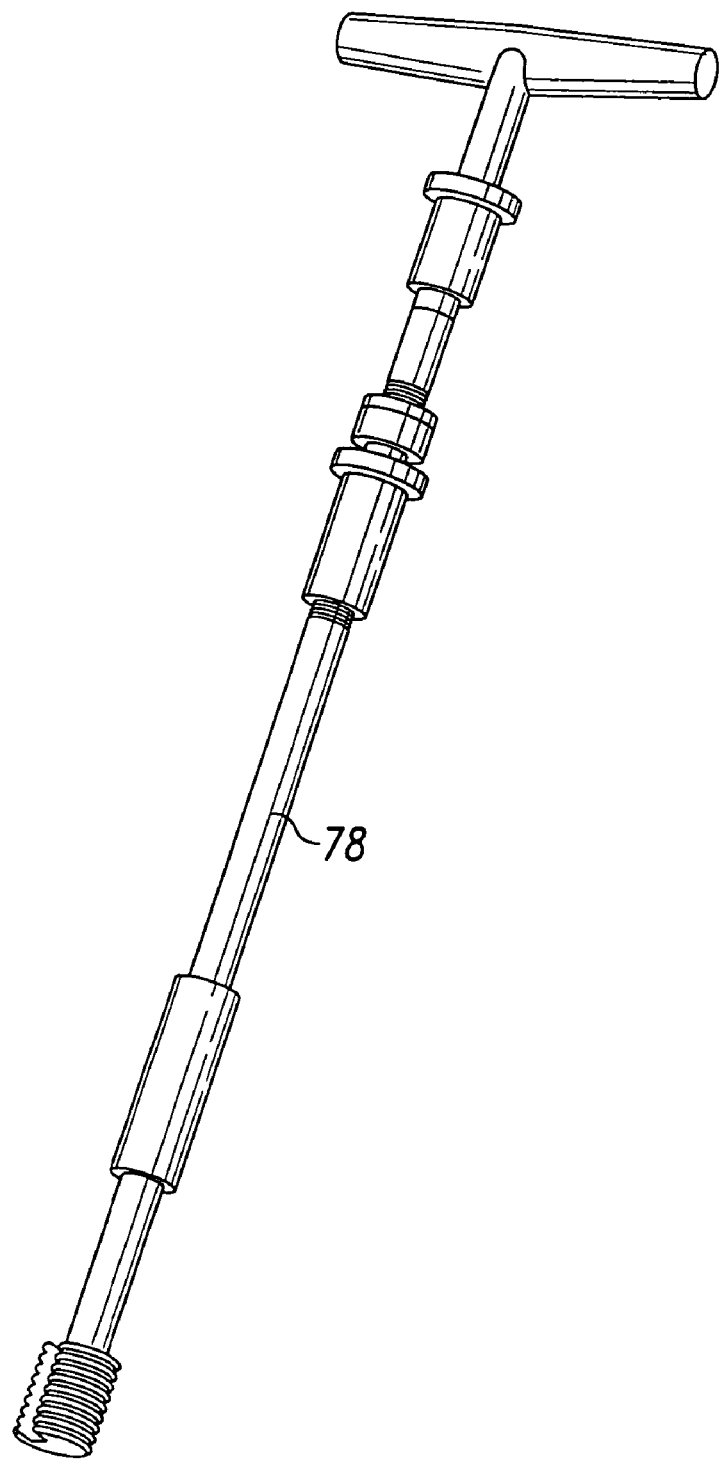
FIG. 17 shows the tap used in FIG. 16.

The spacers of this invention can be inserted using conventional techniques. In accordance with additional aspects of the present invention, methods for implanting an interbody fusion spacer, such as the spacer 40, are contemplated. These methods are also disclosed in commonly assigned, co-pending U.S. patent application Ser. No. 08/604,874, METHODS AND INSTRUMENTS FOR INTERBODY FUSION. As a preliminary step, it is necessary to locate appropriate starting points for implanting the fusion spacer, preferably bilaterally. In the first step of an anterior approach, a distractor 75 is disposed between the vertebral end plates E to dilate the L4-L5 or L5-S1 disc space (FIGS. 10A and 10B). (It is understood, of course, that this procedure can be applied at other vertebral levels). In the second step, shown in FIG. 11A, an outer sleeve 76 is disposed about the disc space IVS. The outer sleeve 76 can be configured to positively engage the anterior aspect of the vertebral bodies to firmly, but temporarily, anchor the outer sleeve 76 in position. In essence, this outer sleeve 76 operates as a working channel for this approach In a preferred embodiment, a single barrel outer sleeve 76a is first inserted (FIG. 11B) followed by a double barrel outer sleeve 76b, (FIG. 12), finally followed by the outer sleeve 76 (FIG. 13). One purpose of this tripartite sleeve system is to provide an enlarged working channel for preparing the vertebrae and implanting the fusion spacer. In the step shown in FIG. 14, a drill or reamer 77 (FIG. 15) is extended through the outer sleeve 76 and used to drill out circular openings in the adjacent vertebral bodies. The openings can be tapped (FIG. 16) with a tap 78 (FIG. 17) to facilitate screw insertion of the fusion spacer 10, although this step is not necessary.

Figure 18:
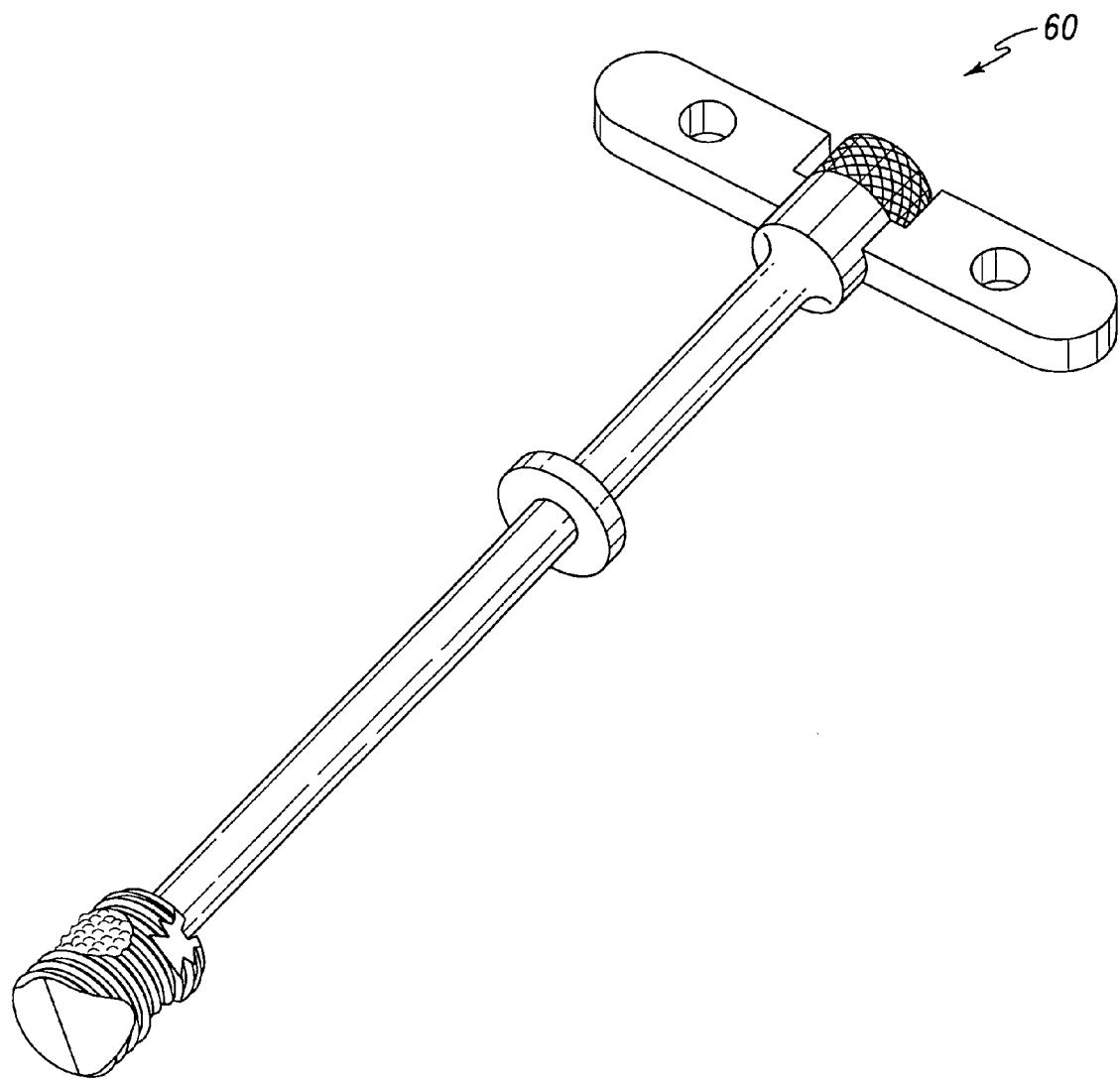
FIG. 18 shows an inserter engaged to a dowel.
Figure 19:
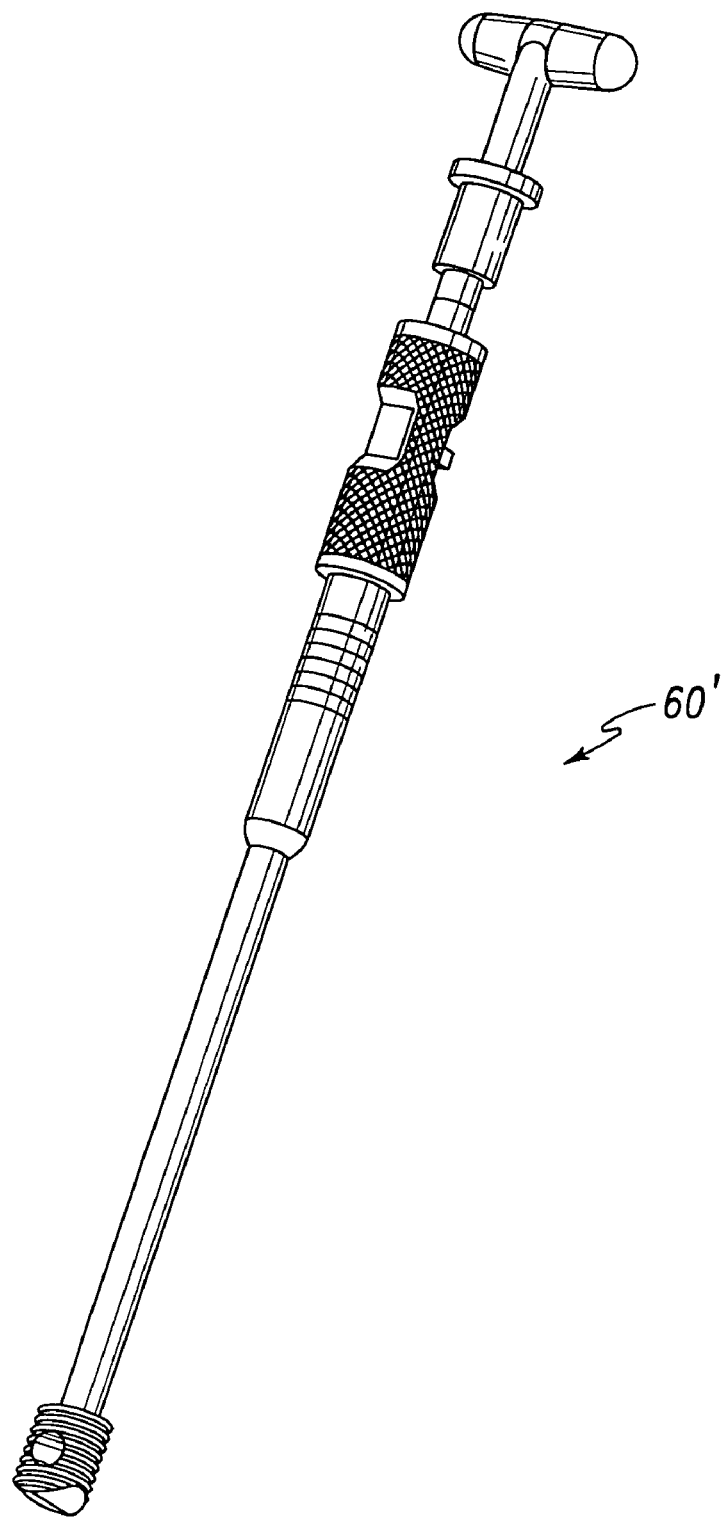
FIG. 19 shows the inserter of FIG. 18 within a sleeve.
Figure 20:
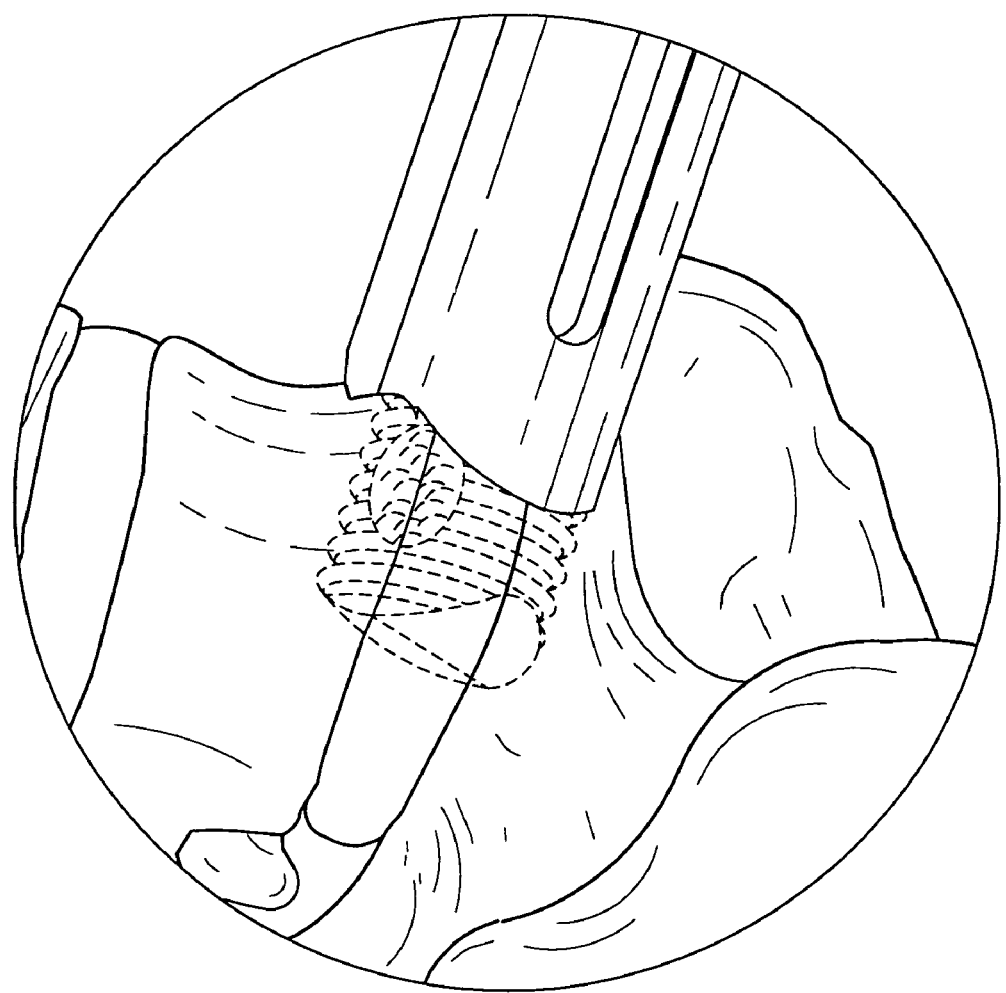
FIG. 20 depicts insertion of a dowel.

The fusion spacer 40 is then engaged by an implant driver 60, 60' (FIGS. 18 & 19) and extended through the outer sleeve 76 as shown in FIG. 13. The spacer is then inserted into the disc space IVS until the initial thread 47 contacts the bone opening as shown in FIG. 20. The implant driver 60 can then be used to screw thread the fusion spacer into the tapped or untapped opening formed in the vertebral and end plate E. Once the dowel 40 is properly positioned, the knob 68 of the tool 60 can be turned to rotate the threaded tip 65 and disengage the tip 65 from the hole 49 of the dowel 40. The inserter 60 and the sleeve 76 can be withdrawn from the surgical site leaving the dowel 40 in place. It is understood that in this step, other suitable driving tools could be used. It can been seen that once implanted, the closed posterior end 26 is directed toward the posterior aspect of the vertebrae. The chamber 25 packed with an osteogenic material is positioned so that the osteogenic material contacts the end plates.

Figure 21:
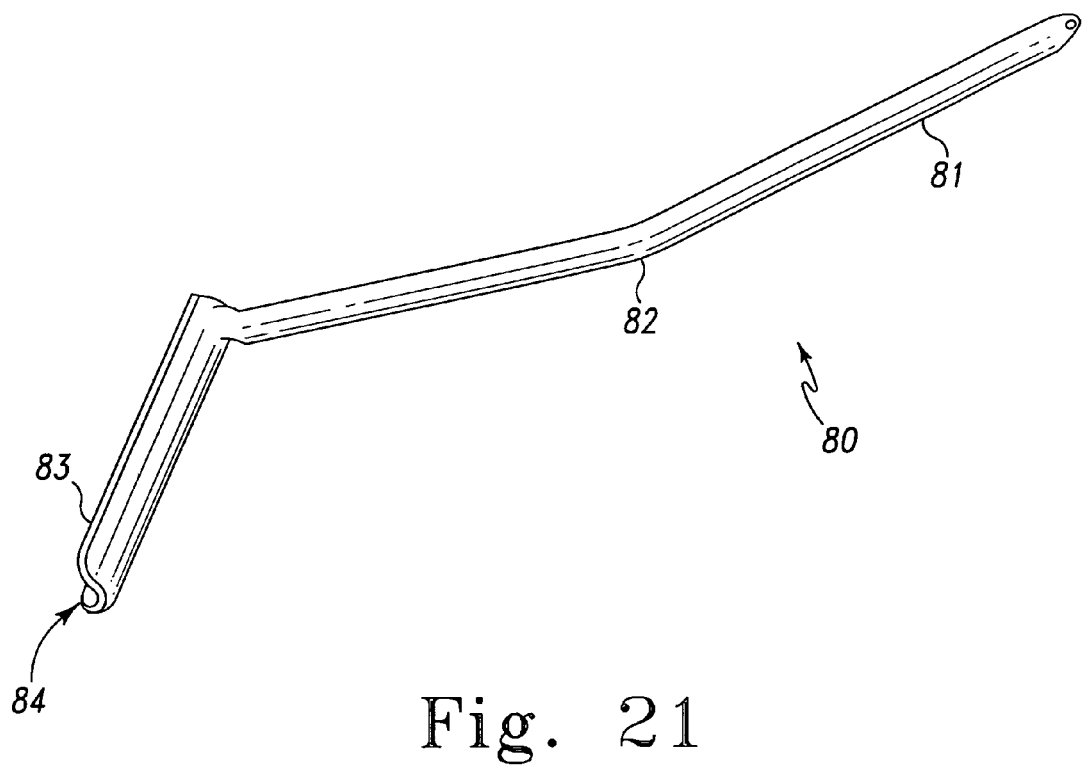
FIG. 21 is a side perspective view of a dural retractor.

The spacers of this invention may also be used with posterior approaches. The steps of the posterior approach are similar to those of the prior anterior approach except that the tools are introduced posteriorly at the instrumented motion segment. This approach may require decortication and removal of vertebral bone to accept the outer sleeve 76. A dural retractor 80 as shown in FIG. 21 may be used to retract and protect the spinal cord and accessory tissues. The retractor 80 includes a handle 81 which preferably includes a bend 82 to facilitate manipulation of the tool. The dural retractor 80 has an end 83 which is attached to the handle portion 81. The end 83 preferably includes a curve 84 which is configured to safely cradle the spinal cord.

Figure 22:
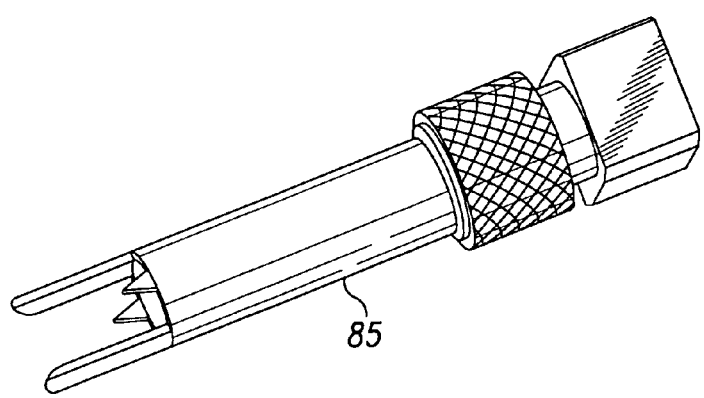
FIG. 22 is a perspective view of a guide protector.
Figure 23:
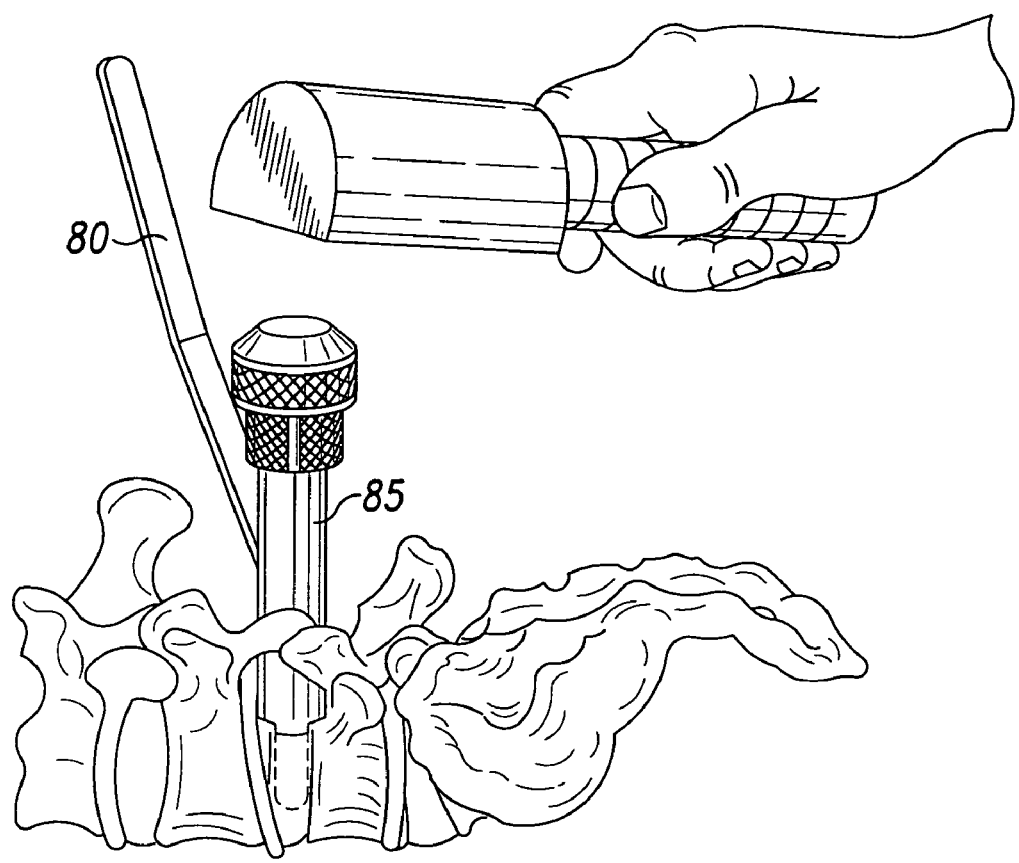
FIG. 23 shows the insertion of the guide protector shown in FIG. 22.

With the spinal cord safely retracted, a seat guide protector 85 (FIG. 22) can be pounded into position as shown in FIG. 23. The seat guide protector 85 can be similar to the sleeve 76 described above. Various tools, such as extractors, reamers and taps can be inserted through the seat guide protector similar as described above. The fusion spacer 40 can be inserted-through the protector 85 into the dilated disc space.

With either the anterior or posterior approaches, the position of the fusion spacer 40 with respect to the adjacent vertebrae can be verified by radiograph or other suitable techniques for establishing the angular relationship between the vertebrae. Alternatively, the preferred depth of insertion of the spacer can be determined in advance and measured from outside the patient as the spacer is positioned between the vertebrae. The depth of insertion of the fusion spacer can be ascertained using depth markings (not shown) on the implant driver 60.

The spacers of this invention can also be inserted using laparoscopic technology as described in Sofamor Danek USA's Laparoscopic Bone Dowel Surgical Technique,© 1995, 1800 Pyramid Place, Memphis, Tenn. 38132, 1-800-933-2635. Devices of this invention can be conveniently incorporated into Sofamor Danek's laparoscopic bone dowel system that facilitates anterior interbody fusions with an approach that is much less surgically morbid than the standard open anterior retroperitoneal approaches. This system includes templates, trephines, dilators, reamers, ports and other devices required for laparoscopic dowel insertion.

Figure 24:
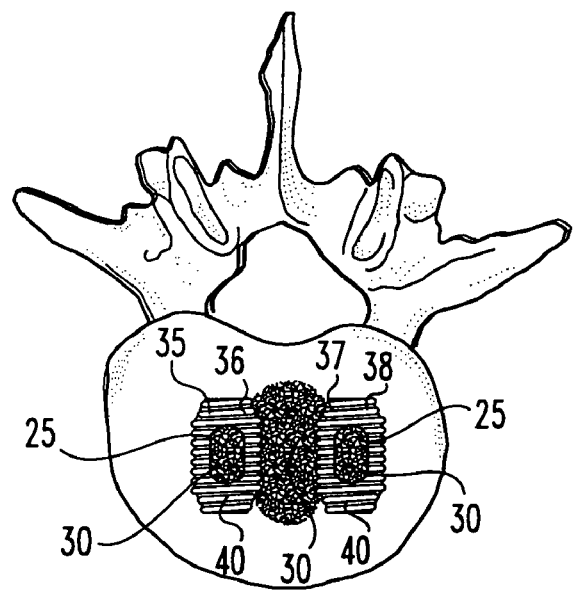
FIG. 24 is a partial cross-section of a spine showing bilateral placement of two dowels.
Figure 25:
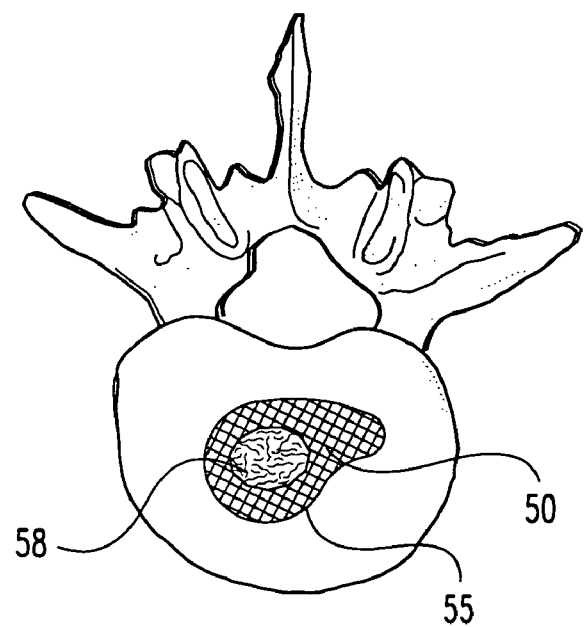
FIG. 25 is a partial cross-section of a spine with a cortical ring implanted.

Bilateral placement of dowels 40 is preferred as shown in FIGS. 2 and 24. This configuration provides a substantial quantity of bone graft available for the fusion. The dual bilateral cortical dowels 40 result in a significant area of cortical bone for load bearing and long-term incorporation via creeping substitution, while giving substantial area for placement of osteogenic autogenous bone and boney bridging across the disc space. Comparing FIG. 24 to FIG. 25, it can be seen that bilateral placement of dowels 40 provides a greater surface area of bone material than a single ring allograft 50 which provides only a single chamber 55 for packing with osteogenic material 30. The dual dowel placement results in two chambers 25 that can be filled with an osteogenic composition. Additionally, osteogenic material 30 such as cancellous bone or BMP in a biodegradable carrier may be packed around the dowels. This provides for the placement of a significant amount of osteogenic material as well as four columns 35, 36, 37, 38 of cortical bone for load bearing.

Figure 26:
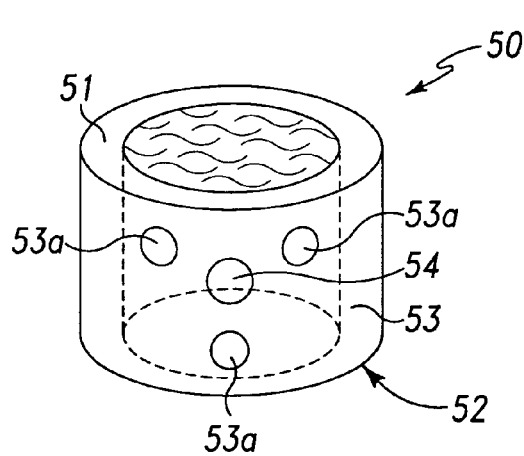
FIG. 26 is a cortical ring packed with an osteogenic material.
Figure 27:
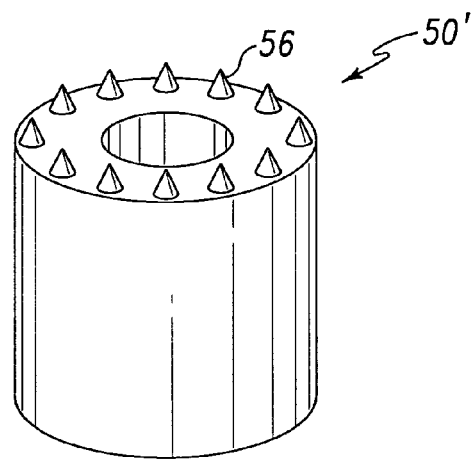
FIG. 27 is yet another cortical ring embodiment provided by this invention.
Figure 28:
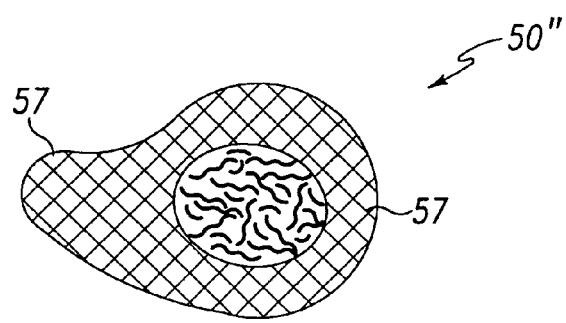
FIG. 28 is another embodiment of a cortical ring provided by this invention.

The load bearing member may also include other grafts such as cortical rings as shown in FIG. 26. Such cortical rings 50 are obtained by a cross-sectional slice of the diaphysis of a long bone and include superior surface 51 and inferior surface 52. The graft shown in FIG. 26 includes an outer surface 53 which is adjacent and between the superior 51 and inferior 52 surfaces. In one embodiment bone growth thru-holes 53a are defined through the outer surface 53 to facilitate fusion. The holes 53a allows mesenchymal stem cells to creep in and BMP protein to diffuse out of the graft. This facilitates bone graft incorporation and possibly accelerates fusion by forming anterior and lateral bone bridging outside and through the device. In another embodiment the outer surface 53 defines a tool engaging hole 54 for receiving an implanting tool. In a preferred embodiment, at least one of the superior and/or inferior surfaces 51,52 are roughened for gripping the end plates of the adjacent vertebrae. The surface roughenings may include teeth 56 on ring 50' as shown in FIG. 27 or waffle pattern 57 as shown on ring 50" in FIG. 28. When cortical rings are used as the graft material the ring 50 may be trimmed for a more uniform geometry as shown in FIG. 26 or left in place as shown in FIG. 28.

Figure 29:
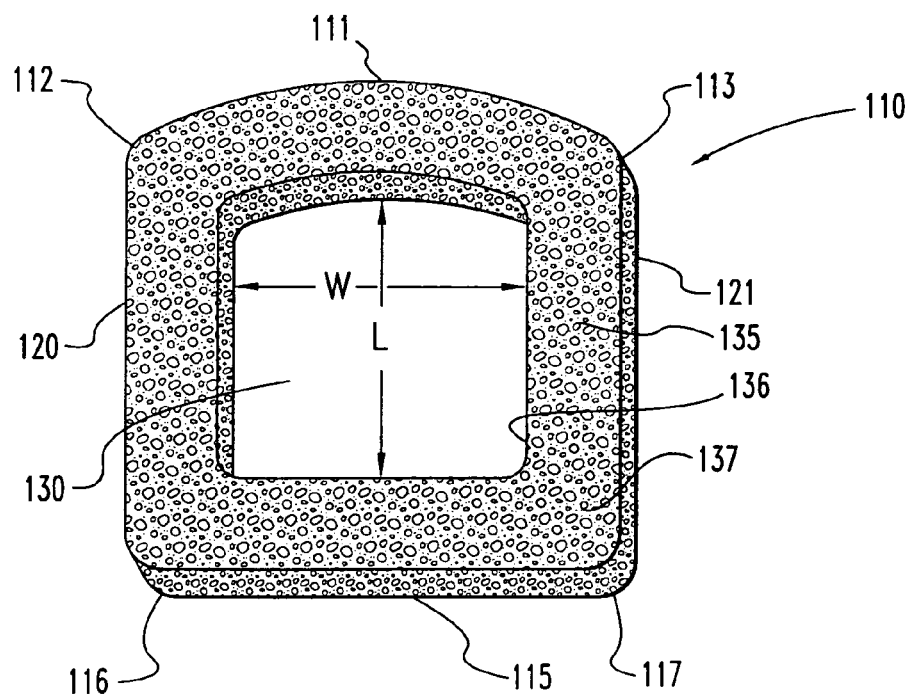
FIG. 29 is a D-shaped spacer of this invention.
Figure 30:
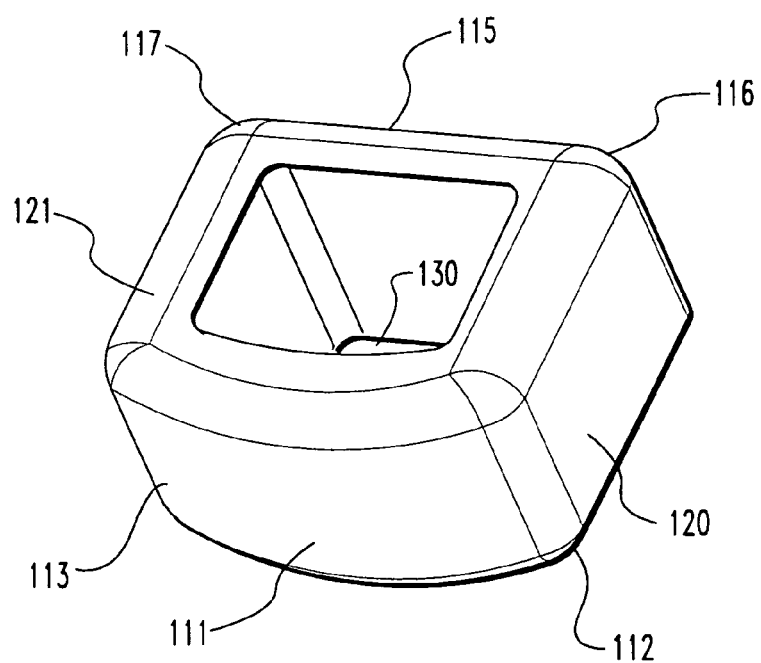
FIG. 30 is a front perspective view of the spacer of FIG. 29.
Figure 31:
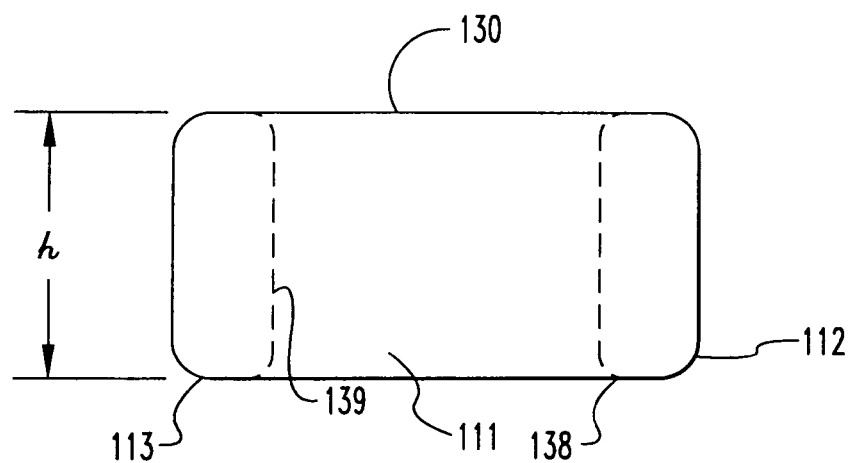
FIG. 31 is a front elevational view of the spacer depicted in FIG. 29.

In another specific embodiment, spacers are provided for engagement between vertebrae as depicted in FIGS. 29-31. Spacers of this invention can be conveniently incorporated into current surgical procedures such as, the Smith-Robinson technique for cervical fusion (Smith, M. D., G. W. and R. A. Robinson, M. D., "The Treatment of Certain Cervical-Spine Disorders By Anterior Removal Of The Intervertebral Disc And Interbody Fusion", *J. Bone And Joint Surgery,* 40-A:607-624 (1958) and Cloward, M. D., R. B., "The Anterior Approach For Removal Of Ruptured Cervical Disks", in meeting of the Harvey Cushing Society, Washington, D.C., Apr. 22, 1958). In such procedures, the surgeon prepares the endplates of the adjacent vertebral bodies to accept a graft after the disc has been removed. The endplates are generally prepared to be parallel surfaces with a high speed burr. The surgeon then typically sculpts the graft to fit tightly between the bone surfaces so that the graft is held by compression between the vertebral bodies. The bone graft is intended to provide structural support and promote bone ingrowth to achieve a solid fusion of the affected joint. The spacers of this invention avoid the need for this graft sculpting as spacers of known size and dimensions are provided. This invention also avoids the need for a donor surgery because the osteoinductive properties of autograft are not required. The spacers can be combined with osteoinductive materials that make allograft osteoinductive. Therefore, the spacers of this invention speed the patient's recovery by reducing surgical time, avoiding a painful donor surgery and inducing quicker fusion.

The spacer 110 includes an anterior wall 111 having opposite ends 112, 113, a posterior wall 115 having opposite ends 116, 117 and two lateral walls 120, 121. Each of the lateral walls 120, 121 is connected between the opposite ends 112, 113, 116, 117 of the anterior 111 and posterior 115 walls to define a chamber 130. The walls are each composed of bone and also include the superior face 135 which defines a first opening 136 in communication with the chamber 130. The superior face 135 includes a first friction or vertebral engaging surface 137. As shown in FIG. 31, the walls further include an opposite inferior face 138 defining a second opening 139 which is in communication with the chamber 130. The chamber 130 is preferably sized to receive an osteogenic composition to facilitate bone growth. The inferior face 138 includes a second friction or second vertebral engaging surface (not shown) which is similar to or identical to the first friction or vertebral engaging surface 137.

In one specific embodiment for an intervertebral disc replacement spacer, a hollow D-shaped spinal spacer is provided. The anterior wall 111 as shown in FIGS. 29-31 is convexly curved. This anterior curvature is preferred to conform to the geometry of the adjacent vertebral bone and specifically to the harder cortical bone of the vertebrae. The D-shape of the spacer 110 also prevents projection of the anterior wall 111 outside the anterior aspect of the disc space, which can be particularly important for spacers implanted in the cervical spine.

Figure 32:
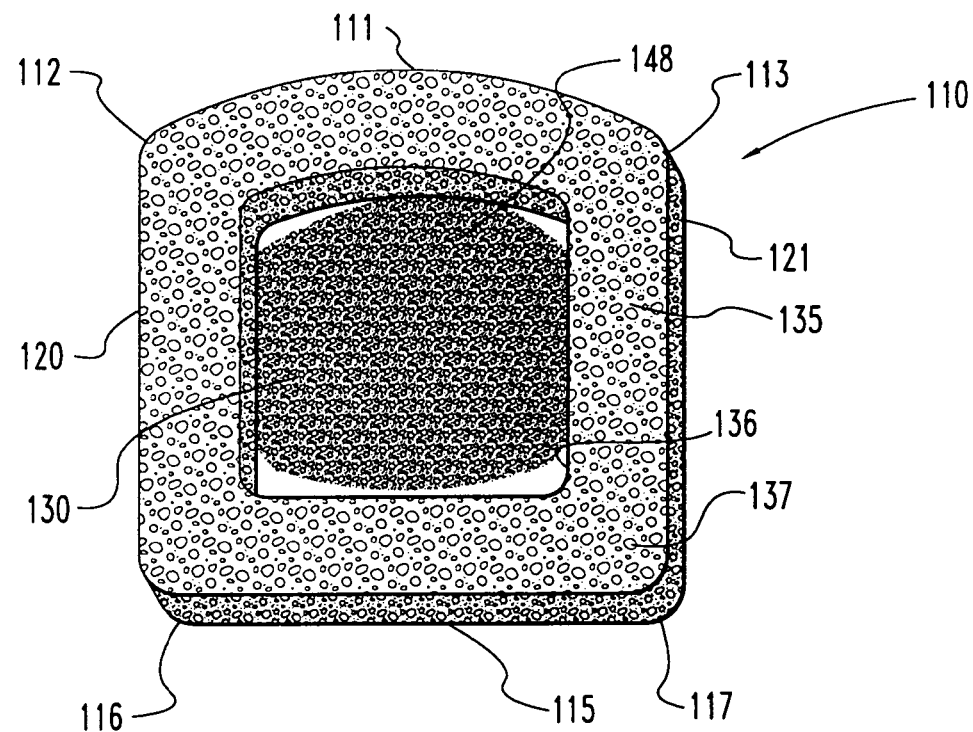
FIG. 32 is a top perspective view of the spacer of FIG. 29 showing the chamber packed with a collagen sponge.
Figure 33:
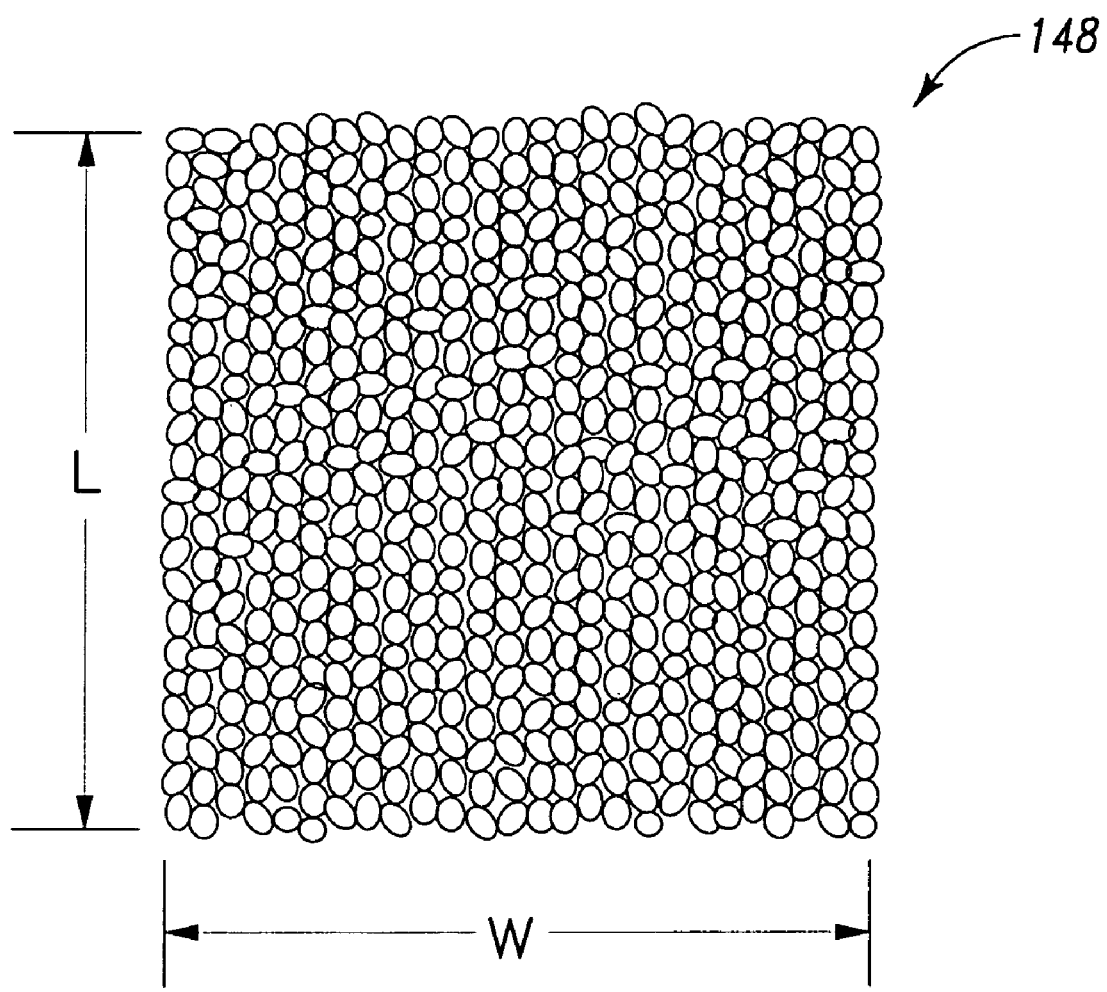
FIG. 33 is a top elevational view of a collagen sponge.

In one specific embodiment shown in FIGS. 32 and 33, the D-shaped spacer 110 includes a collagen sponge 148 having a width w and length l which are each slightly greater than the width W and length L of the chamber. In a preferred embodiment, the sponge 148 is soaked with freeze dried rhBMP-2 reconstituted in buffered physiological saline and then compressed into the chamber 130. The sponge 148 is held within the chamber 130 by the compressive forces provided by the sponge 148 against the walls 111, 115, 120, 121 of the spacer 110.

The spacers are shaped advantageously for cervical arthrodesis. The flat posterior and lateral walls 115, 120 and 121, as shown in FIG. 29, can be easily incorporated into Smith Robinson surgical fusion technique. After partial or total discectomy and distraction of the vertebral space, the surgeon prepares the end plates for the spacer 110 preferably to create flat posterior and lateral edges. The spacer 110 fits snugly with its flat surfaces against the posterior and lateral edges which prevents medial and lateral motion of the spacer 110 into vertebral arteries and nerves. This also advantageously reduces the time required for the surgery by eliminating the trial and error approach to achieving a good fit with bone grafts because the spacers can be provided in predetermined sizes.

Figure 34:
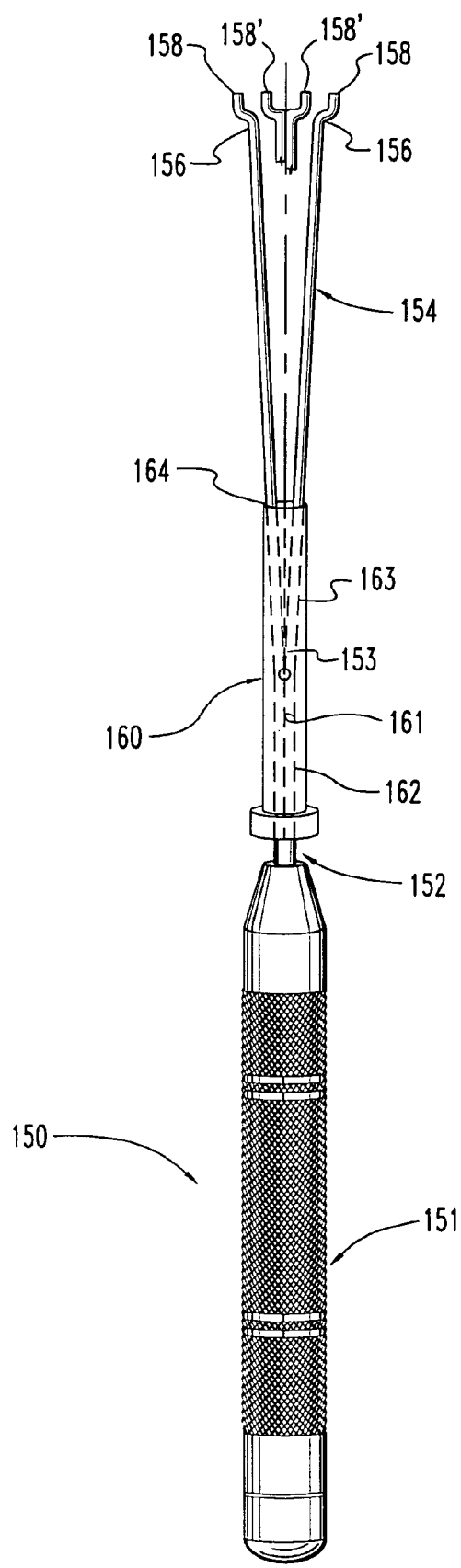
FIG. 34 is an implant insertion device.

Devices such as the spacer 110 or dowel 40, which are not provided with an insertion tool hole, can be inserted into the fusion site during an open or percutaneous surgery using an insertion device such as the one depicted in FIG. 34. The inserter 150 includes a handle 151 with knurlings or other suitable patterns to enhance manual gripping of the handle. A shaft 152 extends from the handle 151 and is generally divided into two portions: a solid portion 153 and a split jaw portion 154. The split jaw portion 154 is at the distal end of the shaft 152 opposite the handle 151. In the preferred embodiment, the split jaw portion 154 includes two jaws 156 each having an offset gripping surface 158 at their free ends. As depicted in FIG. 34 the split jaw portions 154 are movable from a fully opened position as represented by the fully separated position of the gripping surfaces 158. The split jaw portion 154 is closeable to a fully closed position in which the two jaws 156 are in contact with one another. In the fully closed position, the gripping surfaces, identified as 158' in FIG. 34, are separated by a distance sufficiently close to grip a hollow spacer 110 therebetween. In particular, the closed gripping surfaces 158' contact the side surfaces of the two lateral walls 120, 121 of the spacer 110. In one preferred embodiment, the gripping surfaces 158 are roughened or knurled to enhance the grip on the spacer 110.

The inserter 150 further includes a sleeve 160 that is concentrically disposed around shaft 152. Preferably the sleeve 160 defines an inner bore 161 with a first portion 162 having a diameter slightly greater than the diameter of shaft 152. The internal bore 161 includes a flared portion 163 at its distal end 164. In the preferred embodiment, when the jaws 156 of the split jaw portion 154 are in their fully opened position, the jaws contact the flared portion 63 of the bore 161.

In the use of the inserter 150, the sleeve 160 is slid along the shaft 152, and more particularly along the opened jaws 156, to push the jaws together. As the jaws are pushed together, the gripping surfaces 158 engage and firmly grip a spacer 110 as described above. This inserter can then be extended percutaneously into the surgical site to implant a spacer 110 in the intra-discal space. Once the spacer is properly positioned, the sleeve 160 can be moved back toward the handle 151, so that the natural resilience of the two jaws 156 cause them to spread apart, thereby releasing the spacer 110. The inserter 150 can then be withdrawn from the surgical site with the jaws fully opened, or the sleeve can be advanced along the shaft once the gripping surfaces 158 have cleared the spacer 110. Other details of a similar device are disclosed in commonly assigned, pending U.S. application Ser. No. 08/697,784, IMPLANT INSERTION DEVICE. Metal spacers, insertion devices and methods relating to the same are disclosed in commonly assigned and co-pending applications: U.S. patent application Ser. No. 08/603,675, VERTEBRAL SPACER and U.S. patent application Ser. No. 08/603,676, INTERVERTEBRAL SPACER.

Figure 9:
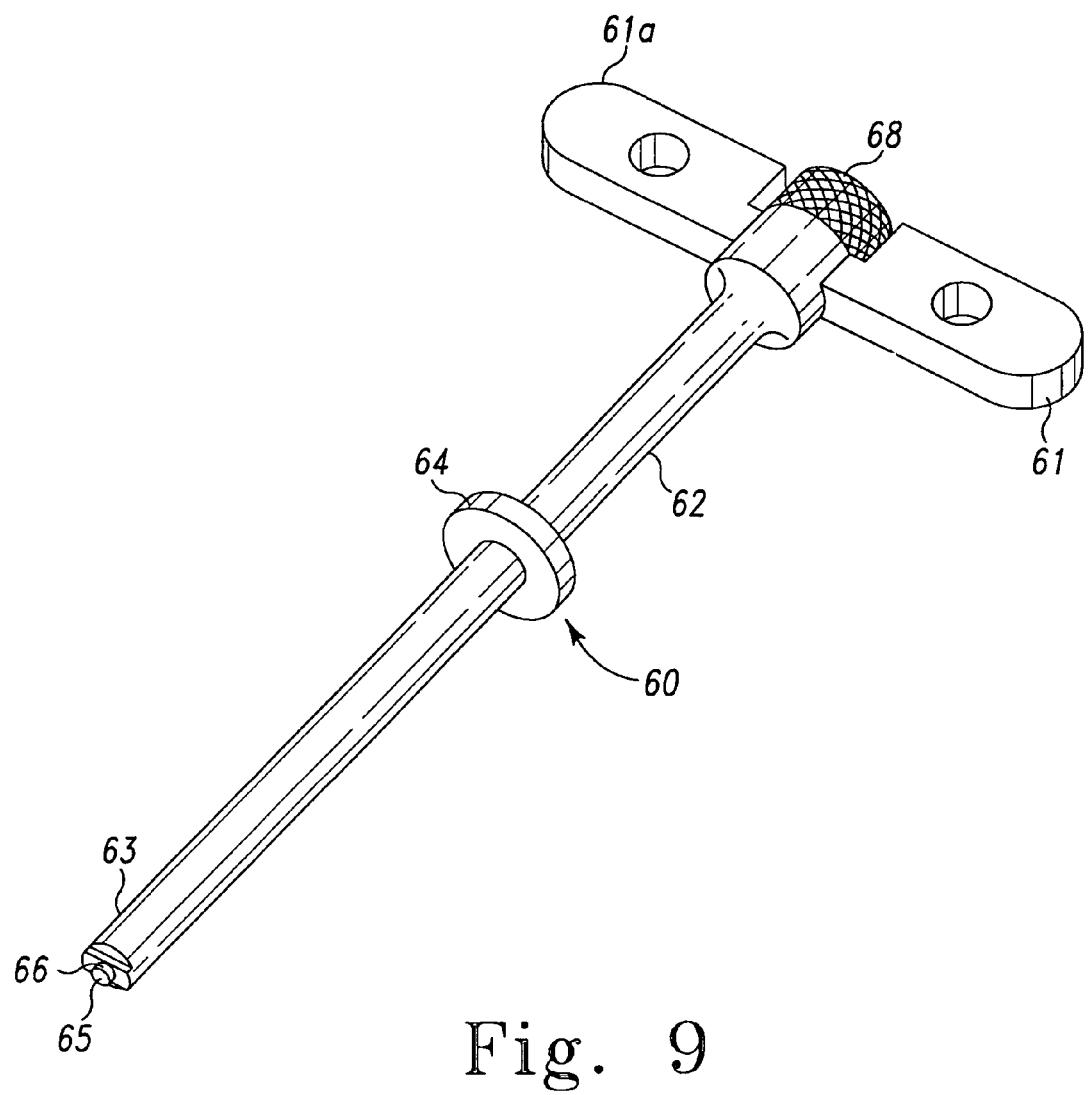
FIG. 9 is an insertion device for inserting the spacers of this invention.
Figure 35:
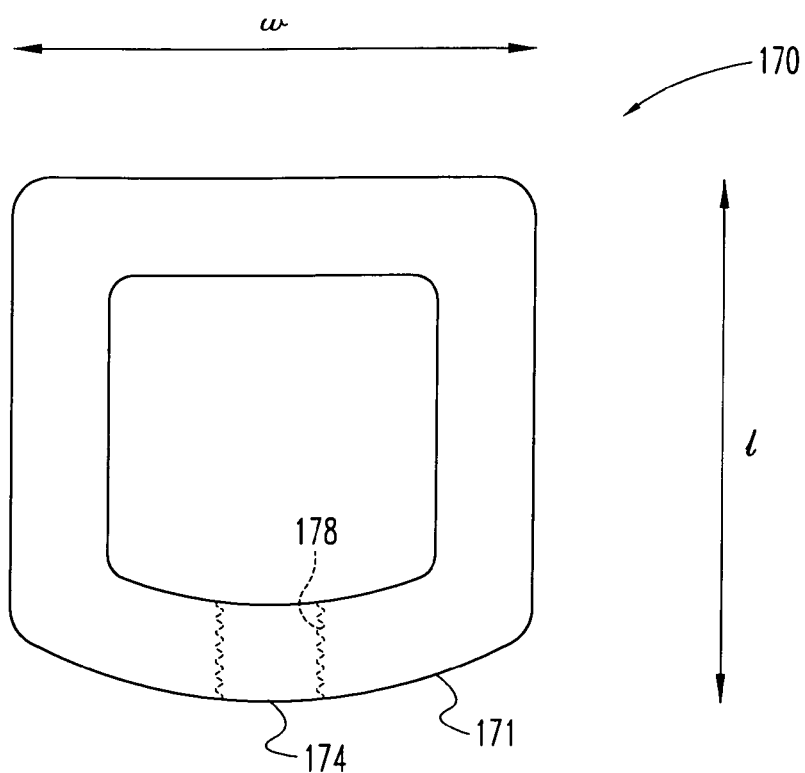
FIG. 35 is a D-spaced spacer of this invention having a tool engaging hole.
Figure 36:
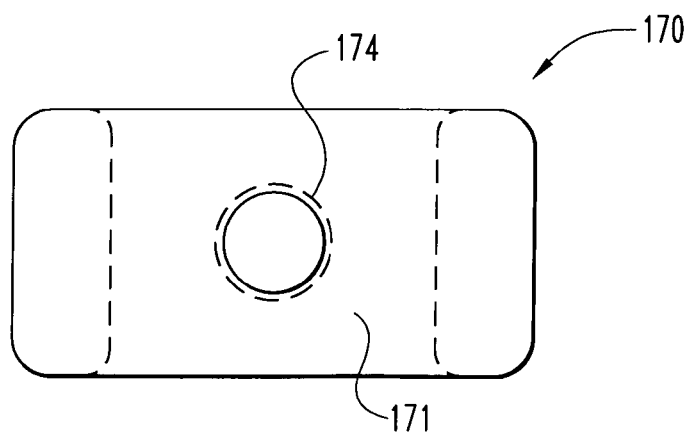
FIG. 36 is a front elevational view of the spacer FIG. 35.
Figure 37:
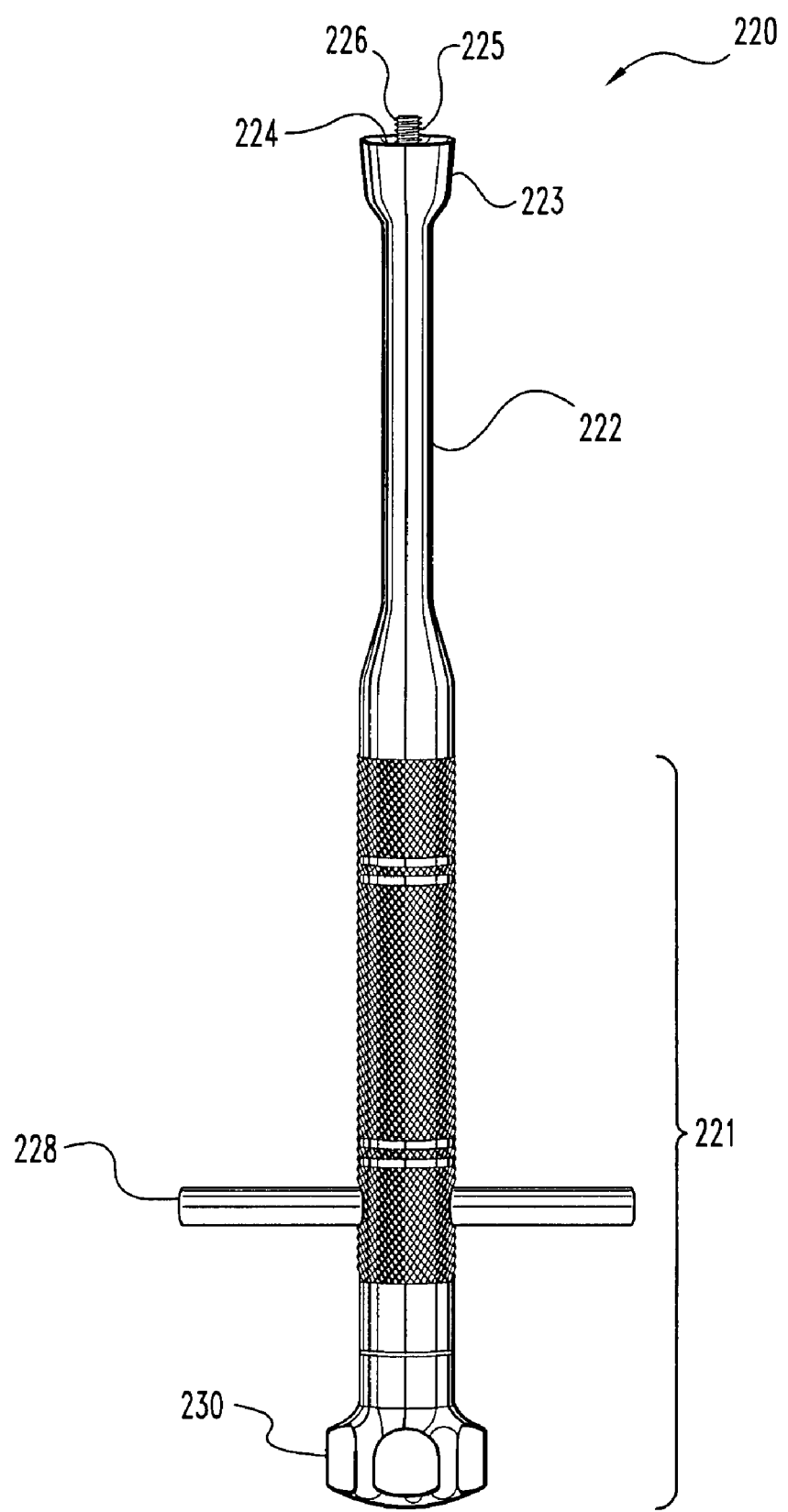
FIG. 37 depicts a perspective view of an implanting tool.

Alternatively, the spacers of this invention may be provided with a tool engaging hole for insertion of a tool, such as the tool depicted in FIG. 9. According to another specific embodiment depicted in FIGS. 35 and 36, the spacer 170 includes an anterior wall 171 defining a tool engaging hole 174. In a most preferred embodiment, the tool engaging hole 174 is threaded for receiving a threaded implanting tool such as depicted in FIG. 37. The inserter 220 includes a handle portion 221 with knurlings or other suitable patterns to enhance manual gripping of the handle. A shaft 222 extends from the handle 221. The distal end 223 of the shaft 222 includes a tip 225 which mates with the tool engaging hole 174. Preferably the tip 225 and tool engaging hole 174 have corresponding mating threads 226, 178. Where the tool engaging hole 174 is defined in a curved wall as shown in FIG. 35, the distal end 223 of the shaft 222 preferably includes a curved portion 224 that conforms to the curved anterior surface of the spacer. The inserter 220 also preferably includes a T-handle 228 for spacer control and positioning. Preferably the inserter 120 includes means for rotating the threaded tip 225. In FIG. 37, the knob 230 is engaged to the tip 225 via an inner shaft extending through an internal bore (not shown) in the handle 221 and shaft 222. The tip 225 is preferably at the end of the inner shaft with the inner shaft rotatingly mounted within the handle 221 and shaft 222.

In the use of the inserter 220, a spacer 170 is engaged to the threaded tip 225 with the curved portion 224 flush with the anterior wall 171. The inserter and spacer can then be extended percutaneously into the surgical site to implant the spacer in the intra-discal space. Once the spacer 170 is properly positioned, the knob 230 can be turned to rotate the threaded tip 225 and disengage the tip from the hole 174 of the spacer 110. The inserter 220 can then be withdrawn from the surgical site leaving the spacer 170 in place.

Figure 38:
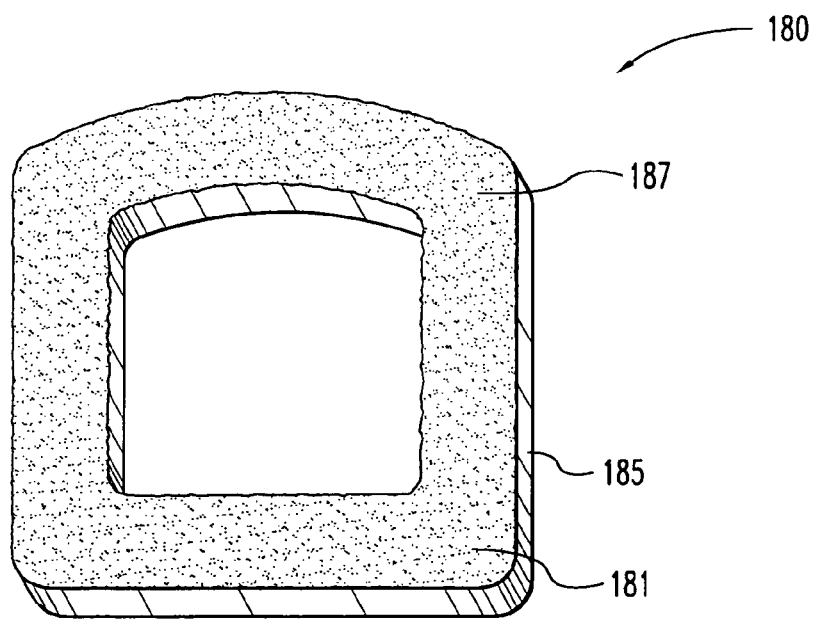
FIG. 38 is top elevational view of another embodiment of the spacer.
Figure 39:
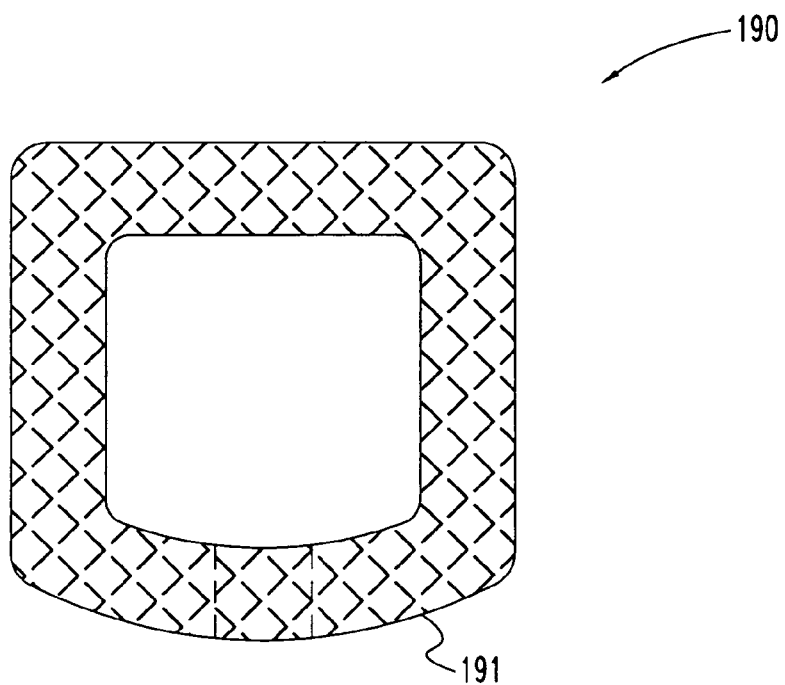
FIG. 39 is a top elevational view of another embodiment of the spacer.
Figure 40:
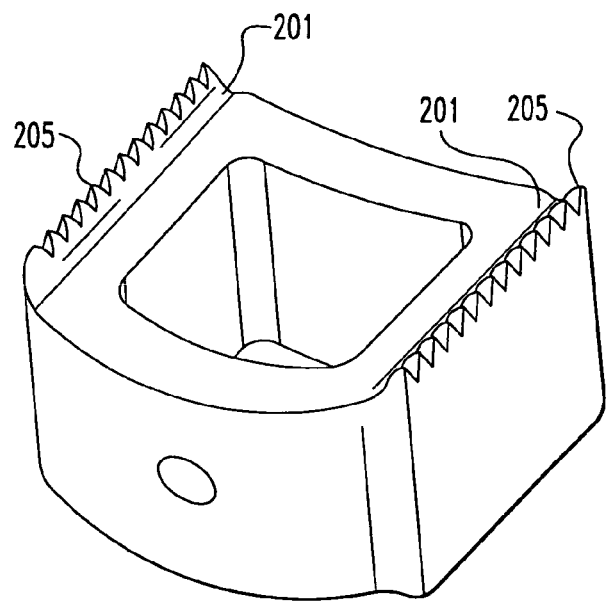
FIG. 40 is a top perspective view of another embodiment of the spacers of this invention having teeth.
Figure 41:
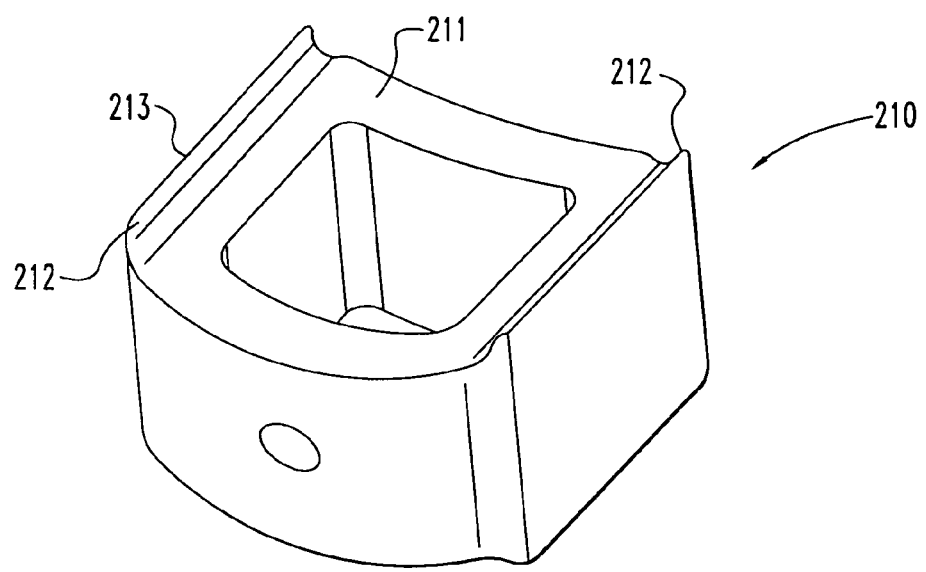
FIG. 41 is a perspective view of another embodiment of the spacer having blades.
Figure 42:
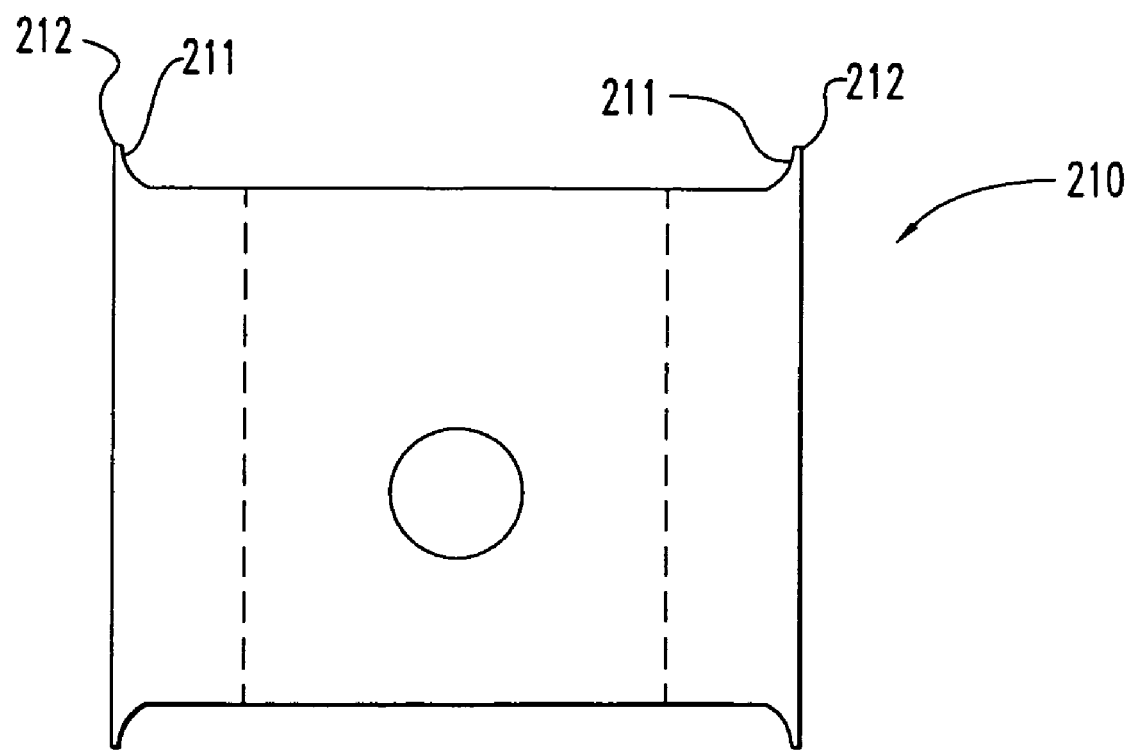
FIG. 42 is a front elevational view of the spacer of FIG. 41.

In preferred embodiments, the engaging surfaces of the spacers are machined to facilitate engagement with the endplates of the vertebrae and prevent slippage of the spacer as is sometimes seen with smooth graft prepared at the time of surgery. The spacer 180 may be provided with a roughened surface 181 on one of the engaging surfaces 187 of one or both of the superior face 185 or inferior face (not shown) as shown in FIG. 38. The roughened surface 191 of the spacer 190 may include a waffle or other suitable pattern as depicted in FIG. 39. In one preferred embodiment shown in FIG. 40, the engaging surfaces 201 include teeth 205 which provide biting engagement with the endplates of the vertebrae. In another embodiment (FIGS. 41 and 42), the spacer 210 includes engaging surfaces 211 machined to include one or more blades 212. Each blade includes a cutting edge 213 configured to pierce a vertebral end-plate. The blade 212 can be driven into the bone surface to increase the initial stability of the spacer.

Figure 43:
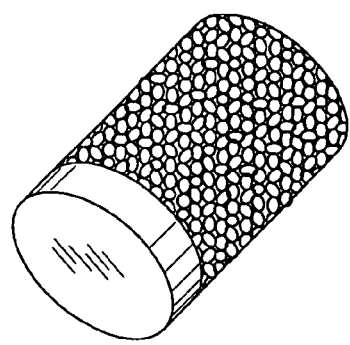
FIG. 43 is a perspective view of an autograft Crock dowel.
Figure 44:
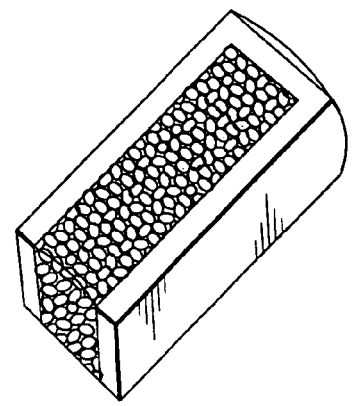
FIG. 44 is a perspective view of an autograft tricortical dowel.
Figure 45:
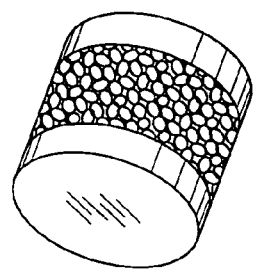
FIG. 45 is a perspective view of an autograft button dowel.
Figure 46:
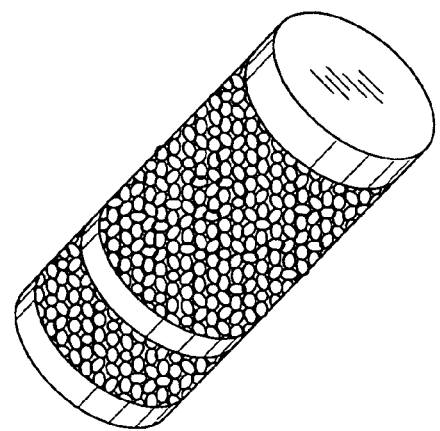
FIG. 46 is a perspective view of a hybrid autograft button/allograft Crock dowel.

Any suitable load bearing member which can be synergistically combined with an osteogenic composition is contemplated. Other potential load bearing members include allograft Crock dowels (FIG. 43), tricortial dowels (FIG. 44), button dowels (FIG. 45) and hybrid allograft button-allograft crock dowels (FIG. 46).

Figure 47:
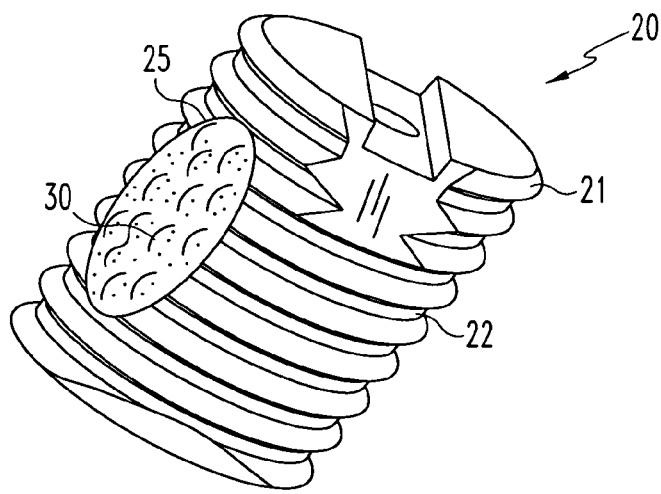
FIG. 47 is a perspective view of a threaded cortical threaded diaphysial dowel having an osteogenic composition packed in the chamber.

An osteogenic material can be applied to the spacers of this invention by packing the chamber 25,130 with an osteogenic material 30, 148 as shown in FIGS. 32 and 47, by impregnating the graft with a solution including an osteogenic composition or by both methods combined. The composition may be applied by the surgeon during surgery or the spacer may be supplied with the composition preapplied. In such cases, the osteogenic composition may be stabilized for transport and storage such as by freeze-drying. The stabilized composition can be rehydrated and/or reactivated with a sterile fluid such as saline or water or with body fluids applied before or after implantation. Any suitable osteogenic material or composition is contemplated, including autograft, allograft, xenograft, demineralized bone, synthetic and natural bone graft substitutes, such as bioceramics and polymers, and osteoinductive factors. The term osteogenic composition used here means virtually any material that promotes bone growth or healing including natural, synthetic and recombinant proteins, hormones and the like.

Autograft can be harvested from locations such as the iliac crest using drills, gouges, curettes and trephines and other tools and methods which are well known to surgeons in this field. Preferably, autograft is harvested from the iliac crest with a minimally invasive donor surgery. The graft may include osteocytes or other bone reamed away by the surgeon while preparing the end plates for the spacer.

Advantageously, where autograft is chosen as the osteogenic material, only a very small amount of bone material is needed to pack the chamber 130. The autograft itself is not required to provide structural support as this is provided by the spacer 110. The donor surgery for such a small amount of bone is less invasive and better tolerated by the patient. There is usually little need for muscle dissection in obtaining such small amounts of bone. The present invention therefore eliminates many of the disadvantages of autograft.

The osteogenic compositions used in this invention preferably comprise a therapeutically effective amount of a substantially pure bone inductive factor such as a bone morphogenetic protein in a pharmaceutically acceptable carrier. The preferred osteoinductive factors are the recombinant human bone morphogenic proteins (rhBMPs) because they are available in unlimited supply and do not transmit infectious diseases. Most preferably, the bone morphogenetic protein is a rhBMP-2, rhBMP-4 or heterodimers thereof. The concentration of rhBMP-2 is generally between about 0.4 mg/ml to about 1.5 mg/ml, preferably near 1.5 mg/ml. However, any bone morphogenetic protein is contemplated including bone morphogenetic proteins designated as BMP-1 through BMP-13. BMPs are available from Genetics Institute, Inc., Cambridge, Mass. and may also be prepared by one skilled in the art as described in U.S. Pat. Nos. 5,187,076 to Wozney et al.; 5,366,875 to Wozney et al.; 4,877,864 to Wang et al.; 5,108, 922 to Wang et al.; 5,116,738 to Wang et al.; 5,013,649 to Wang et al.; 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenic protein from bone are described in U.S. Pat. No. 4,294,753 to Urist and Urist et al., 81 PNAS 371, 1984.

The choice of carrier material for the osteogenic composition is based on biocompatibility, biodegradability, mechanical properties and interface properties as well as the structure of the load bearing member. The particular application of the compositions of the invention will define the appropriate formulation. Potential carriers include calcium sulphates, polylactic acids, polyanhydrides, collagen, calcium phosphates, polymeric acrylic esters and demineralized bone. The carrier may be any suitable carrier capable of delivering the proteins. Most preferably, the carrier is capable of being eventually resorbed into the body. One preferred carrier is an absorbable collagen sponge marketed by Integra Life-Sciences Corporation under the trade name Helistat® Absorbable Collagen Hemostatic Agent. Another preferred carrier is an open cell polylactic acid polymer (OPLA). Other potential matrices for the compositions may be biodegradable and chemically defined calcium sulfates, calcium phosphates such as tricalcium phosphate (TCP) and hydroxyapatite (HA) and including injectable bicalcium phosphates (BCP), and polyanhydrides. Other potential materials are biodegradable and biologically derived, such as bone or dermal collagen. Further matrices are comprised of pure proteins or extracellular matrix components. The osteoinductive material may also be an admixture of BMP and a polymeric acrylic ester carrier, such as polymethylmethacrylic.

Figure 48:
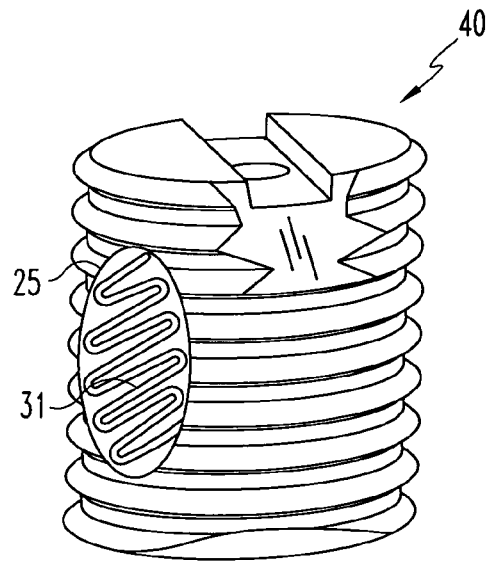
FIG. 48 is a side perspective view of a dowel with an osteogenic composition packed within the chamber.

For packing the chambers of the spacers of the present invention, the carriers are preferably provided as a sponge 58,30 which can be compressed into the chamber 55 (FIG. 25) or 25 (FIG. 47) or as strips or sheets 31 which may be folded to conform to the chamber as shown in FIG. 48. Preferably, the carrier has a width and length which are each slightly greater than the width and length of the chamber. In the most preferred embodiments, the carrier is soaked with a rhBMP-2 solution and then compressed into the chamber. As shown in FIG. 47, the sponge 30 is held within the chamber 25 by the compressive forces provided by the sponge 30 against the wall 22 of the dowel 21. It may be preferable for the carrier to extend out of the openings of the chamber to facilitate contact of the osteogenic composition with the highly vascularized tissue surrounding the fusion site. The carrier can also be provided in several strips sized to fit within the chamber. The strips can be placed one against another to fill the interior. As with the folded sheet, the strips can be arranged within the spacer in several orientations. Preferably, the osteogenic material, whether provided in a sponge, a single folded sheet or in several overlapping strips, has a length corresponding to the length and width of the chamber.

Figure 49:
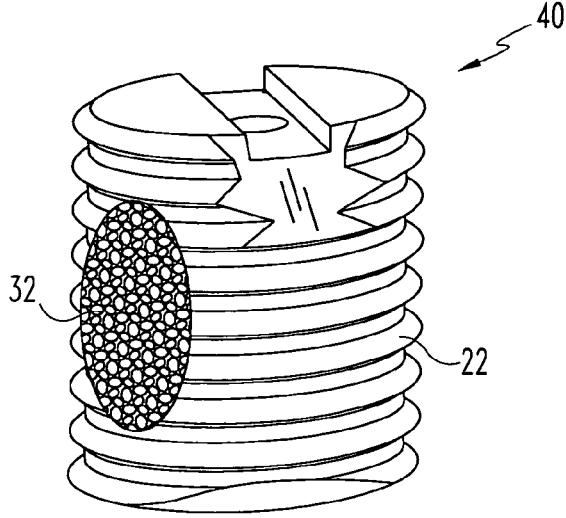
FIG. 49 is a side perspective view of a dowel with a ceramic carrier packed within the chamber.

The most preferred carrier is a biphasic calcium phosphate ceramic. FIG. 49 shows a ceramic carrier 32 packed within a dowel 40. Hydroxyapatite/tricalcium phosphate ceramics are preferred because of their desirable bioactive properties and degradation rates in vivo. The preferred ratio of hydroxyapatite to tricalcium phosphate is between about 0:100 and about 65:35. Any size or shape ceramic carrier which will fit into the chambers defined in the load bearing member are contemplated. Ceramic blocks are commercially available from Sofamor Danek Group, B. P. 4-62180 Rang-du-Fliers, France and Bioland, 132 Route d:Espagne, 31100 Toulouse, France. Of course, rectangular and other suitable shapes are contemplated. The osteoinductive factor is introduced into the carrier in any suitable manner. For example, the carrier may be soaked in a solution containing the factor.

In a preferred embodiment, an osteogenic composition is provided to the pores of the load bearing member. The bone growth inducing composition can be introduced into the pores in any suitable manner. For example, the composition may be injected into the pores of the graft. In other embodiments, the composition is dripped onto the graft or the graft is soaked in a solution containing an effective amount of the composition to stimulate osteoinduction. In either case the pores are exposed to the composition for a period of time sufficient to allow the liquid to thoroughly soak the graft. The osteogenic factor, preferably a BMP, may be provided in freeze-dried form and reconstituted in a pharmaceutically acceptable liquid or gel carrier such as sterile water, physiological saline or any other suitable carrier. The carrier may be any suitable medium capable of delivering the proteins to the spacer. Preferably the medium is supplemented with a buffer solution as is known in the art. In one specific embodiment of the invention, rhBMP-2 is suspended or admixed in a carrier, such as water, saline, liquid collagen or injectable BCP. The BMP solution can be dripped into the graft or the graft can be immersed in a suitable quantity of the liquid. In a most preferred embodiment, BMP is applied to the pores of the graft and then lypholized or freeze-dried. The graft-BMP composition can then be frozen for storage and transport.

Advantageously, the intervertebral spacers of the present invention may not require internal fixation. The spacers are contained by the compressive forces of the surrounding ligaments and muscles, and the disc annulus if it has not been completely removed. Temporary external immobilization and support of the instrumented and adjacent vertebral levels, with a cervical collar, lumbar brace or the like, is generally recommended until adequate fusion is achieved.

Although the spacers and compositions of this invention make the use of metal devices typically unnecessary, the invention may be advantageously combined with such devices. The bone graft-osteogenic compositions of the invention can be implanted within any of the various prior art metal cages.

The following specific examples are provided for purposes of illustrating the invention, and no limitations on the invention are intended thereby.

EXPERIMENTAL I

Preparation of Devices

EXAMPLE 1

Diaphysial Cortical Bone Dowel

A consenting donor (i.e., donor card or other form of acceptance to serve as a donor) was screened for a wide variety of communicable diseases and pathogens, including human immunodeficiency virus, cytomegalovirus, hepatitis B, hepatitis C and several other pathogens. These tests may be conducted by any of a number of means conventional in the art, including but not limited to ELISA assays, PCR assays, or hemagglutination. Such testing follows the requirements of: (i) American Association of Tissue Banks, Technical Manual for Tissue Banking, Technical Manual—Musculoskeletal Tissues, pages M19-M20; (ii) The Food and Drug Administration, Interim Rule, Federal Register/Vol. 50, No. 238/Tuesday, Dec. 14, 1993/Rules and Regulations/65517, D. Infectious Disease Testing and Donor Screening, (iii) MMWR/Vol. 43/No. RR-8, Guidelines for Preventing Transmission of Human Immunodeficiency Virus Through Transplantation of Human Tissue and Organs, pages 4-7; (iv) Florida Administrative Weekly, Vol. 10, No. 34, Aug. 21, 1992, 59A-1.001-014 59A-1.005(12)(c), F.A.C., (12)(a)-(h), 59A-1.005(15), F.A.C., (4)(a)-(8). In addition to a battery of standard biochemical assays, the donor, or their next of kin, was interviewed to ascertain whether the donor engaged in any of a number of high risk behaviors such as having multiple sexual partners, suffering from hemophilia, engaging in intravenous drug use etc. After the donor was ascertained to be acceptable, the bones useful for obtention of the dowels were recovered and cleaned.

A dowel was obtained as a transverse plug from the diaphysis of a long bone using a diamond tipped cutting bit which was water cleaned and cooled. The bit was commercially available (Starlite, Inc) and had a generally circular nature and an internal vacant diameter between about 10 mm to about 20 mm. The machine for obtention of endo- and cortical dowels consisted of a pneumatic driven miniature lathe which is fabricated from stainless steel and anodized aluminum. It has a spring loaded carriage which travels parallel to the cutter. The carriage rides on two runners which are 1.0 inch stainless rods and has a travel distance of approximately 8.0 inches. One runner has set pin holes on the running rod which will stop the carriage from moving when the set pin is placed into the desired hole. The carriage is moveable from side to side with a knob which has graduations in metric and in English. This allows the graft to be positioned. On this carriage is a vice which clamps the graft and holds it in place while the dowel is being cut. The vice has a cut out area in the jaws to allow clearance for the cutter. The lathe has a drive system which is a pneumatic motor with a valve controller which allows a desired RPM to be set.

First, the carriage is manually pulled back and locked in place with a set pin. Second, the graft is loaded into the vice and is aligned with the cutter. Third, the machine is started and the RPM is set, by using a knob on the valve control. Fourth, the set pin allows the graft to be loaded onto the cutter to cut the dowel. Once the cutter has cut all the way through the graft the carriage will stop on a set pin. Fifth, sterile water is used to eject the dowel out of the cutter. It is fully autoclavable and has a stainless steel vice and/or clamping fixture to hold grafts for cutting dowels. The graft can be positioned to within one thousandth of an inch (0.001") which creates dowel uniformity during the cutting process.

The cutter used in conjunction with the above machine can produce dowels ranging from 5 mm to 30 mm diameters and the sizes of the cutters are 10.6 mm; 11.0 mm; 12.0 mm; 13.0 mm; 14.0 mm; 16.0 mm; and 18.0 mm. The composition of the cutters is stainless steel with a diamond powder cutting surface which produces a very smooth surface on the wall of the dowels. In addition, sterile water is used to cool and remove debris from graft and/or dowel as the dowel is being cut (hydro infusion). The water travels down through the center of the cutter to irrigate as well as clean the dowel under pressure. In addition, the water aides in ejecting the dowel from the cutter.

The marrow was then removed from the medullary canal of the dowel and the cavity cleaned to create a chamber. The final machined product may be stored, frozen or freeze-dried and vacuum sealed for later use.

EXAMPLE 2

Threaded Dowels

A diaphysial cortical bone dowel is prepared as described above. The plug is then machined, preferably in a class 10 clean room, to the dimensions desired. The machining is preferably conducted on a lathe such as a jeweler's lathe or machining tools may be specifically designed and adapted for this purpose. A hole is then drilled through the anterior wall of the dowel. The hole is then tapped to receive a threaded insertion tool.

EXAMPLE 3

Bone Dowel Soaked with rhBMP-2

A threaded dowel is obtained through the methods of Examples 1 and 2.

A vial containing 4.0 mg of lyophilized rhBMP-2 (Genetics Institute) is constituted with 1 mL sterile water (Abbott Laboratories) for injection to obtain a 4.0 mg/mL solution is follows:

1. Using a 3-cc syringe and 22 G needle, slowly inject 1.0 mL sterile water for injection into the vial containing lyophilized rhBMP-2.

2. Gently swirl the vial until a clear solution is obtained. Do not shake.

The dilution scheme below is followed to obtain the appropriate rhBMP-2 concentration. This dilution provides sufficient volume for two dowels. The dilutions are performed as follows:

1. Using a 5-cc syringe, transfer 4.0 mL of MFR 906 buffer (Genetics Institute) into a sterile vial.

2. Using a 1-cc syringe, transfer 0.70 mL reconstituted rhBMP-2 into the vial containing the buffer.

3. Gently swirl to mix.

| DILUTION SCHEME | | | |
| --- | --- | --- | --- |
| INITIAL rhBMP-2 CONCENTRATION (mg/mL) | rhBMP-2 VOLUME (mL) | MFR-842 VOLUME (mL) | FINAL rhBMP-2 CONCENTRATION (mg/mL) |
| 4.0 | 0.7 | 4.0 | 0.60 |

1. Using a 3-cc syringe and 22 G needle, slowly drip 2.0 mL of 0.60 mg/mL rhBMP-2 solution onto the Bone Dowel.

2. Implant immediately.

EXAMPLE 4

Bone Dowel Packed with BMP-2/Collagen Composition

A threaded dowel is obtained through the methods of Examples 1 and 2.

A vial containing 4.0 mg of lyophilized rhBMP-2 (Genetics Institute) is constituted with 1 mL sterile water (Abbott Laboratories) for injection to obtain a 4.0 mg/mL solution as follows:

1. Using a 3-cc syringe and 22 G needle, slowly inject 1.0 mL sterile water for injection into the vial containing lyophilized rhBMP-2.

2. Gently swirl the vial until a clear solution is obtained. Do not shake.

The dilution scheme below is followed to obtain the appropriate rhBMP-2 concentration. The dilutions are performed as follows:

1. Using a 3-cc syringe, transfer 2.5 mL of MFR-842 buffer (Genetics Institute) into a sterile vial.

2. Using a 1-cc syringe, transfer 0.30 mL of 4.0 mg/mL reconstituted rhBMP-2 into the vial containing the buffer.

3. Gently swirl to mix.

| DILUTION SCHEME | | | |
| --- | --- | --- | --- |
| INITIAL rhBMP-2 CONCENTRATION (mg/mL) | rhBMP-2 VOLUME (mL) | MFR-842 VOLUME (mL) | FINAL rhBMP-2 CONCENTRATION (mg/mL) |
| 4.0 | 0.3 | 2.5 | 0.43 |

The rhBMP-2 solution is applied to a Helistat sponge (Genetics Institute) as follows:

1. Using sterile forceps and scissors, cut a 7.5 cm×2.0 cm strip of Helistat off of a 7.5×10 cm (3"×4") sponge.

2. Using a 1-cc syringe with a 22-G needle, slowly drip approximately 0.8 mL of 0.43 mg/mL rhBMP-2 solution uniformly onto the Helistat sheet.

3. Using sterile forceps, loosely pack the sponge into the chamber of the dowel.

4. Using a 1-cc syringe with a 22-G needle, inject the remaining 0.8 mL of 0.43 mg/mL rhBMP-2 into the sponge in the dowel through the openings of the chamber.

5. Implant immediately.

EXAMPLE 5

Bone Dowel Packed rhBMP-2/HA/TCP Composition

A threaded dowel is obtained through the methods of Examples 1 and 2.

A vial containing 4.0 mg of lyophilized rhBMP-2 (Genetics Institute) is constituted with 1 mL sterile water (Abbott Laboratories) for injection to obtain a 4.0 mg/mL solution as follows:

1. Using a 3-cc syringe and 22 G needle, slowly inject 1.0 mL sterile water for injection into the vial containing lyophilized rhBMP-2.

2. Gently swirl the vial until a clear solution is obtained. Do not shake.

A cylindrical block of biphasic hydroxyapatite/tricalcium phosphate (Bioland) is wetted with a 0.4 mg/mL rhBMP-2 solution. The BMP-ceramic block is packed into the chamber of the dowel and the dowel is then implanted.

EXAMPLE 6

Cortical Ring

A screened consenting donor is chosen as described in EXAMPLE 1 as follows. A cortical ring is obtained as a cross-sectional slice of the diaphysis of a human long bone and then prepared using the methods described in Example 1. The ring is packed with an osteogenic composition as described in EXAMPLE 4 or 5.

EXAMPLE 7

Spacers

A screened consenting donor is chosen as described in EXAMPLE 1. A D-shaped cervical spacer is obtained as a cross-sectional slice of a diaphysis of a long bone and then prepared using the methods of Example 1. The exterior surfaces of the walls are formed by machining the slice to a D-shape. The engaging surfaces of the spacer are provided with knurlings by a standard milling machine. A hole is then drilled through the anterior wall of the spacer. The hole is then tapped to engage a threaded insertion tool. The chamber of the spacer is then packed with an osteogenic composition as described in EXAMPLE 4 or 5.

EXPERIMENTAL II

Biomechanical Testing

EXAMPLE 10

Static Testing of Threaded Cortical Dowels Under Axial Loading

Figure 53:
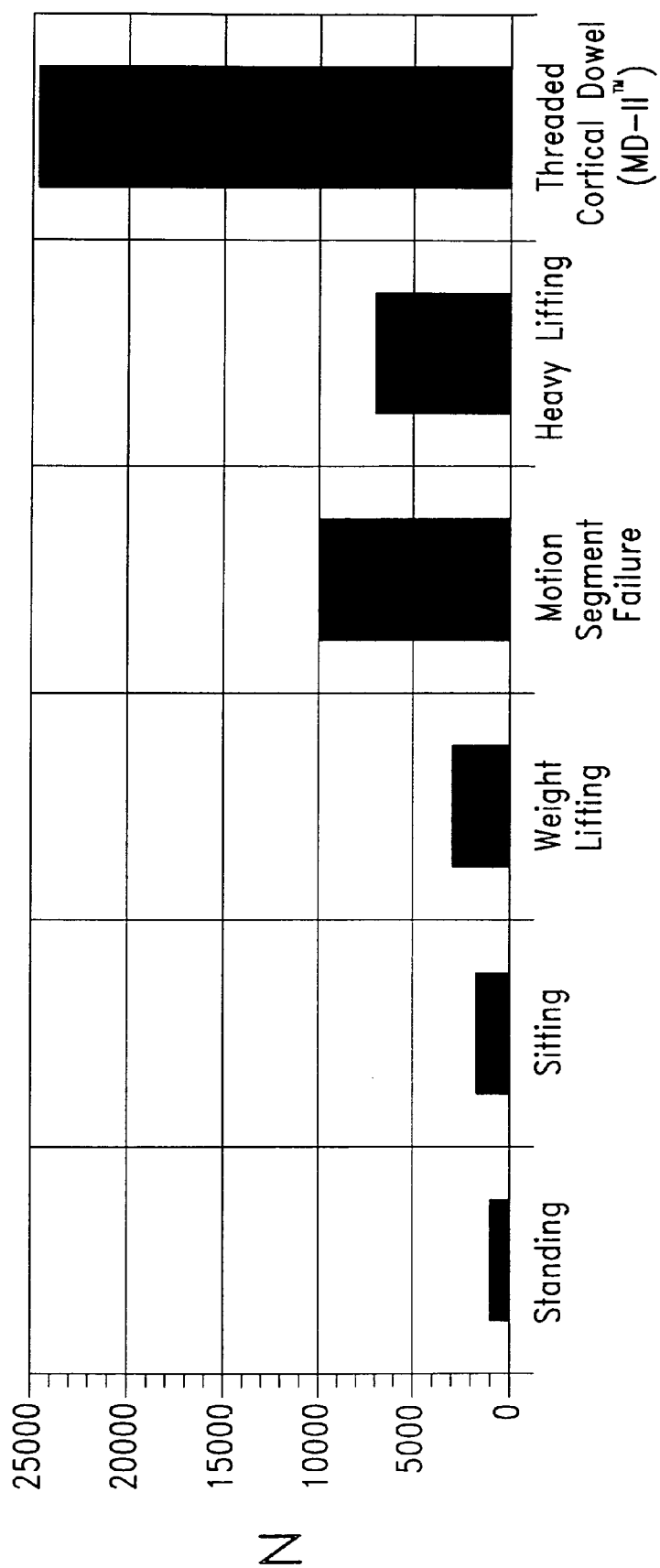
FIG. 53 compares the compressive strength of a threaded cortical dowel to in vivo spinal loads.
Figure 54:
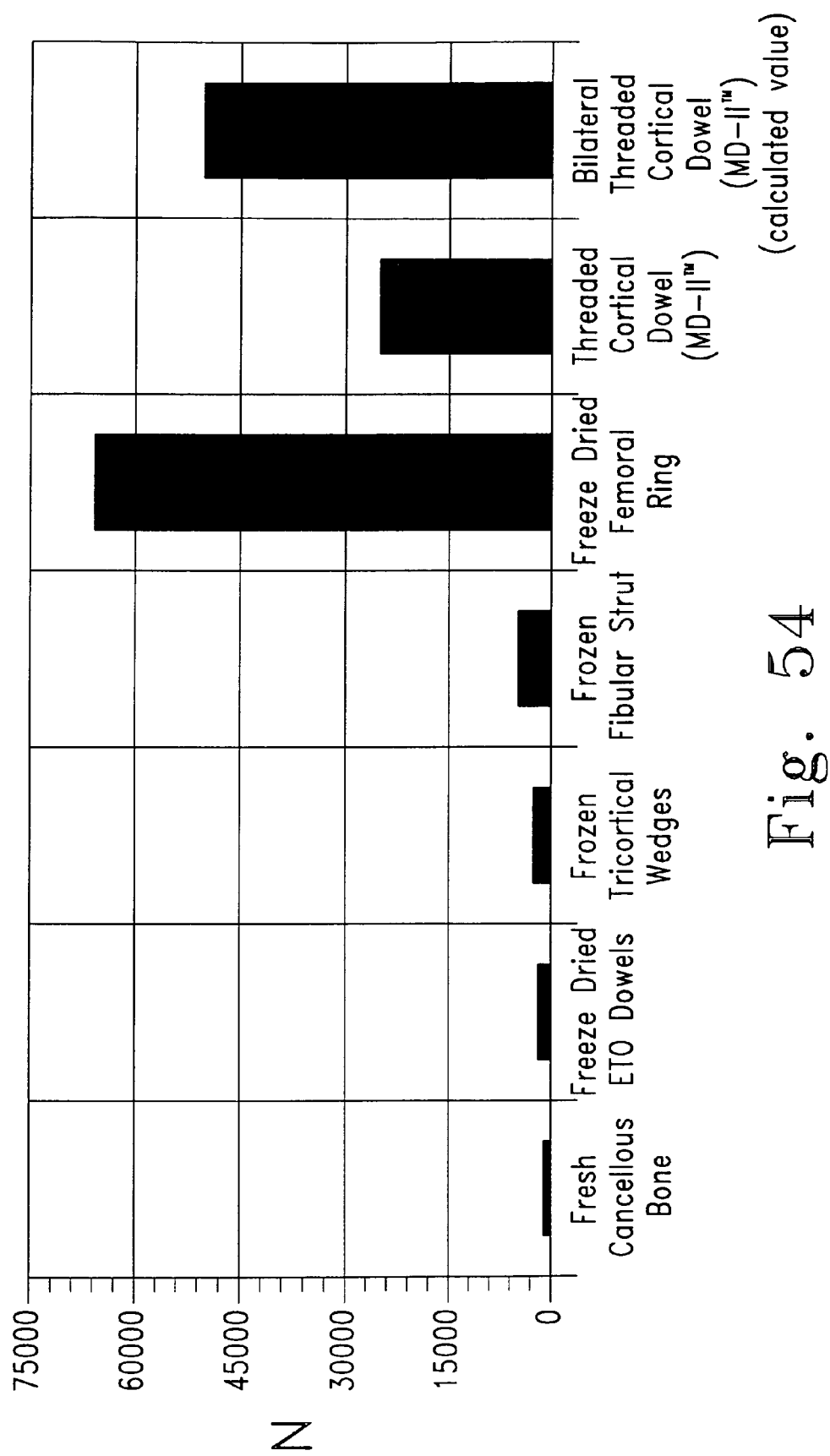
FIG. 54 compares the compressive strength of the load bearing members of this invention to other known graft materials.
Figure 55:
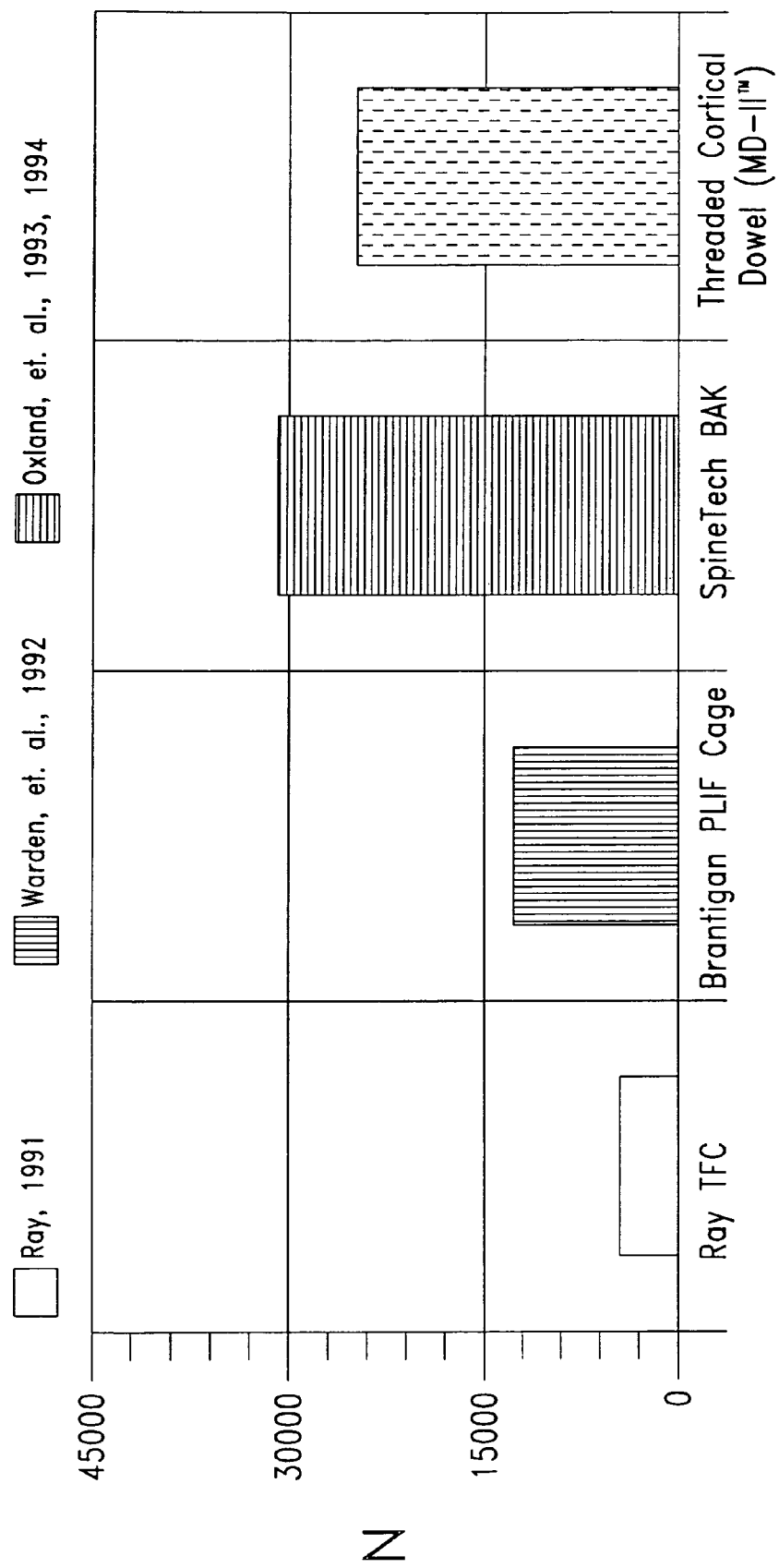
FIG. 55 compares the compressive strength of a load bearing member of this invention to fusion cages.

Static testing was performed to assure that the dowels were able to withstand maximum physiologic loading, of at least 10,000 N, the maximum expected lumbar load. Eighteen (18) mm outer diameter, frozen threaded cortical dowels 40 were obtained from the University of Florida Tissue Bank and thawed for testing with an axial test fixture 300. Four (4) samples of the threaded cortical dowel were inserted into two prepared plastic (polyacetal polymer) blocks 301, 302, having matching geometry with the threaded cortical dowels 40 as shows in FIGS. 50-52. The plastic blocks 301, 302 were attached to metallic blocks 303, 304 to ensure uniform loading across the dowel 40. A disc height H of 9 mm was used for the testing. An axial load P was applied via a servohydraulic test machine to the blocks 301, 302, 303, 304 at a rate of 25 mm/min. until failure of the dowel 40. The load-displacement curves were recorded.
Results:

The threaded dowels yielded at an average load of 24,733 N. The compressive strength of the threaded cortical dowels provides for a significant safety factor compared to both typical and maximum physiological spinal loading as shown in FIG. 53. These values range from 1000 N when standing to 10,000 N for heavy lifting. The compressive strength of threaded cortical dowels and cortical rings exceeds that of most available bone materials used for interbody fusion as shown in FIG. 54. Overall, the threaded cortical dowels and cortical rings tested demonstrated superior compressive strength compared to available options, with the exception of the femoral ring allograft. Note that the testing was for a single dowel. Clinically, most cases involve the placement of dual, bilateral dowels. Therefore, the expected average maximum compressive load for 2 dowels would be 49,466 N, comparable to the femoral ring allograft values. The threaded cortical dowels also compare favorably to artificial interbody implants as shown in FIG. 55.

EXAMPLE 11

Dynamic Testing of Threaded Cortical Dowels Under Axial Loading

Dynamic testing determines the fatigue performance of the dowel under cyclic loading. Cycles to failure are determined at various load levels. Resistance to fatigue is important to the performance of spinal implants. The implant must be able to withstand cyclic in vivo loading until fusion occurs. It is estimated that the average person makes 2 million strides per year (1 million gait cycles) and 125,000 significant bends per year. Therefore, the typical dynamic testing run-out value of 5 million cycles simulates approximately 2 years of cyclic loading prior to fusion and ultimate complete spinal motion segment stabilization.

Figure 56:
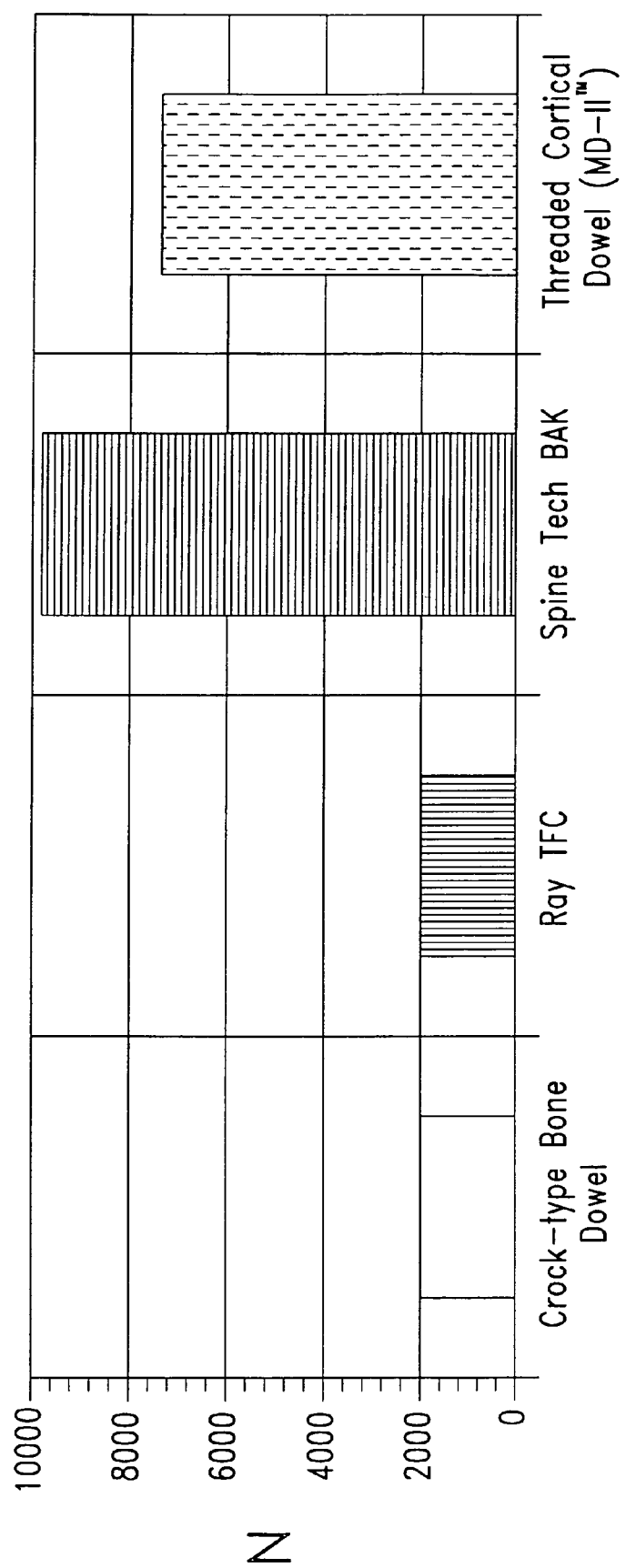
FIG. 56 compares the fatigue loading values for various spinal implants in axial compression.

The fixture 300 (FIGS. 50-52) described in Example 11 for the axial static testing was used to apply dynamic alternating loads to various implants and dowels. Initial fatigue loads were determined based on the maximum static load value. Initial fatigue loads were 75%, 50% and 25% of the ultimate strength value of 24,733 N. Additional data points were then generated to determine the five million cycle runout value.
Results:

Based on the previously discussed physiologic loading values, an average every day loading value is expected to be a fraction of the maximum values and is estimated at approximately 3,200 N. This typical loading value can then be used to assess the fatigue performance of the various interbody fusion alternatives. For the threaded cortical dowel, runout was achieved at a level of 30% of the maximum static load. That is, a minimum of 2 samples reached 5 million cycles at an applied load of 7,420 N as shown in FIG. 56. This value is well above the average loading value of 3,200 N.

EXAMPLE 12

Static and Dynamic Testing of Threaded Cortical Dowels Under Bending Loads

Figure 58:
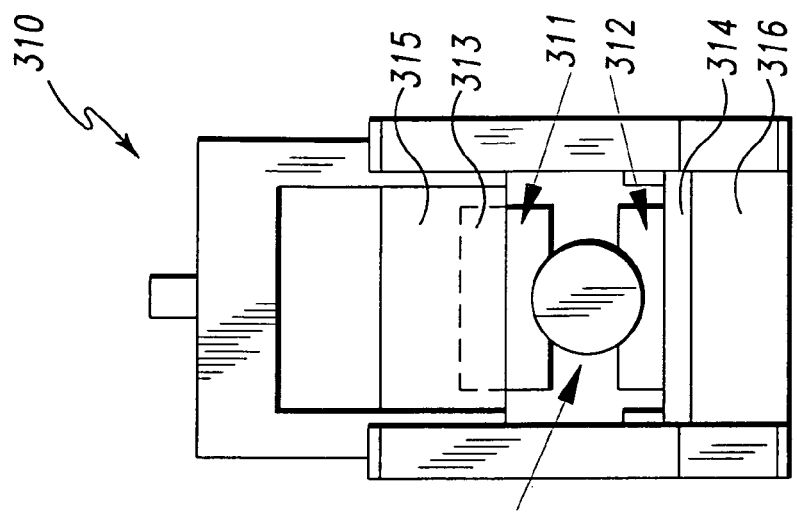
FIG. 58 is a front elevational view of the fixture shown in FIG. 57.
Figure 57:
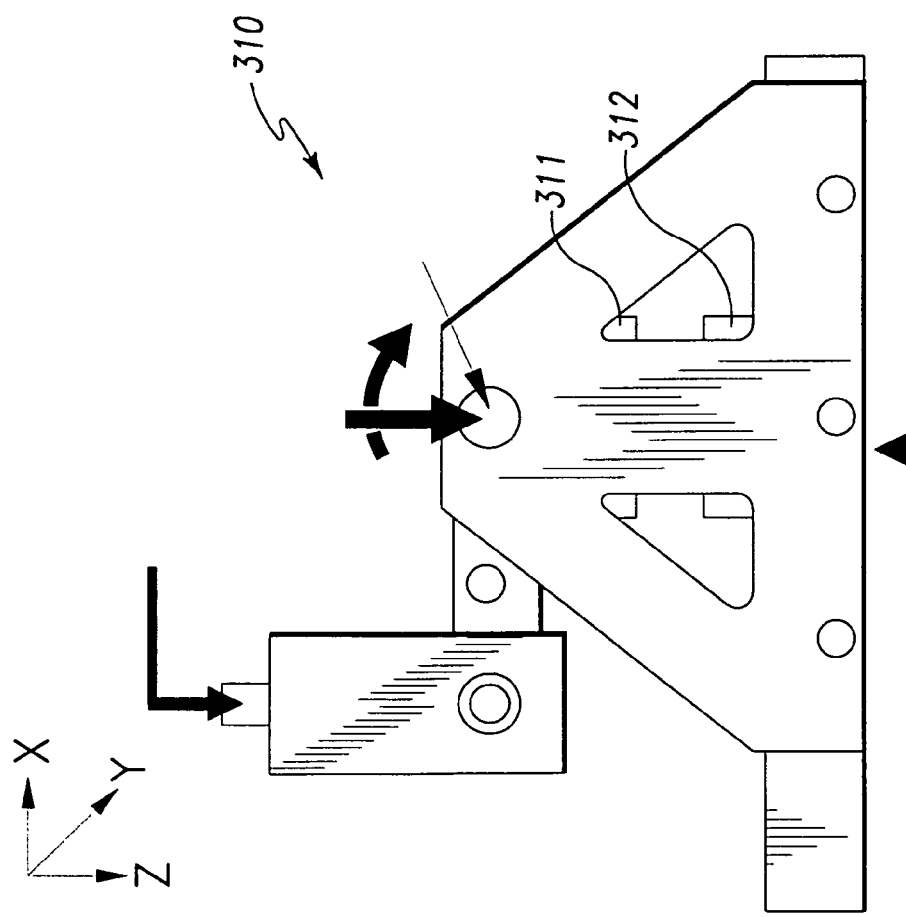
FIG. 57 is a side elevational view of a multi-axial loading test fixture.

While compressive testing provided valuable comparative information regarding the dynamic and static performance of the dowels, it is a simplification of the loading seen by the dowels in the clinical settings. In order to better simulate the loading seen clinically, a special flexion-extension or multi-axial cyclic test fixture 310 was developed (FIGS. 57 and 58). Dowels were tested in both static and dynamic loading situations. The specially designed fixture applied complex, multi-axial loading to the dowels.

The dowels were placed into pre-tapped plastic (polyacetal polymer) blocks 311, 312. The plastic blocks 311, 312 are affixed to recessed pockets 313, 314 in the upper 315 and lower 316 plates of the metal test fixture 310. Vertical loads L are applied to generate the flexion-extension bending moments. Cyclic compressive loads are applied, and a bending moment is generated by the 7.6 cm loading arm.

Two dowels were subject to a static load to failure in the test fixture. The maximum load value was then used to determine dynamic loading values. For the fatigue testing, fully reversed loading was applied, simulating flexion-extension cycles. Cyclic testing was carried out at values of 40%, 30% and 20% of the maximum load value and the 5 million cycle runout value was determined.
Results:

The average static load to failure value for the threaded cortical dowel was found to be 1,545 N. Given the 7.6 cm moment arm, this translates into a value of 138 N-m maximum bending load. The 5 million cycle runout value was approximately 450 N. Again, given the 7.6 cm moment arm, this translates into a value of 40.5 N-m bending load. It is reported that the failure load of a lumbar motion segment in bending is 33 N-m on average. The maximum static load value is over 4 times higher than this value, and the dynamic, multi-axial runout value is above this maximum bending load value.

EXAMPLE 13

Insertion Torque Testing of Threaded Cortical Dowels

Figure 59:
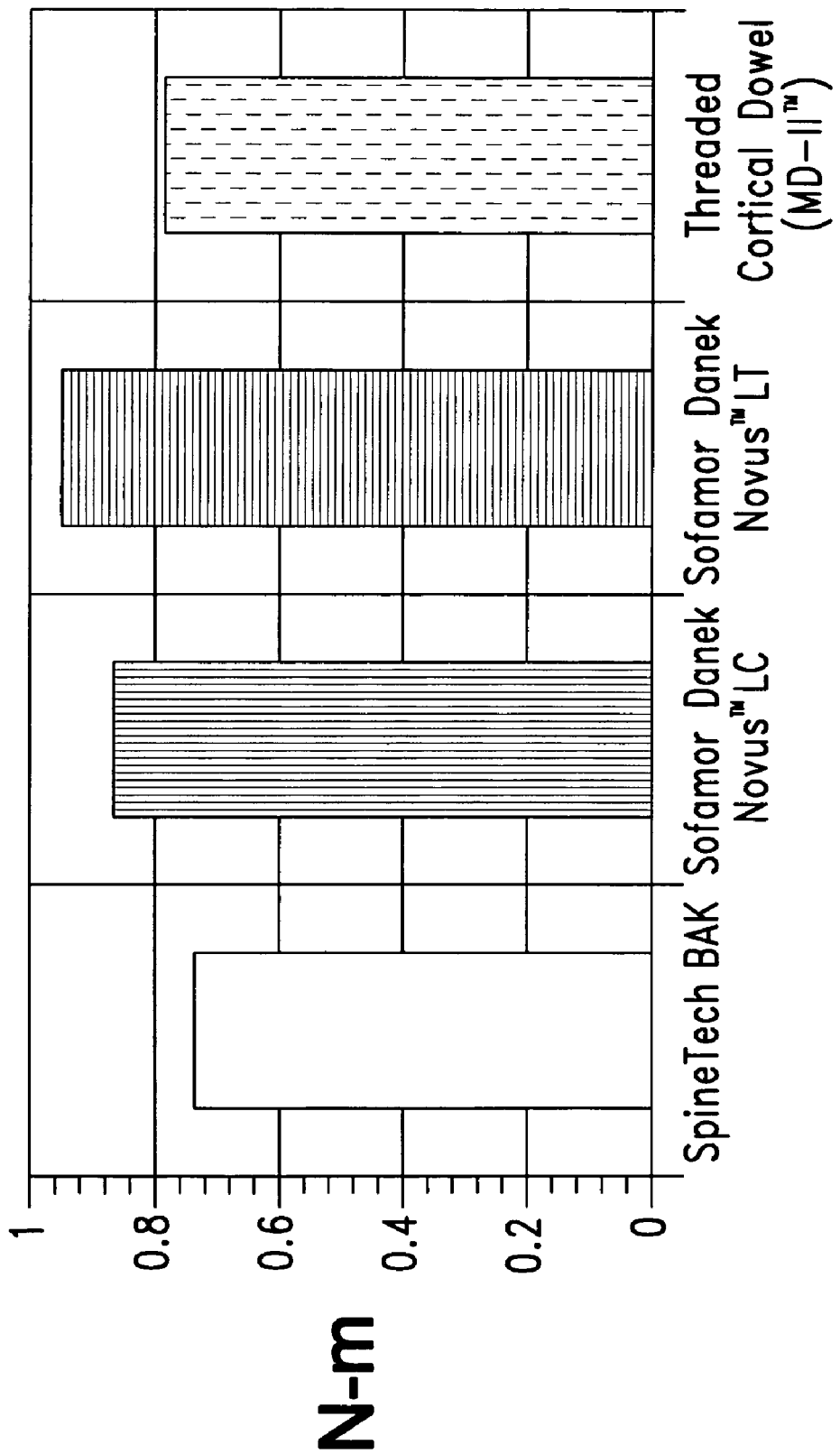
FIG. 59 compares insertion torque values for threaded cortical dowels and other threaded fusion spacers.

Benchtop testing was performed to study the insertion torque required to insert the dowels and to compare these values with that of threaded interbody fusion devices. Two (2) lumbar calf spines were used for the insertion torque testing. Due to size constraints, an 18 mm threaded cortical dowel was inserted into the lowest two lumbar levels of each spine. The disc spaces were dilated and the space was reamed and then tapped. A specially modified driver was used to place the dowels and measure the insertion torque.
Results:

No damage was noted to any of the dowels upon examination after insertion. The average insertion torque value was found to be 0.78 N-m. The threaded cortical dowel compared favorably to known values for metal threaded fusion devices as shown in FIG. 59.

Summary of Threaded Cortical Dowel Testing

The biomechanical testing demonstrates that the threaded cortical dowels are well suited for interbody fusion applications. The test information is summarized as follows:

1. The static strength of threaded cortical dowels provides for a substantial safety factor over maximum physiologic load levels. The dowels are stronger than alternative bone dowel constructs. Their strength exceeds that of the Brantigan composite PLIF cage and the Ray TFC device and is comparable in strength to the SpineTech BAK.

2. The fatigue strength of the threaded cortical dowels exceeds that of conventional Crock-type bone dowels and provides for a substantial safety factor over typical, daily living load levels. The fatigue strength of the dowels exceeds that of the Ray TFC device and is comparable to the SpineTech BAK device.

3. The dowels are able to resist maximum bending loads, providing for a substantial safety factor in static loading and demonstrating 5 million cycle runout at a value above the maximum expected bending loads.

4. The torque required to insert the devices is comparable with that seen with threaded fusion cages. No damage to the threads or the dowel drive attachment were detected when inserting and revising the dowels.

Overall, the threaded cortical dowels possess the required biomechanical properties to facilitate interbody fusion in the lumbar spine. Their physical strength well exceeds the expected physiological loading and is superior to other bone graft alternatives. The dowels outperform or are comparable to all currently available fusion cage alternatives.

EXAMPLE 14

Evaluation of rhBMP-2 as a Bone Graft Enhancing Agent

The purpose of this study was to determine the effect of using BMP to augment allograft to fill a gap surrounding a porous coated implant. A non-weight bearing canine model was used.
Raw Materials

| MATERIAL | SOURCE/ LOT # | COMMENTS | AMOUNT SUPPLIED |
|---|---|---|---|
| rhBMP-2 | Generics Institute Lot# 0214C01 TQ Fill | 4 mg/mL rhBMP-2 in 5 mM sodium glutamate, 2.5% glycine, 0.5% sucrose, 0.01% Tween 80, pH 4.5 | 4 vials at 4 mg/vial lyo. from MFR842 buffer |

-continued

| MATERIAL | SOURCE/ LOT # | COMMENTS | AMOUNT SUPPLIED |
|---|---|---|---|
| MFR842 Buffer | Genetics Institute Lot # 26256 | 5 mM sodium glutamate, 2.5% glycine, 0.5% sucrose, 0.01% Tween 80, pH 4.5 | 4 vials at 5 mL/vial |
| Irradiated Fresh, Frozen Canine Allograft | Donor Canines | Irradiated 2.5 Mrads (24-26) KG's | Approximately 10-15 mLs |
| Vitallium Porous Coated Plugs | Howmedica | 5.4 mm diameter | N/A |
| Teflon Washers | Howmedica | I.D. 6.4 mm, O.D. 10.4 mm | N/A |
| Autogenic blood | N/A | N/A | N/A |
| Sterile Water for Injection | Abbott Labs Lot # 90-544-OK | WFI USP Grace | 4 vials at 10 mL/vial |

Composition and Graft Preparation
1. Allograft Preparation
   a. Draw 1 mL canine blood.
   b. Add 0.700 mL canine blood to a sterile 1.5 mL Eppendorf tube.
   c. Mark level on this tube.
   d. Mark level on a second tube and discard the tube containing blood.
   e. Mark level on three additional tubes.
   f. Add allograft to level marked on tubes.
2. Allograft/Blood/rhBMP-2 Compositions
   a. Reconstitute the rhBMP-2 using 1 mL, room temperature, sterile water for injection (WFI). Inject the WFI into a vial of rhBMP-2, along the inside surface of the vial. Gently swirl the vial 3-4 times. The final concentration is 4 mg/mL.
   b. Draw 1.0 mL canine blood and place in a sterile eppendorf tube.
   c. Draw 0.550 mL of blood from the tube and place into a second Eppendorf tube.
   d. Add 0.050 mL blood of the reconstituted rhBMP-2 solution to the 0.550 mL blood and mix gently with a siliconized pipet tip.
   e. Add 0.300 mL of the blood/rhBMP-2 mixture to the eppendorf tube containing the allograft.
   f. Stir the material gently with a sterile spatula until well mixed.
   g. Let clot at room temperature for 1 hour.
3. Allograft/Blood/MFR842 Composition
   a. Draw 1.0 mL canine blood and place in a sterile eppendorf tube.
   b. Draw 0.550 mL of blood from the tube and place into a second eppendorf tube.
   c. Add 0.050 mL of the MFR842 Buffer to the 0.550 mL blood and mix gently with a siliconized pipet tip.
   d. Add 0.300 mL of the blood/MFR842 mixture to the eppendorf tube containing the allograft.
   e. Stir the material gently with a sterile spatula until well mixed.
   f. Let clot at room temperature for 1 hour.

Surgery

Graft compositions were placed across each femoral condyle with a 2 mm cap maintained throughout the cancellous region of the condyle. The composition on the left included fresh-frozen allograft and the composition on the right included fresh-frozen allograft plus rhBMP-2 as shown in the table below.

| Scheme | | | |
|---|---|---|---|
| Canine ID | Control: Bone Graft Only | Treated: Bone + rhBMP-2 | Time |
| 94-975 | Right leg | Left leg | 14 days |
| 94-973 | Right legg | Left leg | 14 days |
| 94-913 | Right leg | Left leg | 28 days |
| 94-914 | Right leg | Left leg | 28 days |

The implanted compositions were evaluated radiographically and effectiveness was tested using biomechanical shear testing or push-out strength. Five mm thick sections were obtained for the push-out tests by making a first cut 5 mm from the lateral end of the metal implant and a second cut 5 mm from the first cut. This resulted in three sections per bone specimen with the exception of one specimen which yielded four sections due to repositioning of the bone block. The biomechanical tests were completed using a computer-linked servohydraulic materials tester.

Results

The surgeries were uneventful. The dogs were all full weight bearing within 3 days (2+/−1.15).

Presurgical radiographs of the distal femora from all animals revealed normal, mature bone structure with no radiographic pathology. Post-operative and terminal evaluation of the implantation sites were performed to assure the correctness of implant placement and to document changes around the implant site. No fractures or other surgical complications were recognized on the radiographic images.

Push-out (compression) was achieved using a rate of 0.5 mm/sec. All specimens appeared to fail at the graft-metal interface. All of the two week specimens could be pushed out easily by finger-touch or by gravity alone. Push out testing does not appear to be an adequate parameter for comparison of the treated vs. un-treated groups at this time period. Specimens from the treated animals at the 4 week time period were clearly superior to the untreated specimens as shown in the table below.

| Load to Failure Values(N) | | | |
|---|---|---|---|
| Canine ID | Time After Surgery | Left Graft + BMP | Right Graft Alone |
| 975 | 2 weeks | 8.71 | 24.43 |
| 973 | 2 weeks | 17.45 | 12.22 |
| 913 | 4 weeks | 82.88 | 41.88 |
| 914 | 4 weeks | 76.78 | 13.96 |

Push-out strength for the BMP-treated specimens was superior to the graft alone specimens after four weeks, suggesting a BMP enhancement of mechanical strength. The failure at the graft-metal interface indicates a weak bond between the metal and bone four weeks postoperatively.

CONCLUSION

The combination of BMP with a bone graft provides superior results. Quicker fusion rates provide enhanced mechanical strength sooner. Bone is an excellent protein carrier which provides controlled release of BMP to the fusion site. When the bone graft is a threaded cortical dowel, the biomechanical superiority of the load bearing dowel is superbly combined with the enhanced fusion rates of the BMP-bone combination.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A spinal spacer for insertion into a disc space between adjacent vertebrae, said spacer comprising a cylindrical bone dowel configured for engagement within a concave space cut in the adjacent vertebrae, said bone dowel comprising a cortical bone section cut from a bone of a donor, said cortical bone section having impregnated therein an effective amount of a first osteogenic composition including a first substantially pure osteogenic factor.

2. The spacer of claim 1 wherein said osteogenic factor is a purified bone morphogenic protein isolated from bone.

3. The spacer of claim 1 wherein said osteogenic factor is selected from the group consisting of BMP-1, BMP-2, BMP-3, BMP-4, BMP-5, BMP-6, BMP-7, BMP-8, BMP-9, BMP-10, BMP-11, BMP-12, BMP-13, a mixture thereof and a heterodimer thereof.

4. The spacer of claim 1 wherein the bone dowel is configured with threads for engaging in the concave space cut in the adjacent vertebrae.

5. The spacer of claim 1 wherein the bone dowel is configured to be impacted into the concave space.

6. The spacer of claim 1 wherein said osteogenic factor is a recombinant human protein.

7. The spacer of claim 6 wherein said osteogenic factor is rhBMP-2, rhBMP-4, rhBMP-7 or a mixture or heterodimer thereof.

8. The spacer of claim 1 wherein said dowel is porous and said first osteogenic composition is contained within said pores.

9. The spacer of claim 1 wherein said bone dowel defines a chamber.

10. The spacer of claim 9 wherein said bone dowel is obtained from the diaphysis of a long bone having a medullary canal and wherein the chamber comprises a portion of said medullary canal.

11. The spacer of claim 9 further comprising an effective amount of a second osteogenic composition to stimulate osteoinduction, said second composition packed within said chamber.

12. The spacer of claim 11 wherein said second osteogenic composition includes a pharmaceutically acceptable carrier having a length which is greater than a length of said chamber and said second osteogenic composition is disposed within said chamber to contact the endplates of adjacent vertebrae when the spacer is implanted between the vertebrae.

13. The spacer of claim 12 wherein said second osteogenic composition is selected from the group consisting of autograft, allograft, demineralized bone, calcium phosphate ceramics, and an osteoinductive factor disposed within a pharmaceutically acceptable matrix.

14. The spacer of claim 12 wherein said carrier is provided as a sponge, a strip, or a sheet.

15. The spacer of claim 1 wherein said bone dowel includes an anterior wall and said anterior wall defines a tool engaging hole for receiving an implanting tool.

16. The spacer of claim 1 wherein said bone dowel has an outer surface defining a thread, said thread including plurality of teeth each tooth of the plurality of teeth having a crest between a leading flank and an opposite trailing flank.

17. The spacer of claim 16 wherein said crest of each said tooth is flat.

18. The spacer of claim 16 wherein said dowel includes a tool engaging portion defining a tool engaging hole for receiving an implanting tool.

19. The spacer of claim 18 wherein said tool engaging hole is threaded to receive a threaded implanting tool.

20. The spacer of claim 1 wherein said first osteogenic factor is provided in a pharmaceutically acceptable carrier.

21. The spacer of claim 20 wherein said carrier is physiological saline.

22. The spacer of claim 20 wherein said carrier is buffered sterile water.

23. A spinal spacer for insertion into a disc space, said spacer comprising a bone graft comprising a cortical bone section cut from a bone of a donor, said cortical bone section having impregnated therein an effective amount of a first osteogenic composition including a first substantially pure osteogenic factor, said bone graft including a chamber and having a wall sized to maintain a desired disc space height, and an effective amount of a second osteogenic composition including a second substantially pure osteogenic factor packed within said chamber.

24. The spacer of claim 23 wherein said bone graft is obtained from the diaphysis of a long bone having a medullary canal.

25. The spacer of claim 23 wherein at least one of said first and second osteogenic factors comprises a purified bone morphogenic protein isolated from bone.

26. The spacer of claim 25 wherein at least one of said first and second osteogenic factors is selected from the group consisting of BMP-1, BMP-2, BMP-3, BMP-4, BMP-5, BMP-6, BMP-7, BMP-8, BMP-9, BMP-10, BMP-11, BMP-12, BMP-13, a mixture thereof and a heterodimer thereof.

27. The spacer of claim 23 wherein at least one of said first and second osteogenic factors comprises a recombinant human bone morphogenic protein.

28. The spacer of claim 27 wherein said bone morphogenic protein is rhBMP-2, rhBMP-4, rhBMP-7, or a mixture or heterodimer thereof.

29. The spacer of claim 23 wherein said second osteogenic factor is provided in a pharmaceutically acceptable matrix packed within said chamber.

30. The spacer of claim 29 wherein said matrix is selected from the group consisting of calcium sulphates, polylactic acids, polyanhydrides, collagen, calcium phosphates, polymeric acrylic esters, and mixtures thereof.

31. The spacer of claim 29 wherein said matrix is a biphasic calcium phosphate ceramic including hydroxyapatite and tricalcium phosphate.

32. The spacer of claim 31 wherein the ratio of hydroxyapatite to tricalcium phosphate is between about 0:100 and about 65:35.

33. The spacer of claim 29 wherein said pharmaceutically-acceptable matrix is provided as a sponge, a strip, or a sheet.

34. The spacer of claim 23 wherein said spacer includes a tool engaging hole for receiving an implanting tool.

35. The spacer of claim 34 wherein said tool engaging hole is threaded.

36. The spacer of claim 23 wherein said spacer comprises an outer surface defining a thread.

37. The spacer of claim 36 wherein said thread has a flat crest having a width of between about 0.020 inches and about 0.030 inches.

38. The spacer of claim 36 wherein said thread has a leading flank and a trailing flank defining an angle therebetween of between about 50 degrees and about 70 degrees.

39. The spacer of claim 36 wherein each said thread has a height between about 0.030 inches and about 0.045 inches.

40. The spacer of claim 23 wherein said graft is a cortical ring obtained by a cross-sectional slice of the diaphysis, said ring including superior and inferior surfaces and wherein at least one of said first and second osteogenic factors comprises a bone morphogenic protein.

41. The spacer of claim 40 adapted to withstand a compressive force of at least 10,000 N.

42. The spacer of claim 41 adapted to withstand a compressive force of at least 20,000 N.

43. The spacer of claim 40 adapted to exhibit a fatigue strength of at least 3200 N at five million cycles.

44. The spacer of claim 43 adapted to exhibit a fatigue strength of at least 7000 N at five million cycles.

45. The spacer of claim 23 wherein said wall comprising a thru-hole into said chamber.

* * * * *